US009593109B2

(12) United States Patent
Song et al.

(10) Patent No.: US 9,593,109 B2
(45) Date of Patent: Mar. 14, 2017

(54) BICYCLIC AGONISTS OF GPR131 AND USES THEREOF

(75) Inventors: Jiangao Song, Sunnyvale, CA (US); Phuongly Pham, San Francisco, CA (US); Jingyuan Ma, Sunnyvale, CA (US); Aaron Robert Novack, San Jose, CA (US); Imad Nashashibi, San Jose, CA (US); David W. G. Wone, Newark, CA (US); Dong-Fang Shi, Fremont, CA (US); Xin Chen, San Ramon, CA (US)

(73) Assignee: CYMABAY THERAPEUTICS, INC., Hayward, CA (US)

( * ) Notice: Subject to any disclaimer, the term of this patent is extended or adjusted under 35 U.S.C. 154(b) by 352 days.

(21) Appl. No.: 13/594,598

(22) Filed: Aug. 24, 2012

(65) Prior Publication Data

US 2013/0059845 A1 Mar. 7, 2013

Related U.S. Application Data

(60) Provisional application No. 61/528,067, filed on Aug. 26, 2011.

(51) Int. Cl.
*C07D 307/78* (2006.01)
*C07D 307/79* (2006.01)
*C07D 471/04* (2006.01)
*C07D 473/04* (2006.01)
*C07D 498/04* (2006.01)

(52) U.S. Cl.
CPC ......... *C07D 471/04* (2013.01); *C07D 473/04* (2013.01); *C07D 498/04* (2013.01)

(58) Field of Classification Search
CPC ........................ C07D 307/79; C07D 307/78
See application file for complete search history.

(56) References Cited

U.S. PATENT DOCUMENTS

| | | | |
|---|---|---|---|
| 5,210,092 A | 5/1993 | Oku et al. | |
| 5,225,414 A | 7/1993 | Henning et al. | |
| 7,326,708 B2 | 2/2008 | Cypes et al. | |
| 8,552,022 B2 | 10/2013 | Wood et al. | |
| 2010/0323011 A1 | 12/2010 | Pourkavoos | |
| 2010/0330177 A1 | 12/2010 | Pourkavoos | |
| 2011/0152295 A1 | 6/2011 | Leclerc et al. | |
| 2011/0166152 A1 | 7/2011 | Leclerc et al. | |
| 2011/0294767 A1 | 12/2011 | Gedulin et al. | |
| 2013/0034536 A1 | 2/2013 | Gedulin | |
| 2013/0059856 A1 | 3/2013 | Novack et al. | |

FOREIGN PATENT DOCUMENTS

| | | | |
|---|---|---|---|
| WO | WO-2005/086836 A1 | 9/2005 | |
| WO | WO 2006/068199 A1 | 6/2006 | |
| WO | WO-2010/093845 A1 | 8/2010 | |
| WO | WO-2010/117090 A1 | 10/2010 | |

OTHER PUBLICATIONS

Alkhader et al. (1994); "Synthesis of some newer indazolyl-oxadiazoles, thiadiazoles and 1,2,4-trazoles," Qatar Univ. Sci. J. 14(C):114-122.
Barrett-Connor, "Epidemiology, obesity, and non-insulin-dependent diabetes mellitus," Epidemol. Rev. (1989) 11:172-181.
Berge, et al., "Pharmaceutical Salts," J. Pharma. Sciences (1977) 66(1):1-19.
Database CA [Online], Chemical Abstracts Service, Columbus, Ohio, US; Lahser et al.: "Antiviral HCV inhibitors and combination therapy," XP002684729, retrieved from STN Database accession No. 2010:1277297 abstract & WO 2010/117939 A1.
Database Registry [Online], Chemical Abstracts Service, Columbus, Ohio, US; Sep. 14, 2011, XP002684731, retrieved from STN Database accession No. 1332091-62-9 abstract.
Drucker, "Biological Actions and Therapeutic Potential of the Glucagon-like Peptides," Gastroenterology (2002) 122:531-544.
Expert Committee on the Diagnosis and Classification of Diabetes Mellitus, The, "Report of the expert committe on the diagnosis and classification of diabetes mellitus," Diabetes Care (1999) 2(Suppl 1):S5-S19.
Flier, "Insulin receptors and insulin resistance," Ann. Rev. Med. (1983) 34:145-160.
Gmeiner et al. (2003), "Synthesis and dopamine receptor binding of some pyrazolo [3',4':6,7]azepino[5,4,3-cd]indoles," Heterocycles 60(6):1339-1350.
Kaim et al. (2011); "Four-component synthesis of indazole through ugi-azide coupling," Synlett 23:295-297.
Katsuma et al., "Bile acids promote glucagon-like peptide-1 secretion through TGR5 in a murine enteroendocrine cell line STC-1," Biochem. Biophys. Res. Commun. (2005) 329(1):386-390.
Kawamata, et al., "A G protein-coupled receptor responsive to bile acids," J. Biological Chemistry (2003) 278(11):9435-9440.
Keitel, et al., "Expression and function of the bile acid receptor TGR5 in Kupffer cells," Biochemical and Biophysical Research Communications (2008) 372:78-84.
Knowler et al., "Obesity in the Pima Indians: its magnitude and relationship with diabetes," Am. J. Clin. Nutr. (1991) 53:1543S-1551S.

(Continued)

*Primary Examiner* — Jeffrey S Lundgren
*Assistant Examiner* — Chris Simmons
(74) *Attorney, Agent, or Firm* — Foley & Lardner LLP

(57) ABSTRACT

The present disclosure relates to compounds that act as agonists of, or otherwise modulate the activity of, GPR131 and to their use in the treatment of various diseases. In particular embodiments, the structure of the compounds is given by Formula I:

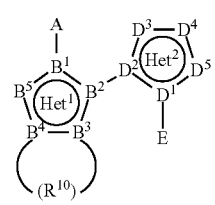

wherein the variables are as described herein. Related compositions, formulations and methods for the preparation of compounds of formula I are also described.

20 Claims, No Drawings

(56) References Cited

OTHER PUBLICATIONS

Maruyama, et al., "Identification of membrane-type receptor for bile acids (M-BAR)," Biochemical and Biophysical Research Communications (2002) 298:714-719.
Maruyama, et al., "Targeted disruption of G protein-coupled bile acid receptor 1 (Gpbarl/M-Bar) in mice," J. Endocrinology (2006) 191:197-205.
Rautio, et al., "Prodrugs: design and clinical applications," Nature Reviews (2008) 7:255-270.
Reaven, "Insulin resistance and human disease: a short history," J. Basic & Clin. Phys. & Pharm., (1998) 9(2-4):387-406.
Remington: The Science and Practice of Pharmacy, R. Hendrickson, ed., 21st edition, Lippincott, Williams & Wilkins, Philadelphia, PA, (2005), at p. 732, Table 38-5.
Thomas, et al., "TGR5-mediated bile acid sensing controls glucose homeostasis," Cell Metabolism (2009) 10:167-177.
Watanabe, et al., "Bile acids induce energy expenditure by promoting intracellular thyroid hormone activation," Nature (2006) 439:484-489.
International Search Report for Application No. PCT/US2012/052364 dated Oct. 19, 2012.
International Search Report and Written Opinion for Application No. PCT/US2012/042319 dated Jan. 30, 2013.

BICYCLIC AGONISTS OF GPR131 AND USES THEREOF

CROSS-REFERENCE TO RELATED APPLICATIONS

This application claims priority to U.S. Provisional Application Ser. No. 61/528,067, filed on Aug. 26, 2011, the complete disclosure of which is incorporated by reference herein.

BACKGROUND

This application relates to chemical compounds which act as agonists of, or otherwise modulate the activity of, GPR131, and to compositions and formulations containing such compounds, and methods of using and making such compounds. The compounds described herein may be used to treat one or more diseases such as diabetes, metabolic syndrome, and liver disease, conditions or symptoms of a disease such as inflammation, and other diseases or conditions for which modulation of GPR131 can provide a therapeutic benefit.

G protein-coupled receptors (GPCRs) comprise a large family of transmembrane receptors that sense molecules outside a cell and modulate signal transduction pathways and, consequently, various cellular responses. GPR131 (also known as BG37, TGR5, M-BAR, GPCR19, MGC40597, GPBAR1, and RUP43) is a GPCR that is activated by bile acids (BAs) such as lithocholic acid (LCA) and taurolithocholic acid (TLC), and oleanolic acid. Muruyama et al., *Biochem Biophys Res. Commun.*, 298:714-9 (2002) [PMID: 12419312] (2002); Kawamata et al., *J. Biol. Chem.*, 278: 9435-40 (2003) [PMID:12524422]. GPR131 is expressed in the gastro-intestinal tract and adipose as well as other tissues, and is also present in GLP-1 secreting enteroendocrine cell lines such as STC-1 (Katsuma et al., *Biochem. Biophys. Res. Commun.*, 329(1):386-90 (2005) [PMID: 15721318]) and NCI-H716. Since this receptor is coupled to signaling through the GαS protein, activation of GPR131 results in increases in cAMP. Bile acid ligands of GPR131 can increase cAMP and consequent release of the incretin hormone glucagon-like-peptide 1 (GLP-1) from enteroendocrine cell lines. Katsuma et al., supra.

GPR131 agonists also increase serum levels of glucagon-like peptide-1 ("GLP-1") in vivo, and this likely contributes to their ability to improve glucose homeostasis in rodent models. Thomas et al., *Cell Metab.*, 10:167-77 (2009) [PMID:19723493]. Acute improvements in glucose homeostasis due to raising of blood GLP-1 levels by GPR131 agonists may result from increased glucose sensitive insulin secretion (GSIS) from pancreatic beta cells, reduced glucagon secretion from pancreatic alpha cells, and from a delay of gastric emptying, all of which are known effects of GLP-1 in rodents and humans. Drucker, *Gastroenterology*, 122:531-44 (2002). Multiple current and proposed therapeutic agents for diabetes, obesity and metabolic syndrome have their effect via increased stimulation of the receptor for GLP-1 in pancreatic beta cells or other tissues.

Other consequences of GPR131 activation may also contribute to improvements in glucose homeostasis and other metabolic parameters. GPR131 agonists have been described as having the capacity to increase energy expenditure in rodents, and thus may provide an additional means for improving glucose homeostasis via improvements in insulin sensitivity. Watanabe et al., *Nature*, 439:484-9 (2006) [PMID:16400329]. In one study, knock-out mice that lacked GPR131 had a higher body weight and increased fat mass relative to wild type mice when placed on a high fat diet suggesting that reduced signaling through GPR131 could contribute to obesity and insulin resistance Muruyama et al., *J. Endocrinol.*, 191:197-205 (2006).

Additionally, GPR131 is expressed in human CD14+ monocytes and spleen, and may play a role in mediating anti-inflammatory effects of BAs and GPR131 agonists. Agonists of this receptor can increase cAMP levels and reduce phagocytic activity in alveolar macrophages. The latter effect may be due to decreased release of pro-inflammatory cytokines in the presence of GPR131 agonists. Kawamata et al, supra. A similar effect has been observed in the resident macrophages of liver (Kupffer cells) [Keitel et al., *Biochem. Biophys. Res. Commun.*, 372:78-84 (2008). Since adipose tissue inflammations can contribute to an insulin resistant state, it is contemplated that part of the effect of GPR131 agonists to improve glucose homeostasis arises from their capacity to reduce inflammation in adipose tissue.

While certain GPR131 agonists are in early development, none are yet commercially available. Additional agonists of GPR131 for the treatment or prevention of diabetes, metabolic syndrome, liver disease, inflammation, and other diseases and conditions are therefore needed.

SUMMARY

Described herein are compounds of Formula (I), compositions and formulations containing such compounds, and methods of using and making such compounds. These compounds are useful in treating diseases or conditions modulated at least in part by GPR131.

One aspect of the current disclosure relates to compounds of Formula (I)

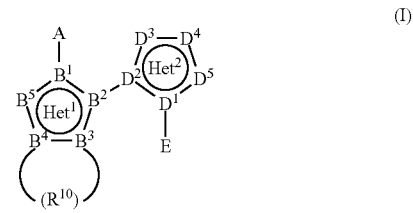

or a derivative thereof, wherein

A is an optionally substituted aryl or heteroaryl;

$B^1$, $B^2$, $B^3$, and $B^4$ are each independently C or N; and $B^5$ is $CR^1$, N, $NR^8$ or O, wherein $B^1$, $B^2$, $B^3$, $B^4$ and $B^5$ together form $Het^1$, which is an optionally substituted 5-membered heteroaryl;

$R^{10}$ is —$(CR^3)_m$—X—$(CR^5)_n$— which, together with $B^3$ and $B^4$, form an optionally substituted aryl or heteroaryl; or —$(CR^3R^4)_m$—X—$(CR^5R^6)_n$— which, together with $B^3$ and $B^4$, form an optionally substituted cycloalkyl or heterocycloalkyl;

$D^1$ and $D^2$ are each independently C or N; and $D^3$, $D^4$, and $D^5$ are each independently $CR^2$, N, $NR^8$, or O, wherein $D^1$, $D^2$, $D^3$, $D^4$, and $D^5$ together form $Het^2$, which is an optionally substituted 5-membered heteroaryl;

E is alkyl, aryl, arylalkyl, cycloalkyl, heteroalkyl, heteroaryl, or heterocycloalkyl, each of which may be optionally substituted;

each $R^1$ is independently H, alkoxy, optionally substituted $C_{1-6}$alkyl, amido, amino, cyano, halo, hydroxyl, sulfonyl, or sulfonamido;

each R² is independently H, alkoxy, optionally substituted C$_{1-6}$alkyl, amido, amino, cyano, halo, hydroxyl, sulfonyl, or sulfonamido;

each R³, R⁴, R⁵, and R⁶ are independently H, alkoxy, amino, an optionally substituted C$_{1-6}$alkyl, cyano, or halo;

n and m are each independently 0, 1, 2, or 3;

X is C(O), N, C(O)NR⁷, NR⁷, O, S, S(O), or S(O)$_2$, or absent;

R⁷ is H, acyl, optionally substituted C$_{1-6}$alkyl, amido, carboxylate, or sulfonyl; and R⁸ is H or optionally substituted C$_{1-6}$alkyl.

One aspect of the current disclosure relates to a compound of Formula (I) with the proviso that, when X is absent, at least one of m and n is not 0.

One aspect of the current disclosure relates to a compound selected from the group consisting of:

2-(2-Chlorophenyl)-3-(1-(4-chlorophenyl)-1H-tetrazol-5-yl)imidazo[1,2-c]pyridine;

2-(2-Chlorophenyl)-3-(4-(4-chlorophenyl)-4H-1,2,4-triazol-3-yl)imidazo[1,2-a]pyridine;

3-(4-Cyclohexyl-4H-1,2,4-triazol-3-yl)-2-(2,5-dichlorophenyl)imidazo[1,2-a]pyridine;

2-(2-Chlorophenyl)-3-(1-(4-chlorophenyl)-1H-1,2,4-triazol-5-yl)imidazo[1,2-a]pyridine;

3-(1-(4-Chlorophenyl)-3-methyl-1H-1,2,4-triazol-5-yl)-2-(2,5-dichlorophenyl)imidazo[1,2-a]pyridine;

3-(4-(4-Chlorophenyl)-5-methyl-4H-1,2,4-triazol-3-yl)-2-(2,5-dichlorophenyl)imidazo[1,2-a]pyridine;

3-(1-(4-Chlorophenyl)-1H-imidazol-2-yl)-2-(2,5-dichlorophenyl)imidazo[1,2-a]pyridine;

3-(1-(4-Chlorophenyl)-1H-imidazol-5-yl)-2-(2,5-dichlorophenyl)imidazo[1,2-a]pyridine;

2-(2,5-Dichlorophenyl)-3-(4-(pyridin-4-yl)-4H-1,2,4-triazol-3-yl)imidazo[1,2-a]pyridine;

2-(2,5-Dichlorophenyl)-3-(4-isopropyl-4H-1,2,4-triazol-3-yl)imidazo[1,2-a]pyridine;

4-(3-(2-(2,5-Dichlorophenyl)imidazo[1,2-a]pyridin-3-yl)-4H-1,2,4-triazol-4-yl)-N,N-dimethylaniline;

4-(4-(3-(2-(2,5-Dichlorophenyl)imidazo[1,2-a]pyridin-3-yl)-4H-1,2,4-triazol-4-yl)phenyl)morpholine;

2-(2,5-Dichlorophenyl)-3-(4-(4-(methylsulfonyl)phenyl)-4H-1,2,4-triazol-3-yl)imidazo[1,2-a]pyridine;

2-(2,5-Dichlorophenyl)-3-(4-(4-(trifluoromethyl)phenyl)-4H-1,2,4-triazol-3-yl)imidazo[1,2-a]pyridine;

5-(3-(2-(2,5-Dichlorophenyl)imidazo[1,2-a]pyridin-3-yl)-4H-1,2,4-triazol-4-yl)-1H-indazole;

4-(3-(2-(2,5-Dichlorophenyl)imidazo[1,2-a]pyridin-3-yl)-4H-1,2,4-triazol-4-yl)benzonitrile;

6-(3-(2-(2,5-Dichlorophenyl)imidazo[1,2-a]pyridin-3-yl)-4H-1,2,4-triazol-4-yl)-1H-indazole;

6-(3-(2-(2,5-Dichlorophenyl)imidazo[1,2-a]pyridin-3-yl)-4H-1,2,4-triazol-4-yl)-1-methyl-1H-benzo[d]imidazole;

5-(3-(2-(2,5-Dichlorophenyl)imidazo[1,2-a]pyridin-3-yl)-4H-1,2,4-triazol-4-yl)benzo[d]thiazole;

5-(3-(2-(2,5-Dichlorophenyl)imidazo[1,2-a]pyridin-3-yl)-4H-1,2,4-triazol-4-yl)-1-methyl-1H-indazole;

6-(3-(2-(2,5-Dichlorophenyl)imidazo[1,2-a]pyridin-3-yl)-4H-1,2,4-triazol-4-yl)-1-methyl-1H-indazole;

5-(3-(2-(2,5-Dichlorophenyl)imidazo[1,2-a]pyridin-3-yl)-4H-1,2,4-triazol-4-yl)-1-methyl-1H-benzo[d]imidazole;

6-(3-(2-(2-Chlorophenyl)imidazo[1,2-a]pyridin-3-yl)-4H-1,2,4-triazol-4-yl)-1H-indazole;

3-(4-(1H-Indazol-6-yl)-4H-1,2,4-triazol-3-yl)-2-(2,5-dichlorophenyl)imidazo[1,2-b]pyridazine;

3-(4-(4-Chlorophenyl)-4H-1,2,4-triazol-3-yl)-2-(4-fluorophenyl)pyrazolo[1,5-a]pyridine;

4-(4-Chlorophenyl)-3-(2-(2,5-dichlorophenyl)imidazo[1,2-a]pyridin-3-yl)-1H-1,2,4-triazol-5(4H)-one;

4-(4-Chlorophenyl)-3-(2-(2,5-dichlorophenyl)imidazo[1,2-a]pyridin-3-yl)-1H-1,2,4-triazole-5(4H)-thione;

3-(4-(4-Chlorophenyl)-5-methoxy-4H-1,2,4-triazol-3-yl)-2-(2,5-dichlorophenyl)imidazo[1,2-a]pyridine;

3-(4-(4-Chlorophenyl)-5-(methylthio)-4H-1,2,4-triazol-3-yl)-2-(2,5-dichlorophenyl)imidazo[1,2-a]pyridine;

2-(2,5-Dichlorophenyl)-3-(4-(4-ethylphenyl)-4H-1,2,4-triazol-3-yl)imidazo[1,2-a]pyridine;

2-(2,5-Dichlorophenyl)-3-(4-(4-isopropylphenyl)-4H-1,2,4-triazol-3-yl)imidazo[1,2-a]pyridine;

3-(4-([1,1'-Biphenyl]-4-yl)-4H-1,2,4-triazol-3-yl)-2-(2,5-dichlorophenyl)imidazo[1,2-a]pyridine;

Ethyl 4-(3-(2-(2,5-dichlorophenyl)imidazo[1,2-a]pyridine-3-yl)-4H-1,2,4-triazol-4-yl)benzoate;

2-(2,5-Dichlorophenyl)-3-(4-(4-fluorophenyl)-4H-1,2,4-triazol-3-yl)imidazo[1,2-a]pyridine;

2-(2,5-Dichlorophenyl)-3-(4-(2-fluorophenyl)-4H-1,2,4-triazol-3-yl)imidazo[1,2-a]pyridine;

2-(2,5-Dichlorophenyl)-3-(4-(3-fluorophenyl)-4H-1,2,4-triazol-3-yl)imidazo[1,2-a]pyridine;

2-(2,5-Dichlorophenyl)-3-(4-(1-methyl-1H-indol-5-yl)-4H-1,2,4-triazol-3-yl)imidazo[1,2-a]pyridine;

2-(2,5-Dichlorophenyl)-3-(4-(4-(3-(trifluoromethyl)-1H-pyrazol-1-yl)phenyl)-4H-1,2,4-triazol-3-yl)imidazo[1,2-a]pyridine;

4-(3-(2-(2,5-Dichlorophenyl)imidazo[1,2-a]pyridine-3-yl)-4H-1,2,4-triazol-4-yl)-3,5-dimethylisoxazole;

N-(4-(3-(2-(2,5-Dichlorophenyl)imidazo[1,2-a]pyridin-3-yl)-4H-1,2,4-triazol-4-yl)phenyl)-N-methylacetamide;

2-(2,5-Dichlorophenyl)-3-(4-(6-methylpyridin-3-yl)-4H-1,2,4-triazol-3-yl)imidazo[1,2-a]pyridine;

6-(3-(2-(2,5-Dichlorophenyl)imidazo[1,2-a]pyridin-3-yl)-4H-1,2,4-triazol-4-yl)quinoline;

N-(2-Chloro-4-(3-(2-(2,5-dichlorophenyl)imidazo[1,2-a]pyridin-3-yl)-4H-1,2,4-triazol-4-yl)phenyl)acetamide;

3-(4-(4-Chlorobenzyl)-4H-1,2,4-triazol-3-yl)-2-(2,5-dichlorophenyl)imidazo[1,2-a]pyridine;

4-(3-(2-(2,5-Dichlorophenyl)imidazo[1,2-a]pyridin-3-yl)-4H-1,2,4-triazol-4-yl)-1H-indazole;

4-(3-(2-(2,5-Dichlorophenyl)imidazo[1,2-a]pyridin-3-yl)-4H-1,2,4-triazol-4-yl)-1-methyl-1H-indazole;

2-(2,5-Dichlorophenyl)-3-(4-(4-(4-methylpiperazin-1-yl)phenyl)-4H-1,2,4-triazol-3-yl)imidazo[1,2-a]pyridine;

4-(3-(2,5-Dichlorophenyl)imidazo[1,2-a]pyridine-3-yl)-4H-1,2,4-triazol-4-yl)-N,N-dimethylbenzamide;

4-(3-(2-(2,5-Dichlorophenyl)imidazo[1,2-a]pyridine-3-yl)-4H-1,2,4-triazol-4-yl)benzoic acid;

2-(2-Chloro-5-fluorophenyl)-3-(1-(4-chlorophenyl)-1H-tetrazol-5-yl)imidazo[1,2-a]pyrimidine;

2-(2-Chloro-5-fluorophenyl)-3-(1-(4-chlorophenyl)-1H-tetrazol-5-yl)-5,6,7,8-tetrahydroimidazo[1,2-a]pyrimidine;

5-(1-(4-Chlorophenyl)-1H-tetrazol-5-yl)-6-(2,5-dichlorophenyl)imidazo[2,1-b]oxazole;

3-(1-(4-Chlorophenyl)-1H-tetrazol-5-yl)-2-(2,5-dichlorophenyl)imidazo[1,2-a]pyridine;

3-(4-(4-Chlorophenyl)-4H-1,2,4-triazol-3-yl)-2-(2,5-dichlorophenyl)imidazo[1,2-a]pyridine;

3-(1-(4-Chlorophenyl)-1H-1,2,4-triazol-5-yl)-2-(2,5-dichlorophenyl)imidazo[1,2-a]pyridine;

3-(1-(4-Chlorophenyl)-1H-tetrazol-5-yl)-2-(2,5-dichlorophenyl)imidazo[1,2-b]pyridazine;

3-(1-(4-Chlorophenyl)-1H-tetrazol-5-yl)-2-(2,5-dichlorophenyl)imidazo[1,2-a]pyrazine;

2-(2-Chlorophenyl)-3-(1-(4-chlorophenyl)-1H-imidazol-2-yl)imidazo[1,2-a]pyridine;

3-(1-(4-Chlorophenyl)-1H-tetrazol-5-yl)-2-(2,5-dichlorophenyl)imidazo[1,2-a]pyrimidine;
3-(1-(4-Chlorophenyl)-1H-tetrazol-5-yl)-2-(2,5-dichlorophenyl)-5,6,7,8-tetrahydroimidazo[1,2-a]pyridine;
3-(1-(4-Chlorophenyl)-1H-imidazol-2-yl)-2-(2,5-dichlorophenyl)-5,6,7,8-tetrahydroimidazo[1,2-a]pyridine;
3-(1-(4-Chlorophenyl)-1H-imidazol-2-yl)-2-(2,5-dichlorophenyl)imidazo[1,2-b]pyridazine;
2-(2,5-Dichlorophenyl)-3-(1-(4-(trifluoromethyl)phenyl)-1H-tetrazol-5-yl)imidazo[1,2-a]pyridine;
2-(2,5-Dichlorophenyl)-3-(1-(4-(trifluoromethyl)phenyl)-1H-tetrazol-5-yl)imidazo[1,2-b]pyridazine;
2-(2,5-Dichlorophenyl)-3-(1-(4-(trifluoromethyl)phenyl)-1H-imidazol-2-yl)imidazo[1,2-a]pyridine;
2-(2,5-Dichlorophenyl)-3-(1-(4-(trifluoromethyl)phenyl)-1H-imidazol-2-yl)imidazo[1,2-b]pyridazine;
4-(5-(2-(2,5-Dichlorophenyl)imidazo[1,2-a]pyridin-3-yl)-1H-tetrazol-1-yl)benzonitrile;
4-(2-(2-(2,5-Dichlorophenyl)imidazo[1,2-a]pyridin-3-yl)-1H-imidazol-1-yl)benzonitrile;
6-(3-(2-(3-Chlorophenyl)imidazo[1,2-a]pyridin-3-yl)-4H-1,2,4-triazol-4-yl)-1H-indazole;
3-(4-(4-chloro-3-(trifluoromethyl)phenyl)-4H-1,2,4-triazol-3-yl)-2-(2,5-dichlorophenyl)imidazo[1,2-a]pyridine;
2-(2,5-dichlorophenyl)-3-(4-(1-methyl-1H-indol-6-yl)-4H-1,2,4-triazol-3-yl)imidazo[1,2-a]pyridine;
6-chloro-3-(3-(2-(2,5-dichlorophenyl)imidazo[1,2-a]pyridin-3-yl)-4H-1,2,4-triazol-4-yl)-1-methyl-1H-indazole;
2-(2,5-dichlorophenyl)-3-(4-(5-methylpyridin-2-yl)-4H-1,2,4-triazol-3-yl)imidazo[1,2-a]pyridine;
2-(2,5-dichlorophenyl)-3-(4-(pyrimidin-5-yl)-4H-1,2,4-triazol-3-yl)imidazo[1,2-a]pyridine;
2-(2,5-dichlorophenyl)-3-(4-(4-(pyrrolidin-1-yl)phenyl)-4H-1,2,4-triazol-3-yl)imidazo[1,2-a]pyridine;
4-(2-(2-(2,5-dichlorophenyl)imidazo[1,2-b]pyridazin-3-yl)-1H-imidazol-1-yl)benzonitrile;
3-(5-(4-chlorophenyl)-4H-1,2,4-triazol-3-yl)-2-(2,5-dichlorophenyl)imidazo[1,2-a]pyridine;
2-(2,5-dichlorophenyl)-3-(4-(1-methylindolin-5-yl)-4H-1,2,4-triazol-3-yl)imidazo[1,2-a]pyridine;
5-(3-(2-(2,5-dichlorophenyl)imidazo[1,2-a]pyridin-3-yl)-4H-1,2,4-triazol-4-yl)-N,N-dimethylpyridin-2-amine;
5-(3-(2-(2,5-dichlorophenyl)imidazo[1,2-a]pyridin-3-yl)-4H-1,2,4-triazol-4-yl)picolinonitrile;
3-(4-(benzofuran-5-yl)-4H-1,2,4-triazol-3-yl)-2-(2,5-dichlorophenyl)imidazo[1,2-a]pyridine;
2-(2,5-dichlorophenyl)-3-(4-(2,3-dihydrobenzofuran-5-yl)-4H-1,2,4-triazol-3-yl)imidazo[1,2-a]pyridine;
4-(3-(2-(4-chlorophenyl)pyrazolo[1,5-a]pyridin-3-yl)-4H-1,2,4-triazol-4-yl)benzonitrile;
3-(3-(4-chlorophenyl)-4H-1,2,4-triazol-4-yl)-2-(2,5-dichlorophenyl)imidazo[1,2-a]pyridine;
4-(3-(2-(4-chlorophenyl)pyrazolo[1,5-b]pyridazin-3-yl)-4H-1,2,4-triazol-4-yl)benzonitrile;
3-(4-(7-chloro-2-methylbenzofuran-5-yl)-4H-1,2,4-triazol-3-yl)-2-(2,5-dichlorophenyl)imidazo[1,2-a]pyridine;
2-(4-chlorophenyl)-3-(4-(4-chlorophenyl)-4H-1,2,4-triazol-3-yl)pyrazolo[1,5-b]pyridazine;
2-(2-chlorophenyl)-3-(4-(4-chlorophenyl)-4H-1,2,4-triazol-3-yl)imidazo[1,2-b]pyridazine;
3-(4-(4-chlorophenyl)-4H-1,2,4-triazol-3-yl)-2-(2-fluoro-5-methylphenyl)imidazo[1,2-a]pyridine;
4-(3-(2-(2-chlorophenyl)imidazo[1,2-b]pyridazin-3-yl)-4H-1,2,4-triazol-4-yl)benzonitrile;
3-(4-(4-chlorophenyl)-4H-1,2,4-triazol-3-yl)-2-(2,5-dimethylphenyl)imidazo[1,2-a]pyridine;
2-(2,5-dichlorophenyl)-3-(4-(2-methylbenzofuran-5-yl)-4H-1,2,4-triazol-3-yl)imidazo[1,2-a]pyridine;
3-(4-(4-chlorophenyl)-4H-1,2,4-triazol-3-yl)-2-(2,5-dichlorophenyl)-4,5,6,7-tetrahydro-2H-indazole;
4-(3-(2-(2,5-dichlorophenyl)-4,5,6,7-tetrahydro-2H-indazol-3-yl)-4H-1,2,4-triazol-4-yl)benzonitrile; and
4-(3-(2-(2,5-dichlorophenyl)pyrazolo[1,5-b]pyridazin-3-yl)-4H-1,2,4-triazol-4-yl)benzonitrile,
or a salt, racemate, or a tautomer thereof.

One aspect of the current disclosure relates to a pharmaceutical composition comprising an amount of a compound of Formula (I) effective to modulate GPR131, and a pharmaceutically acceptable carrier.

One aspect of the current disclosure relates to a method of treating a subject suffering from or at risk of a disease or condition for which GPR131 modulation provides a therapeutic benefit, comprising administering to the subject an effective amount of a compound of a compound of Formula (I).

DETAILED DESCRIPTION

Definitions

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

A dash at the front or end of a chemical group is a matter of convenience; chemical groups may be depicted with or without one or more dashes without losing their ordinary meaning. A wavy line drawn through a line in a structural formula indicates a point of attachment of a group. Unless chemically or structurally required, no directionality is indicated or implied by the order in which a chemical group is written. For instance, the group "—SO$_2$CH$_2$—" is equivalent to "—CH$_2$SO$_2$—" and both may be connected in either direction. The prefix "C$_{u-v}$" indicates that the following group has from u to v carbon atom. For example, "C$_{1-6}$alkyl" indicates that the alkyl group has from 1 to 6 carbon atoms.

Also, certain commonly used alternative chemical names may or may not be used. For example, a divalent group such as a divalent "alkyl" group, or a divalent "aryl" group, etc., may also be referred to as an "alkylene" group or an "alkylenyl" group, or an "arylene" group, respectively.

"Alkyl" refers to any aliphatic hydrocarbon group, i.e. any linear, branched or cyclic nonaromatic hydrocarbon group or an isomer or combination thereof. As used herein, the term "alkyl" includes terms used in the art to describe saturated and unsaturated aliphatic hydrocarbon groups with one or more points of attachment, including alkenyl (an aliphatic group containing at least one carbon-carbon double bond), alkylene (a divalent aliphatic group), alkynyl (an aliphatic group containing at least one carbon-carbon triple bond), cycloalkyl (a cyclic aliphatic group), alkylcycloalkyl (a linear or branched aliphatic group attached to a cyclic aliphatic group), and the like. Alkyl groups include, but are not limited to, methyl; ethyl; propyls such as propan-1-yl, propan-2-yl (iso-propyl), cyclopropan-1-yl, etc.; butyls such as butan-1-yl, butan-2-yl (sec-butyl), 2-methyl-propan-1-yl (iso-butyl), 2-methyl-propan-2-yl (t-butyl), cyclobutan-1-yl; pentyls; hexyls; octyls; dodecyls; octadecyls; cyclopentyl, cyclohexyl, methylcyclohexyl, and the like. An alkyl group comprises from 1 to about 10 carbon atoms, e.g., from 1 to 6 carbon atoms.

"Alkenyl" is a subset of "alkyl" and refers to an aliphatic group containing at least one carbon-carbon double bond and having from 2 to about 10 carbon atoms, e.g., from 2 to 6 carbon atoms or 2 to 4 carbon atoms and having at least one site of vinyl unsaturation (>C=C<). Alkenyl groups include ethenyl, propenyl, 1,3-butadienyl, and the like.

"Alkynyl" is a subset of "alkyl" and refers to an aliphatic group containing at least one carbon-carbon triple bond. The term "alkynyl" is also meant to include those groups having one triple bond and one double bond.

"Alkoxy" refers to the group —O-alkyl, wherein the alkyl group may be optionally substituted. Alkoxy includes, by way of example, methoxy, ethoxy, n-propoxy, isopropoxy, n-butoxy, t-butoxy, sec-butoxy, and n-pentoxy.

"Acyl" refers to a group —C(=O)R, where R is hydrogen, alkyl, cycloalkyl, cycloheteroalkyl, aryl, arylalkyl, heteroalkyl, heteroaryl or heteroarylalkyl as defined herein, each of which may be optionally substituted, as defined herein. Representative examples include, but are not limited to formyl, acetyl, cyclohexylcarbonyl, cyclohexylmethylcarbonyl, benzoyl, benzyloxycarbonyl and the like.

"Amino" refers to the group —NR$^y$R$^z$ wherein R$^y$ and R$^z$ are independently selected from the group consisting of hydrogen, alkyl, aryl, heteroaryl (each of which may be optionally substituted), and where R$^y$ and R$^z$ are optionally joined together with the nitrogen bound thereto to form an optionally substituted heterocycloalkyl.

"Amidino" refers to the group —C(=NR$^x$)NR$^y$R$^z$ where R$^x$, R$^y$, and R$^z$ are independently selected from the group consisting of hydrogen, alkyl, aryl, heteroaryl (each of which may be optionally substituted), and where R$^y$ and R$^z$ are optionally joined together with the nitrogen bound thereto to form an optionally substituted heterocycloalkyl.

"Amido" refers to both C-amido and N-amido, wherein C-amido refers to the group —C(=O)NR$^y$R$^z$ wherein R$^y$ and R$^z$ are as defined for the amino group, and wherein N-amido refers to the group —N(R$^x$)C(=O)R$^y$ wherein R$^x$ and R$^y$ are independently selected from the group consisting of hydrogen, alkyl, aryl, heteroaryl (each of which may be optionally substituted).

"Aryl" refers to a group with one or more aromatic rings. It may be a single aromatic ring or multiple aromatic rings which are fused together, linked covalently, or linked via one or more such as a methylene or ethylene moiety. Aryl groups include, but are not limited to, those groups derived from acenaphthylene, anthracene, azulene, benzene, biphenyl, chrysene, cyclopentadienyl anion, diphenylmethyl, fluoranthene, fluorene, indane, indene, naphthalene, perylene, phenalene, phenanthrene, pyrene, triphenylene, and the like. An aryl group comprises from 5 to about 20 carbon atoms, e.g., from 6 to 20 carbon atoms, e.g. from 6 to 10 carbon atoms.

"Arylalkyl" (also "aralkyl") refers to an aryl group attached to an alkyl group. Arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl may be used. An arylalkyl group comprises from 6 to about 30 carbon atoms, e.g. the alkyl group can comprise from 1 to about 10 carbon atoms and the aryl group can comprise from 5 to about 20 carbon atoms.

"Aryloxy" refers to the group —O-aryl, including by way of example, phenoxy and naphthoxy.

"Azido" refers to the group —N$_3$.

"Carbonyl" refers to the divalent group —C(O)— which is equivalent to —C(=O)—.

"Carboxyl" or "carboxy" refers to —COOH or salts thereof.

"Carboxylate" refers to the group —C(=O)OR$^z$ where R$^z$ is hydrogen, alkyl, aryl, heteroaryl (each of which may be optionally substituted).

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)β-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Cyano" or "carbonitrile" refers to the group —CN.

"Cycloalkyl" is a subset of "alkyl" and refers to a saturated or partially saturated cyclic group of from 3 to about 10 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g., 5,6,7,8,-tetrahydronaphthalene-5-yl). The term "cycloalkyl" includes cycloalkenyl groups. Examples of cycloalkyl groups include, for instance, adamantyl, cyclopropyl, cyclobutyl, cyclopentyl, cyclooctyl, and cyclohexenyl.

"Derivative" refers to salts, prodrugs, racemates, and tautomers. Derivatives include pharmaceutically acceptable derivatives, including pharmaceutically acceptable salts and prodrugs.

"Guanidino" refers to the group —NHC(=NH)NH$_2$.

"Halo" or "halogen" refers to fluoro, chloro, bromo and iodo.

"Haloalkyl" refers to substitution of alkyl groups with 1 to 5 or, in some embodiments, 1 to 3 halo groups, e.g., —CH$_2$Cl, —CH$_2$F, —CH$_2$Br, —CFClBr, —CH$_2$CH$_2$Cl, —CH$_2$CH$_2$F, —CF$_3$, —CH$_2$CF$_3$, —CH$_2$CCl$_3$, and the like, and further includes those alkyl groups such as perfluoroalkyl in which all hydrogen atoms are replaced by fluorine atoms.

"Haloaryl" refers to aryl groups with one or more halo or halogen substituents. For example, haloaryl groups include phenyl groups in which from 1 to 5 hydrogens are replaced with a halogen. Haloaryl groups include, for example, fluorophenyl, difluorophenyl, trifluorophenyl, chlorophenyl, clorofluorophenyl, and the like.

"Heteroalkyl" refers to an alkyl group in which one or more of the carbon atoms (and any associated hydrogen atoms) are each independently replaced with the same or different a heteroatomic group. Heteroatoms include, but are not limited to, N, P, O, S, etc. Heteroatomic groups include, but are not limited to, —NR—, —O—, —S—, —PH—, —P(O)$_2$—, —S(O)—, —S(O)$_2$—, and the like, where R is H, alkyl, aryl, cycloalkyl, heteroalkyl, heteroaryl or cycloheteroalkyl. The term "heteroalkyl" includes heterocycloalkyl (a cyclic heteroalkyl group), alkyl-heterocycloalkyl (a linear or branched aliphatic group attached to a cyclic heteroalkyl group), and the like. Heteroalkyl groups include, but are not limited to, —OCH$_3$, —CH$_2$OCH$_3$, —SCH$_3$, —CH$_2$SCH$_3$, —NRCH$_3$, —CH$_2$NRCH$_3$, and the like, where R is defined above. A heteroalkyl group comprises from 1 to about 10 carbon and hetero atoms, e.g., from 1 to 6 carbon and hetero atoms.

"Heteroaryl" refers to an aryl group in which one or more of the carbon atoms (and any associated hydrogen atoms) are each independently replaced with the same or different heteroatomic groups, as defined above. Heteroaryl groups include, but are not limited to, groups derived from acridine, carbazole, carboline, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. A heteroaryl group comprises from 5 to about 20 atoms, e.g., from 5 to 20 atoms, e.g. from 5 to 10 atoms.

"Heterocycloalkyl" is a subset of "heteroalkyl" and refers to a saturated or unsaturated cycloalkyl group in which one or more carbon atoms (and any associated hydrogen atoms) are independently replaced with the same or different heteroatom. Heteroatoms include, but are not limited to, N, P, O, S, etc. A heterocycloalkyl group may also contain a charged heteroatom or group, e.g., a quaternized ammonium group such as —N$^+$(R)$_2$— wherein R is alkyl, e.g., methyl, ethyl, etc. Heterocycloalkyl groups include, but are not limited to, groups derived from epoxides, imidazolidine, morpholine, piperazine, piperidine, pyrazolidine, piperidine, pyrrolidine, quinuclidine, N-bromopyrrolidine, N-bromopiperidine, N-chloropyrrolidine, N-chloropiperidine, an N,N-dialkylpyrrolidinium, such as N,N-dimethylpyrrolidinium, a N,N-dialkylpiperidinium such as N,N-dimethylpiperidium, and the like. The heterocycloalkyl group comprises from 3 to about 10 carbon and hetero atoms in the ring.

"Hydrazino" refers to the group —NHNH$_2$.

"Hydroxy" or "hydroxyl" refers to the group —OH.

"Imino" refers to the group —C(═NR)— wherein R can be hydrogen or alkyl, aryl, heteroalkyl, or heteroaryl, each of which may be optionally substituted.

"Nitro" refers to the group —NO$_2$.

The terms "optional" or "optionally" mean that the subsequently described event or circumstance may but need not occur, and that the description includes instances where the event or circumstance occurs and instances in which it does not.

"Oxide" refers to products resulting from the oxidation of one or more heteroatoms. Examples include N-oxides, sulfoxides, and sulfones.

"Oxo" refers to the atom (═O).

"Racemates" refers to a mixture of enantiomers.

"Spirocycloalkyl" refers to a 3- to 10-member cyclic substituent formed by replacement of two hydrogen atoms at a common carbon atom with an alkylene group having 2 to 9 carbon atoms, as exemplified by the following structure wherein the methylene group shown below attached to bonds marked with wavy lines is substituted with a spirocycloalkyl group:

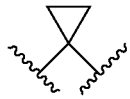

"Stereoisomer" or "stereoisomers" refer to compounds that differ in the chirality of one or more stereocenters. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of *Advanced Organic Chemistry,* 4th ed., J. March, John Wiley and Sons, New York, 1992).

"Substituted" (as in, e.g., "substituted alkyl") refers to a group wherein one or more hydrogens have been independently replaced with one or more substituents including, but not limited to, alkyl, alkenyl, alkynyl, alkoxy, acyl, amino, amidino, aryl, azido, carbamoyl, carboxyl, carboxyl ester, cyano, cycloalkyl, guanidino, halo, heteroalkyl, heteroaryl, heterocycloalkyl, hydroxy, hydrazino, hydroxyl, imino, oxo, nitro, sulfonamide, sulfonic acid, thiocyanate, thiol, thione, or a combination thereof. Polymers arrived at by defining substituents with further substituents to themselves ad infinitum (e.g., substituted aryl having a substituted aryl group as a substituent which is itself substituted with a substituted aryl group, which is further substituted by a substituted aryl group, etc.) are not intended for inclusion herein. Unless otherwise noted, the maximum number of such substitutions in compounds described herein is three. For example, serial substitutions of substituted aryl groups with two other substituted aryl groups are limited to -substituted aryl-(substituted aryl)-substituted aryl. Similarly, it is understood that the above definitions are not intended to include impermissible substitution patterns (e.g., methyl substituted with 5 fluoro groups or heteroaryl groups having two adjacent oxygen ring atoms). Such impermissible substitution patterns are well known to the skilled artisan.

"Sulfonamide" and "sulfonamido" refer to S-sulfonamide (or S-sulfonamido) and N-sulfonamide (or N-sulfonamido), wherein S-sulfonamide refers to the group —S(═O)$_2$NR$^y$R$^z$ where R$^y$ and R$^z$ are as defined for the amino group, and wherein N-sulfonamide refers to the group —N(R$^x$)S(═O)$_2$R$^y$ wherein R$^x$ and R$^y$ are independently selected from the group consisting of hydrogen, alkyl, aryl, heteroaryl (each of which may be optionally substituted).

"Sulfonyl" refers to the group —S(═O)$_2$R$^x$ where R$^x$ is selected from the group consisting of hydrogen, alkyl, aryl, heteroaryl, each of which may be optionally substituted.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring ═N-moiety such as pyrazoles, imidazoles, benzimidazoles, triazoles, and tetrazoles.

"Thiocyanate" refers to the group —SCN.

"Thiol" refers to the group —SH.

"Thione" refers to the atom (═S).

"Pharmaceutically acceptable" refers to that which is useful in preparing a pharmaceutical composition that is generally safe, non-toxic, and neither biologically nor otherwise undesirable, and includes that which is acceptable for veterinary or human pharmaceutical use.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-naphthalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., *J. Pharma Sci.*, 66(1), 1-19 (1977), and Remington: *The Science and Practice of Pharmacy*, R. Hendrickson, ed., 21st edition, Lippincott, Williams & Wilkins, Philadelphia, Pa., (2005), at p. 732, Table 38-5, each of which are hereby incorporated by reference herein.

"Prodrug" refers to any derivative of a compound of the embodiments that is capable of directly or indirectly providing a compound of the embodiments or an active metabolite or residue thereof when administered to a subject. Prodrugs of a compound are prepared by modifying functional groups present in the compound in such a way that the modifications may be cleaved in vivo to release the parent compound, or an active metabolite. For example, prodrugs include compounds wherein a hydroxy, amino, or sulfhydryl group in a compound is bonded to any group that may be cleaved in vivo to regenerate the free hydroxyl, amino, or sulfhydryl group, respectively. Particularly favored derivatives and prodrugs are those that increase the bioavailability of the compounds of the embodiments when such compounds are administered to a subject (e.g., by allowing an orally administered compound to be more readily absorbed into the blood) or which enhance delivery of the parent compound to a biological compartment (e.g., the brain or lymphatic system) relative to the parent species. Prodrugs include ester, amide, and carbamate (e.g., N,N-dimethylaminocarbonyl) forms of hydroxy functional groups of compounds. Examples of ester prodrugs include formate, acetate, propionate, butyrate, acrylate, and ethylsuccinate derivatives. Further examples of prodrugs can be found in J. Rautio et al. *Prodrugs: design and clinical applications*, Nat. Rev. Drug Discov., 7, 255-270 (2008); Edward B. Roche, ed., *Bioreversible Carriers in Drug Design*, American Pharmaceutical Association and Pergamon Press, (1987); and T. Higuchi and V. Stella, *Pro-drugs as Novel Delivery Systems*, Vol. 14 of the A.C.S. Symposium Series (1975), each of which are hereby incorporated by reference herein.

The following abbreviations may also be used: AcOH: acetic acid; nBuLi: n-butyllithium; $Cs_2CO_3$: cesium carbonate; $CH_2Cl_2$ or DCM: dichloromethane; $CH_3MgI$: methyl magnesium iodide; $CuCl_2$: copper chloride; DAST: (diethylamino)sulfur trifluoride; DEAD: diethyl azodicarboxylate; DIBAL: diisobutylaluminum hydride; DIPEA: diisopropylethylamine; DMF: dimethylformamide; DMSO: dimethyl sulfoxide; $Et_3N$: triethylamine; EtOAc: ethyl acetate; EtOH: ethanol; g: gram(s); h: hour; $H_2$: hydrogen; HBr: hydrogen bromide; HCl: hydrogen chloride; $H_2O$: water; $H_2O_2$: hydrogen peroxide; HPLC: high performance liquid chromatography; KCN: potassium cyanide; LHMDS: lithium hexamethyldisilazide; $LiAlH_4$: lithium aluminum hydride; LiOH: lithium hydroxide; M: molar; MeCN: acetonitrile; MeI methyl iodide; MeOH: methanol; $MgSO_4$: magnesium sulfate; $MgCO_3$: magnesium carbonate; mg: milligram; MsCl: mesyl chloride; mmol: millimoles mL: milliliter; sodium hydrogen sulfite; mCPBA: meta-chloroperoxybenzoic acid; N: normality; $N_2$: nitrogen; $Na_2CO_3$: sodium carbonate; $NaHCO_3$: sodium bicarbonate; $NaNO_2$: sodium nitrite; NaOH: sodium hydroxide; $Na_2S_2O_3$: sodium bisulfate; $Na_2SO_4$: sodium sulfate; NBS: N-bromosuccinimide; $NH_4Cl$: ammonium chloride; $NH_4OAc$: ammonium acetate; NMR: nuclear magnetic resonance; Pd/C: palladium on carbon; $PPh_3$: triphenyl phosphine; iPrOH: isopropyl alcohol; $SOCl_2$: thionyl chloride; THF: tetrahydrofuran; TLC: thin layer chromatography; μL: microliter.

With reference to the various methods described herein, the following terms are also used.

"Activate" and "activation" refer to increasing the cellular function of a receptor, for example GPR131.

"Agonist" refers to a compound or moiety that binds to a receptor and triggers a response in a cell or enhances GTP binding to membranes. An agonist may mimic (wholly or partially) the cell response to an endogenous ligand, e.g. a hormone, and produce a physiological response similar to that produced by the endogenous ligand.

"Antihyperlipidemic" refers to the lowering of excessive lipid concentrations in blood to desired levels.

"Atherosclerosis" encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease".

"Beta cell" refers to cells found in the islet of Langerhans that secrete insulin, amylin, and other hormones.

"cAMP," "cyclic AMP" and "cyclic adenosine monophosphate" refer to an intracellular signaling molecule involved in many biological processes, including glucose and lipid metabolism.

"Diabetes" and "diabetes mellitus" refer to a disease or condition that is generally characterized by metabolic defects in production and utilization of glucose that result in the failure to maintain appropriate blood sugar levels in the body. The result of these defects is elevated blood glucose, referred to as "hyperglycemia." Two major forms of diabetes are type 1 diabetes and type 2 diabetes. Type 1 diabetes is generally the result of an absolute deficiency of insulin, the hormone that regulates glucose utilization. Type 2 diabetes often occurs in the face of normal or even elevated levels of insulin and can result from the inability of tissues to respond appropriately to insulin. Most type 2 diabetics are insulin resistant and have a relative deficiency of insulin, in that insulin secretion cannot compensate for the resistance of peripheral tissues to respond to insulin. In addition, many type 2 diabetics are obese. Other types of disorders of glucose homeostasis include impaired glucose tolerance, which is a metabolic stage intermediate between normal glucose homeostasis and diabetes, and gestational diabetes mellitus, which is glucose intolerance in pregnancy in females (e.g. women) with no previous history of type 1 or type 2 diabetes. The guidelines for diagnosis of type 2 diabetes, impaired glucose tolerance, and gestational diabetes have been outlined by the American Diabetes Association (see, e.g., The Expert Committee on the Diagnosis and Classification of Diabetes Mellitus, *Diabetes Care*, (1999) Vol. 2 (Suppl 1):S5-19). As used herein, "diabetes" and "diabetes mellitus" also include "prediabetes," "borderline diabetes," "impaired glucose tolerance," and "impaired fasting glucose," which refer to states in which some but not all of the diagnostic criteria for diabetes are met, e.g. where blood glucose levels are higher than normal but not yet high enough to result in a diagnosis of diabetes.

"Dyslipidemia" refers to abnormal levels of lipoproteins in blood plasma including both depressed and/or elevated levels of lipoproteins (e.g., elevated levels of LDL and/or VLDL, and depressed levels of HDL), including hyperlipidemia. Because cholesterol and TGs are water insoluble, they must be packaged in special molecular complexes known as "lipoproteins" in order to be transported in the plasma. Lipoproteins can accumulate in the plasma due to overproduction and/or deficient removal. There are at least five distinct lipoproteins differing in size, composition, density, and function. In the cells of the small intestine, dietary lipids are packaged into large lipoprotein complexes called "chylomicrons", which have a high TG and low-cholesterol content. In the liver, TG and cholesterol esters are packaged and released into plasma as TG-rich lipoprotein called very low density lipoprotein ("VLDL"), whose primary function is the endogenous transport of TGs made in the liver or released by adipose tissue. Through enzymatic action, VLDL can be either reduced and taken up by the liver, or transformed into intermediate density lipoprotein ("IDL"). IDL, is in turn, either taken up by the liver, or is further modified to form low density lipoprotein ("LDL"). LDL is either taken up and broken down by the liver, or is taken up by extrahepatic tissue. High density lipoprotein ("HDL") helps remove cholesterol from peripheral tissues in a process called reverse cholesterol transport.

"Effective amount" or "therapeutically effective amount" means the amount of a compound described herein that may be effective to elicit the desired biological or medical response. These terms include the amount of a compound that, when administered to a subject for treating a disease, is sufficient to effect such treatment for the disease. The effective amount will vary depending on the compound, the disease and its severity and the age, weight, etc., of the subject to be treated.

"Endocrine cell" refers to cells that secrete hormones into the blood stream. Endocrine cells are found various glands and organ systems of the body including the pancreas, intestines, and other organs.

"GIP" or "gastric inhibitory peptide" or "glucose dependent insulinotropic polypeptide" refers to a peptide hormone produced primarily by K cells. GIP stimulates insulin secretion. GIP also has significant effects on lipid metabolism.

"GLP-1" or "glucagon-like peptide-1" is a peptide hormone primarily produced by L cells. GLP-1 increases insulin secretion, decreases glucagon secretion, increases beta cell mass and insulin gene expression, inhibits acid secretion and gastric emptying in the stomach, and decreases food intake by increasing satiety.

"GLP-2" or "glucagon-like peptide-2" is a peptide hormone primarily produced by L cells. GLP-2 stimulates mucosal growth, increases intestinal nutrient absorption, inhibits gastric emptying, inhibits gastric acid secretion, stimulates intestinal blood flow and relaxes intestinal smooth muscle.

"Hyperlipidemia" includes, but is not limited to (1) Familial Hyperchylomicronemia, a rare genetic disorder that causes a deficiency in an enzyme, LP lipase, that breaks down fat molecules. The LP lipase deficiency can cause the accumulation of large quantities of fat or lipoproteins in the blood; (2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma; (3) Familial Combined Hyperlipidemia, also known as multiple lipoprotein-type hyperlipidemia is an inherited disorder where subjects and their affected first-degree relatives can at various times manifest high cholesterol and high triglycerides. Levels of HDL cholesterol are often moderately decreased; (4) Familial Defective Apolipoprotein B-100 is a relatively common autosomal dominant genetic abnormality. The defect is caused by a single nucleotide mutation that produces a substitution of glutamine for arginine, which can cause reduced affinity of LDL particles for the LDL receptor. Consequently, this can cause high plasma LDL and total cholesterol levels; (5) Familial Dysbetaliproteinemia, also referred to as type 3 hyperlipoproteinemia, is an uncommon inherited disorder resulting in moderate to severe elevations of serum TG and cholesterol levels with abnormal apolipoprotein E function. HDL levels are usually normal; and (6) Familial Hypertriglyceridemia, is a common inherited disorder in which the concentration of plasma VLDL is elevated. This can cause mild to moderately elevated TG levels (and usually not cholesterol levels) and can often be associated with low plasma HDL levels. Risk factors for hyperlipidemia include, but are not limited to, the following: (1) disease risk factors, such as a history of type 1 diabetes, type 2 diabetes, Cushing's syndrome, hypothyroidism and certain types of renal failure; (2) drug risk factors, which include, birth control pills; hormones, such as estrogen, and corticosteroids; certain diuretics; and various β-blockers; (3) dietary risk factors include dietary fat intake per total calories greater than 40%; saturated fat intake per total calories greater than 10%; cholesterol intake greater than 300 mg per day; habitual and excessive alcohol use; and obesity.

"Incretin" refers to a group of hormones that increases insulin secretion in response to food intake. Incretins include GLP-1 and GIP.

"Insulin resistance" refers generally to a disorder of glucose metabolism associated with diabetes. More specifically, insulin resistance can be defined as the diminished ability of insulin to exert its biological action across a broad range of concentrations producing less than the expected biologic effect (see, e.g., Reaven G M, *J. Basic & Clin. Phys. & Pharm.* (1998) 9:387-406 and Flie J, *Ann. Rev. Med.* (1983) 34:145-60). Insulin resistant subjects have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, impaired glucose tolerance, gestational diabetes, metabolic syndrome, hypertension, obesity, atherosclerosis and a variety of other disorders. Eventually, the insulin resistant subjects can progress to a point where a diabetic state is reached.

"Insulin" refers to a polypeptide hormone that regulates glucose metabolism. Insulin binds to insulin receptors in insulin sensitive cells and mediates glucose uptake. Insulin is used to treat type 1 diabetes and may be used to treat type 2 diabetes.

"Islet" or "islet of Langerhans" refers to endocrine cells of the pancreas that are grouped together in islets and secrete insulin and other hormones.

"K cell" refers to gut endocrine cells that produce GIP.

"L cell" refers to gut endocrine cells that produce GLP-1.

"Liver disease" refers to various diseases and disorders of the liver including nonalcoholic steatohepatitis, nonalcoholic fatty liver disease, chronic viral hepatitis, alcoholic liver disease, drug induced hepatitis, hemochromatosis, primary biliary cirrhosis, primary sclerosing cholangitis, portal hypertension, bile desaturation, Gaucher's disease, Wilson's disease, .alpha.1-antitrypsin deficiency, total parenteral nutrition (TPN), cholelithiasis, TPN-associated cholestosis and sepsis.

"Metabolic syndrome" refers to various metabolic abnormalities including obesity, insulin resistance, glucose intolerance, diabetes (both type 1 and type 2), hypertension and dyslipidemia.

"Modulate" and "modulating" refer to the treating, prevention, suppression, activation, enhancement, or induction of a function or condition. For example, compounds can modulate type 2 diabetes by increasing insulin in a human, thereby suppressing hyperglycemia. Compounds can also modulate GPR131 by acting, for example, as GPR131 agonists.

"Obese" and "obesity" refer to an excess of body fat. As an exemplary guideline, the World Health Organization describes obesity as a body mass index ("BMI") greater than 27.8 kg/m$^2$ for men and 27.3 kg/m$^2$ for women (BMI is weight (kg)/height (m$^2$)). Obesity is linked to a variety of medical conditions including diabetes and hyperlipidemia. Obesity is also a known risk factor for the development of type 2 diabetes (see, e.g., Barrett-Conner E, *Epidemol. Rev.* (1989) 11:172-181; and Knowler, et al., *Am. J. Clin. Nutr.* (1991) 53:1543-1551).

"Pancreas" refers to a gland organ in the digestive and endocrine system of vertebrates, including mammals. The pancreas secretes both digestive enzymes and hormones such as insulin, GLP-1 and GIP as well as other hormones.

"Partial agonist" refers to a compound or moiety that, when exposed to a receptor, triggers a response in a cell to a lesser degree or extent than does an agonist, or enhances GTP binding to membranes to a lesser degree or extent than does an agonist.

"PYY" or "peptide YY" is a peptide hormone primarily produced by L cells. PYY increases satiety, reduces food intake, inhibits gastric emptying and acid secretion and promotes weight loss.

"Polyuria" refers to the passage of a large volume of urine during a given period.

"Polydipsia" refers to chronic or excessive thirst.

"Polyphagia" refers to excessive eating.

"Subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, rabbits, dogs, and monkeys), and the like.

"Symptoms" of diabetes, include, but are not limited to, polyuria, polydipsia, polyphagia, extreme hunger, unusual weight loss, extreme fatigue and irritability, increased susceptibility to certain infections (especially fungal and staphylococcal infections), blurred vision, nausea, cuts or bruises that are slow to heal, tingling or numbness in the hand or feet, recurring skin, gum, or bladder infections, and ketoacidosis (enhanced production of ketone bodies in the blood).

"Treating" and "treatment" of a disease include (1) preventing or reducing the risk of developing the disease, i.e., causing the clinical symptoms of the disease not to develop in a subject that may be exposed to or predisposed to the disease but does not yet experience or display symptoms of the disease; (2) inhibiting the disease, i.e., arresting or reducing the development of the disease or its clinical symptoms; and (3) relieving the disease, i.e., causing regression of the disease or its clinical symptoms.

"Triglyceride(s)" ("TGs"), as used herein, incorporates its common usage. Triglycerides consist of three fatty acid molecules esterified to a glycerol molecule. Triglycerides serve to store fatty acids that are used by muscle cells for energy production or are taken up and stored in adipose tissue.

Also provided herein are pharmaceutical compositions comprising a compound of Formula (I) and a pharmaceutically acceptable carrier.

Methods of treating a disease or condition selected from the group consisting of diabetes (e.g. type 1 or type 2 diabetes), metabolic syndrome, liver disease, and inflammation are provided. The methods comprise administering to a subject in need of such treatment an effective amount of a compound described herein. In some embodiments, the subject is a human.

Compounds

One aspect of the current disclosure relates to compounds of Formula (I)

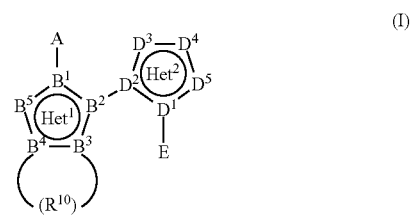

or a derivative thereof, wherein

A is an optionally substituted aryl or heteroaryl;

$B^1$, $B^2$, $B^3$, and $B^4$ are each independently C or N; and $B^5$ is $CR^1$, N, $NR^8$ or O, wherein $B^1$, $B^2$, $B^3$, $B^4$ and $B^5$ together form $Het^1$, which is an optionally substituted 5-membered heteroaryl;

$R^{10}$ is —$(CR^3)_m$—X—$(CR^5)_n$— which, together with $B^3$ and $B^4$, form an optionally substituted aryl or heteroaryl; or —$(CR^3R^4)_m$—X—$(CR^5R^6)_n$— which, together with $B^3$ and $B^4$, form an optionally substituted cycloalkyl or heterocycloalkyl;

$D^1$ and $D^2$ are each independently C or N; and $D^3$, $D^4$, and $D^5$ are each independently $CR^2$, N, $NR^8$, or O, wherein $D^1$, $D^2$, $D^3$, $D^4$, and $D^5$ together form $Het^2$, which is an optionally substituted 5-membered heteroaryl;

E is alkyl, aryl, arylalkyl, cycloalkyl, heteroalkyl, heteroaryl, or heterocycloalkyl, each of which may be optionally substituted;

each $R^1$ is independently H, alkoxy, optionally substituted $C_{1-6}$alkyl, amido, amino, cyano, halo, hydroxyl, sulfonyl, or sulfonamido;

each $R^2$ is independently H, alkoxy, optionally substituted $C_{1-6}$alkyl, amido, amino, cyano, halo, hydroxyl, sulfonyl, or sulfonamido;

each $R^3$, $R^4$, $R^5$, and $R^6$ are independently H, alkoxy, amino, an optionally substituted $C_{1-6}$alkyl, cyano, or halo;

n and m are each independently 0, 1, 2, or 3;

X is C(O), N, C(O)NR$^7$, NR$^7$, O, S, S(O), or S(O)$_2$, or absent;

$R^7$ is H, acyl, optionally substituted $C_{1-6}$alkyl, amido, carboxylate, or sulfonyl; and $R^8$ is H or optionally substituted $C_{1-6}$alkyl.

One aspect of the current disclosure relates to a compound of Formula (I) with the proviso that, when X is absent, at least one of m and n is not 0.

In some compounds of Formula (I), A is an optionally substituted phenyl or heteroaryl. In some compounds of Formula (I), A is phenyl optionally substituted with one or more substituents selected from the group consisting of alkoxy, amido, amino, an optionally substituted $C_{1-6}$alkyl, carboxylate, cyano, halo, and hydroxyl.

In some compounds of Formula (I), Het$^1$ is an imidazole or pyrazole.

In some compounds of Formula (I), the group represented by

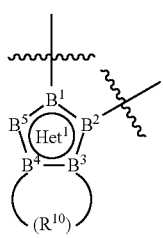

is selected from the group consisting of

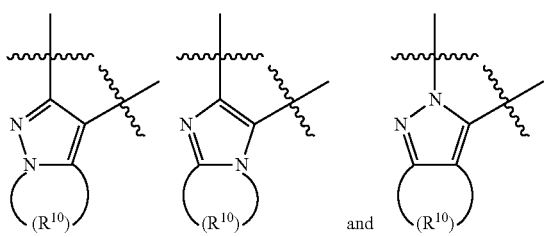

wherein $R^{10}$ is —(CR$^3$)$_m$—X—(CR$^5$)$_n$— which, together with B$^3$ and B$^4$, form an optionally substituted aryl or heteroaryl; or —(CR$^3$R$^4$)$_m$—X—(CR$^5$R$^6$)$_n$— which, together with B$^3$ and B$^4$, form an optionally substituted cycloalkyl or heterocycloalkyl;

each $R^3$, $R^4$, $R^5$, and $R^6$ are independently H, alkoxy, amino, an optionally substituted $C_{1-6}$alkyl, cyano, or halo;

n and m are each independently 0, 1, 2, or 3;

X is C(O), N, C(O)NR$^7$, NR$^7$, O, S, S(O), or S(O)$_2$, or absent; and $R^7$ is H, acyl, optionally substituted $C_{1-6}$alkyl, amido, carboxylate, or sulfonyl.

In some compounds of Formula (I), the group represented by

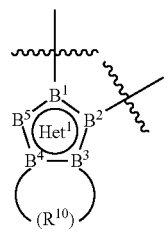

is selected from the group consisting of

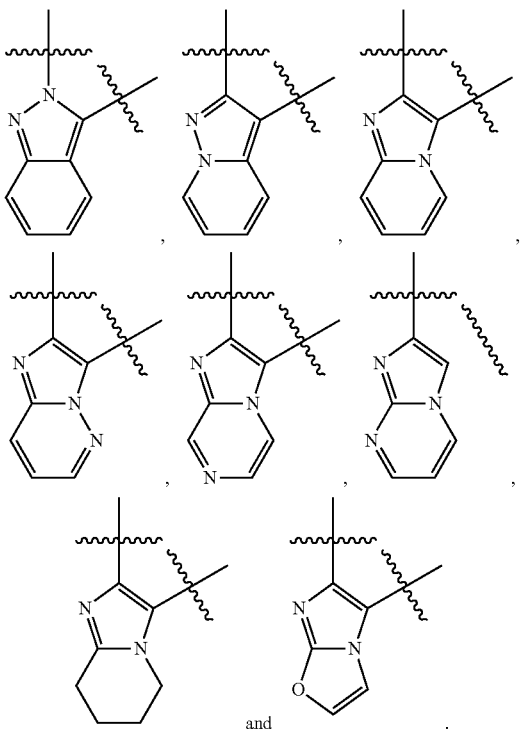

and

In some compounds of Formula (I), the group represented by

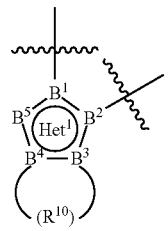

is selected from the group consisting of

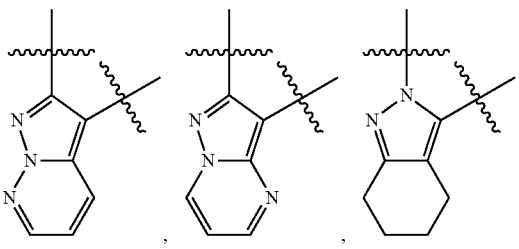

-continued

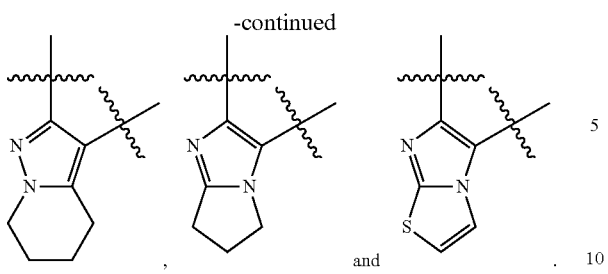

, and .

In some compounds of Formula (I), Het² is selected from the group consisting of imidazole, triazole and tetrazole.

In some compounds of Formula (I), B² and D² are both carbon.

Another aspect of the current disclosure relates to compounds of Formula (Ia)

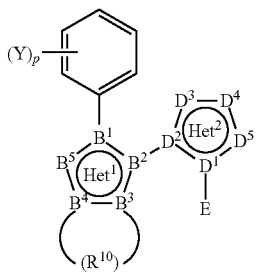

(Ia)

or a derivative thereof, wherein:
B¹, B², B³, and B⁴ are each independently C or N; and B⁵ is CR¹, N, NR⁸ or O, wherein B¹, B², B³, B⁴ and B⁵ together form Het¹, which is an optionally substituted 5-membered heteroaryl;
R¹⁰ is —(CR³)$_m$—X—(CR⁵)$_n$— which, together with B³ and B⁴, form an optionally substituted aryl or heteroaryl; or —(CR³R⁴)$_m$—X—(CR⁵R⁶)$_n$— which, together with B³ and B⁴, form an optionally substituted cycloalkyl or heterocycloalkyl;
D¹ and D² are each independently C or N; and D³, D⁴, and D⁵ are each independently CR², N, NR⁸, or O, wherein D¹, D², D³, D⁴, and D⁵ together form Het², which is an optionally substituted 5-membered heteroaryl;
E is alkyl, aryl, arylalkyl, cycloalkyl, heteroalkyl, heteroaryl, or heterocycloalkyl, each of which may be optionally substituted;
each R¹ is independently H, alkoxy, optionally substituted $C_{1-6}$alkyl, amido, amino, cyano, halo, hydroxyl, sulfonyl, or sulfonamido;
each R² is independently H, alkoxy, optionally substituted $C_{1-6}$alkyl, amido, amino, cyano, halo, hydroxyl, sulfonyl, or sulfonamido;
each R³, R⁴, R⁵, and R⁶ are independently H, alkoxy, amino, an optionally substituted $C_{1-6}$alkyl, cyano, or halo;
n and m are each independently 0, 1, 2, or 3;
p is 0, 1, 2, or 3;
X is C(O), N, C(O)NR⁷, NR⁷, O, S, S(O), or S(O)₂, or absent;
Y is an optionally substituted $C_{1-6}$alkyl, carboxylate, cyano, halo, or hydroxyl;
R⁷ is H, acyl, optionally substituted $C_{1-6}$alkyl, amido, carboxylate, or sulfonyl; and
R⁸ is H or optionally substituted $C_{1-6}$alkyl.

In some compounds of Formula (Ia), the group represented by

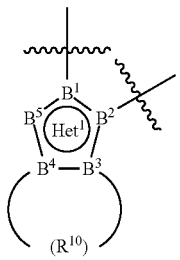

can be any of the corresponding groups of Formula (I) described above.

In some compounds of Formula (Ia), Het² is selected from the group consisting of imidazole, triazole and tetrazole.

Another aspect of the current disclosure relates to compounds of Formula (Ib)

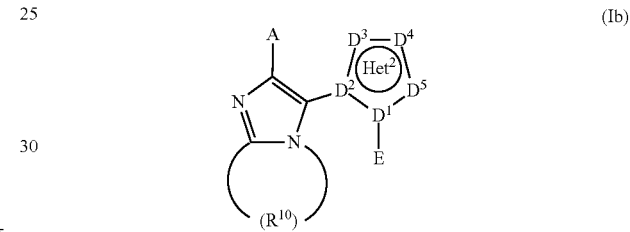

(Ib)

or a derivative thereof, wherein:
A is an optionally substituted aryl or heteroaryl;
R¹⁰ is —(CR³)$_m$—X—(CR⁵)$_n$— which, together with imidazole fused thereto, form an optionally substituted heteroaryl; or —(CR³R⁴)$_m$—X—(CR⁵R⁶)$_n$— which, together with imidazole fused thereto, form an optionally substituted heterocycloalkyl;
D¹ and D² are each independently C or N; and D³, D⁴, and D⁵ are each independently CR², N, NR⁸, or O, wherein D¹, D², D³, D⁴, and D⁵ together form Het², which is an optionally substituted 5-membered heteroaryl;
E is alkyl, aryl, arylalkyl, cycloalkyl, heteroalkyl, heteroaryl, or heterocycloalkyl, each of which may be optionally substituted;
each R² is independently H, alkoxy, optionally substituted $C_{1-6}$alkyl, amido, amino, cyano, halo, hydroxyl, sulfonyl, or sulfonamido;
each R³, R⁴, R⁵, and R⁶ are independently H, alkoxy, amino, an optionally substituted $C_{1-6}$alkyl, cyano, or halo;
n and m are each independently 0, 1, 2, or 3;
X is C(O), N, C(O)NR⁷, NR⁷, O, S, S(O), or S(O)₂, or absent;
R⁷ is H, acyl, optionally substituted $C_{1-6}$alkyl, amido, carboxylate, or sulfonyl; and
R⁸ is H or optionally substituted $C_{1-6}$alkyl.

In some compounds of Formula (Ib), Het² is selected from the group consisting of imidazole, triazole and tetrazole.

Another aspect of the current disclosure relates to compounds of Formula (Ib1)

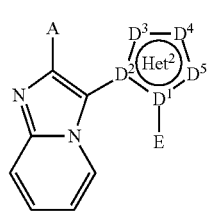

(Ib1)

or a derivative thereof, wherein:
A is an optionally substituted aryl or heteroaryl;
$D^1$ and $D^2$ are each independently C or N; and $D^3$, $D^4$, and $D^5$ are each independently $CR^2$, N, $NR^8$, or O, wherein $D^1$, $D^2$, $D^3$, $D^4$, and $D^5$ together form $Het^2$, which is an optionally substituted 5-membered heteroaryl;
E is alkyl, aryl, arylalkyl, cycloalkyl, heteroalkyl, heteroaryl, or heterocycloalkyl, each of which may be optionally substituted;
each $R^2$ is independently H, alkoxy, optionally substituted $C_{1-6}$alkyl, amido, amino, cyano, halo, hydroxyl, sulfonyl, or sulfonamido; and
$R^8$ is H or optionally substituted $C_{1-6}$alkyl.

In some compounds of Formula (Ib1), $Het^2$ is selected from the group consisting of imidazole, triazole and tetrazole.

Another aspect of the current disclosure relates to compounds of Formula (Ib2)

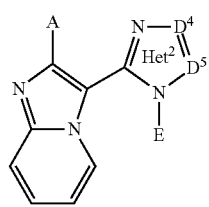

(Ib2)

or a derivative thereof, wherein:
A is an optionally substituted aryl or heteroaryl;
$D^4$ and $D^5$ are each independently $CR^2$ or N, wherein $D^4$ and $D^5$, together with the two nitrogen attached thereto form $Het^2$, which is an optionally substituted 5-membered heteroaryl;
E is alkyl, aryl, arylalkyl, cycloalkyl, heteroalkyl, heteroaryl, or heterocycloalkyl, each of which may be optionally substituted; and
each $R^2$ is independently H, alkoxy, optionally substituted $C_{1-6}$alkyl, amido, amino, cyano, halo, hydroxyl, sulfonyl, or sulfonamido.

In some compounds of Formula (Ib2), $Het^2$ is selected from the group consisting of imidazole, triazole and tetrazole.

Another aspect of the current disclosure relates to compounds of Formula (Ib3)

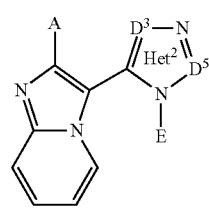

(Ib3)

or a derivative thereof, wherein:
A is an optionally substituted aryl or heteroaryl;
$D^3$ and $D^5$ are each independently $CR^2$ or N, wherein $D^3$ and $D^5$, together with the two nitrogen attached thereto form $Het^2$, which is an optionally substituted 5-membered heteroaryl;
E is alkyl, aryl, arylalkyl, cycloalkyl, heteroalkyl, heteroaryl, or heterocycloalkyl, each of which may be optionally substituted; and
each $R^2$ is independently H, alkoxy, optionally substituted $C_{1-6}$alkyl, amido, amino, cyano, halo, hydroxyl, sulfonyl, or sulfonamido.

In some compounds of Formula (Ib3), $Het^2$ is selected from the group consisting of imidazole, triazole and tetrazole.

Another aspect of the current disclosure relates to compounds of Formula (Ic)

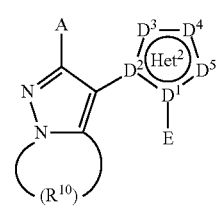

(Ic)

or a derivative thereof, wherein:
A is an optionally substituted aryl or heteroaryl;
$R^{10}$ is —$(CR^3)_m$—X—$(CR^5)_n$— which, together with pyrazole fused thereto, form an optionally substituted heteroaryl; or —$(CR^3R^4)_m$—X—$(CR^5R^6)_n$— which, together with pyrazole fused thereto, form an optionally substituted heterocycloalkyl;
$D^1$ and $D^2$ are each independently C or N; and $D^3$, $D^4$, and $D^5$ are each independently $CR^2$, N, $NR^8$, or O, wherein $D^1$, $D^2$, $D^3$, $D^4$, and $D^5$ together form $Het^2$, which is an optionally substituted 5-membered heteroaryl;
E is alkyl, aryl, arylalkyl, cycloalkyl, heteroalkyl, heteroaryl, or heterocycloalkyl, each of which may be optionally substituted;
each $R^2$ is independently H, alkoxy, optionally substituted $C_{1-6}$alkyl, amido, amino, cyano, halo, hydroxyl, sulfonyl, or sulfonamido;
each $R^3$, $R^4$, $R^5$, and $R^6$ are independently H, alkoxy, amino, an optionally substituted $C_{1-6}$alkyl, cyano, or halo;
n and m are each independently 0, 1, 2, or 3;
X is C(O), N, C(O)$NR^7$, $NR^7$, O, S, S(O), or $S(O)_2$, or absent;

R⁷ is H, acyl, optionally substituted C$_{1-6}$alkyl, amido, carboxylate, or sulfonyl; and R⁸ is H or optionally substituted C$_{1-6}$alkyl.

In some compounds of Formula (Ic), Het² is selected from the group consisting of imidazole, triazole and tetrazole.

Another aspect of the current disclosure relates to compounds of Formula (Id)

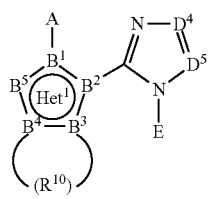

(Id)

or a derivative thereof, wherein:

A is an optionally substituted aryl or heteroaryl;

B¹, B², B³, and B⁴ are each independently C or N; and B⁵ is CR¹, N, NR⁸ or O, wherein B¹, B², B³, B⁴ and B⁵ together form Het¹, which is an optionally substituted 5-membered heteroaryl;

R¹⁰ is —(CR³)$_m$—X—(CR⁵)$_n$— which, together with B³ and B⁴, form an optionally substituted aryl or heteroaryl; or —(CR³R⁴)$_m$—X—(CR⁵R⁶)$_n$— which, together with B³ and B⁴, form an optionally substituted cycloalkyl or heterocycloalkyl;

D⁴ and D⁵ are each independently CR² or N;

E is alkyl, aryl, arylalkyl, cycloalkyl, heteroalkyl, heteroaryl, or heterocycloalkyl, each of which may be optionally substituted;

each R¹ is independently H, alkoxy, optionally substituted C$_{1-6}$alkyl, amido, amino, cyano, halo, hydroxyl, sulfonyl, or sulfonamido;

each R² is independently H, alkoxy, optionally substituted C$_{1-6}$alkyl, amido, amino, cyano, halo, hydroxyl, sulfonyl, or sulfonamido;

each R³, R⁴, R⁵, and R⁶ are independently H, alkoxy, amino, an optionally substituted C$_{1-6}$alkyl, cyano, or halo;

n and m are each independently 0, 1, 2, or 3;

X is C(O), N, C(O)NR⁷, NR⁷, O, S, S(O), or S(O)$_2$, or absent;

R⁷ is H, acyl, optionally substituted C$_{1-6}$alkyl, amido, carboxylate, or sulfonyl; and R⁸ is H or optionally substituted C$_{1-6}$alkyl.

In some compounds of Formula (Id), the group represented by

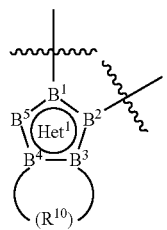

can be any of the corresponding groups of Formula (I) described above.

Other aspects of the current disclosure are described below.

Methods

As described above, compounds of Formula (I) herein modulate GPR131. In some embodiments, the compounds described herein may act as agonists or may activate GPR131. Accordingly, also provided herein are methods of treating a subject suffering from or at risk of a disease or condition for which GPR131 modulation can provide a therapeutic benefit, such methods comprising administering to the subject an effective amount of a compound described herein. In some embodiments, the disease or condition is modulated by GPR131. In some embodiments, the subject is a human.

Diseases and conditions which are modulated by GPR131 include diabetes (type 1 or type 2 diabetes), metabolic syndrome, liver disease, and inflammation. Other diseases and conditions modulated by GPR131 include autoimmune diseases such as rheumatoid arthritis and multiple sclerosis; inflammatory diseases such as allergy, osteoarthritis, chronic obstructive pulmonary disease, appendicitis, bronchial asthma, pancreatitis, allergic rash, and psoriasis; gastrointestinal disease such as inflammatory bowel disease, Crohn's disease, ulcerative colitis, short bowel syndrome (e.g. post-radiation colitis), microscopic colitis, irritable bowel syndrome and short bowel syndrome (e.g. malabsorption or to improve nutrient absorption in patients who have had intestinal segments surgically removed), and bacterial overgrowth; kidney diseases such as diabetic nephropathy, chronic renal failure, glomerular nephritis, hypertensive nephrosclerosis, chronic glomerulonephritis, chronic transplant glomerulopathy, chronic interstitial nephritis, and polysystic kidney disease; certain cancers such as colorectal cancer, liver cancer, heptacellular carcinoma, cholangio carcinoma, renal cancer, gastric cancer, pancreatic cancer, prostate cancer, and insulinoma; cardiac diseases such as congestive heart failure, myocardial infarction, atherosclerosis, angina pectoris, arteriosclerosis and cerebrovascular disease (hemorrhage, stroke, cerebrovascular infarction); and osteoporosis and other conditions characterized by low bone mass.

Still another aspect provides methods for decreasing inflammation by decreasing the pro-inflammatory activity of immune cells of the myeloid lineage in tissue in a subject, e.g. a human. The methods comprise administering an effective amount of a compound described herein to the subject. In response to administration of compound to subject, inflammatory markers and biological consequences of inflammation are reduced. In subcutaneous adipose tissue, a reduction in pro-inflammatory activity of immune cells can lead to decreased insulin resistance.

Another aspect provides for methods of treating liver disease in a subject, e.g. a human. In certain embodiments, the liver disease is nonalcoholic steatohepatitis. The methods comprise administering an effective amount of a compound described herein to the subject. In response to administration of compound to subject, inflammatory mediators, liver fats and liver fibrosis are reduced.

Other aspects of the present disclosure relate to methods of increasing insulin secretion, decreasing glucagon secretion, increasing beta cell mass, increasing insulin gene expression, inhibiting acid secretion, inhibiting, slowing or delaying gastric emptying, increasing satiety, stimulating mucosal growth, increasing intestinal nutrient absorption, inhibiting or lowering gastric acid secretion, stimulating intestinal blood flow, relaxing intestinal smooth muscle, and promoting weight loss. Such methods comprise administering to a subject an effective amount of a compound described herein.

Also provided herein are methods of improving glucose tolerance in a subject, e.g. a human. The methods comprise administering an effective amount of a compound described herein to the subject.

Another aspect provides methods of lowering blood glucose in a subject, e.g. a human. The methods comprise administering an effective amount of a compound described herein to the subject. In response to administration of a compound to the subject, blood glucose levels are lowered. The methods further comprise steps to measure blood glucose levels before and after administration of a compound described herein. Blood glucose levels are easily measured by numerous commercially available glucose monitoring devices that measure blood glucose from samples of blood or urine. Blood glucose can also be measured by commercially available glucometers that do not require blood or urine samples.

Yet another aspect of the invention provides methods for increasing energy expenditure in peripheral tissues such as adipose and skeletal muscle in a subject, e.g. a human. The methods comprise administering an effective amount of a compound described herein to the subject. In response to administration of compound to subject, net energy expenditure by the subject is elevated.

Other aspects of the current disclosure provide for methods of decreasing glucagon secretion in a subject, e.g. a human. The methods comprise administering and effect amount of a compound described herein to the subject. For example, in certain methods, after administration to the subject, glucagon secretion from the pancreatic alpha cell is reduced.

Other aspects of the present disclosure provide for methods of stimulating incretin production in a subject, e.g. a human. The methods comprise administering an effective amount of a compound described herein to the subject.

Methods of raising intracellular levels of cAMP in a cell expressing GPR131 are also provided. The methods comprise exposing a cell that expresses GPR131 to a compound described herein. In certain embodiments, the cell that expresses GPR131 is a gastro-intestinal endocrine cell (e.g. a GLP-1 secreting L-cell), a gastro-intestinal chemosensory cell, an adipose tissue cell, a skeletal muscle cell, or an immune system cell of the myeloid lineage including a circulating CD14+ monocyte, macrophage and Kupffer cell.

Other aspects of the present disclosure provide for methods of stimulating or increasing glucagon-like peptide-1 secretion from cells, e.g. human cells, or in a subject, e.g. a human. The methods comprise exposing an effective amount of a compound described herein to the cell or subject.

Other aspects of the present disclosure provide for methods of stimulating or increasing glucagon-like peptide-2 secretion from cells, e.g. human cells, or in a subject, e.g. a human. The methods comprise exposing an effective amount of a compound described herein to the cell or subject.

Other aspects of the present disclosure provide for methods of stimulating or increasing protein YY secretion from cells, e.g. human cells, or in a subject, e.g. a human. The methods comprise exposing an effective amount of a compound described herein to the cell or subject.

The present disclosure further contemplates combination therapy and methods of concomitant administration of a first agent and a second agent wherein the first agent is a compound of Formula (I) and the second agent is selected from the group consisting of biguanides (such as metformin); thiazolidinediones (such as ciglitazone, pioglitazone, troglitazone, and rosiglitazone); dipeptidyl-peptidase-4 ("DPP IV") inhibitors (such as vildagliptin and sitagliptin); glucagon-like peptide-1 ("GLP-1") receptor agonists (such as exanatide and liraglutide) (or GLP-1 mimetics); PPAR gamma agonists or partial agonists; dual PPAR alpha, PPAR gamma agonists or partial agonists; dual PPAR delta, PPAR gamma agonists or partial agonists; pan PPAR agonists or partial agonists; dehydroepiandrosterone (also referred to as DHEA or its conjugated sulphate ester, DHEA-SO$_4$); antiglucocorticoids; TNFα inhibitors; α-glucosidase inhibitors (such as acarbose, miglitol, and voglibose); sulfonylureas (such as chlorpropamide, tolbutamide, acetohexamide, tolazamide, glyburide, gliclazide, glynase, glimepiride, and glipizide); pramlintide (a synthetic analog of the human hormone amylin); other insulin secretagogues (such as repaglinide, gliquidone, and nateglinide); insulin; insulin mimetics; insulin sensitizers; glucagon receptor antagonists; gastric inhibitory peptide ("GIP"); and GIP mimetics.

Combination therapy and concomitant administration refer to the administration of the two agents (i.e., a first agent and a second agent, as described above) in any manner in which the pharmacological effects of both are manifested in the patient at the same time. Thus, such administration does not require that a single pharmaceutical composition, the same type of formulation, the same dosage form, or even the same route of administration be used for administration of both the first and second agents, or that the two agents be administered at the same time. However, such administration will be accomplished most conveniently by the same dosage form and the same route of administration, at substantially the same time. Such administration most advantageously proceeds by delivering both active ingredients simultaneously in a novel pharmaceutical composition in accordance with the present disclosure.

In certain embodiments, the second agent is a DPP IV inhibitor listed as one of compound A-E as follows: A: Sitagliptin; B: Vildagliptin; C: Saxagliptin; D: Denagliptin; E: Alogliptin; F: Linagliptin.

In further embodiments, it is contemplated that one or more compounds of Formula (I) when administered with one or more DPP IV inhibitors identified above as A-F, act synergistically in treating diabetes. Compounds of Formula (I) include compounds identified as compounds 500-594 in Examples 1-95. Specific combinations include a synergistically effective amount of each compound in the following combinations: 500A, 500B, 500C, 500D, 500E, 500F, 501A, 501B, 501C, 501D, 501E, 501F, 502A, 502B, 502C, 502D, 502E, 502F, 503A, 503B, 503C, 503D, 503E, 503F, 504A, 504B, 504C, 504D, 504E, 504F, 505A, 505B, 505C, 505D, 505E, 505F, 506A, 506B, 506C, 506D, 506E, 506F, 507A, 507B, 507C, 507D, 507E, 507F, 508A, 508B, 508C, 508D, 508E, 508F, 509A, 509B, 509C, 509D, 509E, 509F, 510A, 510B, 510C, 510D, 510E, 510F, 511A, 511B, 511C, 511D, 511E, 511F, 512A, 512B, 512C, 512D, 512E, 512F, 513A, 513B, 513C, 513D, 513E, 513F, 514A, 514B, 514C, 514D, 514E, 514F, 515A, 515B, 515C, 515D, 515E, 515F, 516A, 516B, 516C, 516D, 516E, 516F, 517A, 517B, 517C, 517D, 517E, 517F, 518A, 518B, 518C, 518D, 518E, 518F, 519A, 519B, 519C, 519D, 519E, 519F, 520A, 520B, 520C, 520D, 520E, 520F, 521A, 521B, 521C, 521D, 521E, 521F, 522A, 522B, 522C, 522D, 522E, 522F, 523A, 523B, 523C, 523D, 523E, 523F, 524A, 524B, 524C, 524D, 524E, 524F, 525A, 525B, 525C, 525D, 525E, 525F, 526A, 526B, 526C, 526D, 526E, 526F, 527A, 527B, 527C, 527D, 527E, 527F, 528A, 528B, 528C, 528D, 528E, 528F, 529A, 529B, 529C, 529D, 529E, 529F, 530A, 530B, 530C, 530D, 530E, 530F, 531A, 531B, 531C, 531D, 531E, 531F, 532A, 532B, 532C, 532D, 532E, 532F, 533A, 533B, 533C, 533D, 533E, 533F, 534A, 534B, 534C, 534D, 534E, 534F, 535A, 535B, 535C, 535D, 535E, 535F, 536A, 536B, 536C, 536D, 536E, 536F, 537A, 537B, 537C, 537D, 537E, 537F, 538A, 538B, 538C, 538D, 538E, 538F, 539A, 539B, 539C, 539D, 539E, 539F, 540A, 540B, 540C, 540D, 540E, 540F, 541A, 541B, 541C, 541D, 541E, 541F, 542A, 542B, 542C, 542D, 542E, 542F, 543A, 543B, 543C, 543D, 543E, 543F, 544A, 544B, 544C, 544D, 544E, 544F, 545A, 545B, 545C, 545D, 545E, 545F, 546A, 546B, 546C, 546D, 546E, 546F, 547A, 547B, 547C, 547D, 547E, 547F, 548A, 548B, 548C, 548D, 548E, 548F, 549A, 549B, 549C, 549D, 549E, 549F, 550A, 550B, 550C, 550D, 550E, 550F, 551A, 551B, 551C, 551D, 551E, 551F, 552A, 552B, 552C, 552D, 552E, 552F, 553A, 553B, 553C, 553D, 553E, 553F, 554A, 554B, 554C, 554D, 554E, 554F, 555A, 555B, 555C, 555D, 555E, 555F, 556A, 556B, 556C, 556D, 556E, 556F, 557A, 557B, 557C, 557D, 557E, 557F, 558A, 558B, 558C, 558D, 558E, 558F, 559A, 559B, 559C, 559D, 559E, 559F, 560A, 560B, 560C, 560D, 560E, 560F, 561A, 561B, 561C, 561D, 561E, 561F, 562A, 562B, 562C, 562D, 562E, 562F, 563A, 563B, 563C, 563D, 563E, 563F, 564A, 564B, 564C, 564D, 564E, 574F, 565A, 565B, 565C, 565D, 565E, 565F, 566A, 566B, 566C, 566D, 566E, 566F, 567A, 567B, 567C, 567D, 567E, 567F, 568A, 568B, 568C, 568D, 568E, 568F, 569A, 569B, 569C, 569D, 569E, 569F, 570A, 570B, 570C, 570D, 570E, 570F, 571A, 571B, 571C, 571D, 571E, 571F, 572A, 572B, 572C, 572D, 572E, 572F, 573A, 573B, 573C, 573D, 573E, 573F, 574A, 574B, 574C, 574D, 574E, 574F, 575A, 575B, 575C, 575D, 575E, 575F, 576A, 576B, 576C, 576D, 576E, 576F, 577A, 577B, 577C, 577D, 577E, 577F, 578A, 578B, 578C, 578D, 578E, 578F, 579A, 579B, 579C, 579D, 579E, 579F, 580A, 580B, 580C, 580D, 580E, 580F, 581A, 581B, 581C, 581D, 581E, 581F, 582A, 582B, 582C, 582D, 582E, 582F, 583A, 583B, 583C, 583D, 583E, 583F, 584A, 584B, 584C, 584D, 584E, 584F, 585A, 585B, 585C, 585D, 585E, 585F, 586A, 586B, 586C, 586D, 586E, 586F, 587A, 587B, 587C, 587D, 587E, 587F, 588A, 588B, 588C, 588D, 588E, 588F, 589A, 589B, 589C, 589D, 589E, 589F, 590A, 590B, 590C, 590D, 590E, 590F, 591A, 591B, 591C, 591D, 591E, 591F, 592A, 592B, 592C, 592D, 592E, 592F, 593A, 593B, 593C, 593D, 593E, 593F, 594A, 594B, 594C, 594D, 594E, and 594F.

In accordance with the description above, other diseases, conditions and disorders described herein (including but not limited to metabolic syndrome, liver disease, and inflammation) may also be treated with a first agent comprising a compound of Formula (I) and a second agent described above.

Compounds of Formula (I) can be incorporated into a variety of formulations and medicaments for therapeutic administration. More particularly, compounds of Formula (I) can be formulated into pharmaceutical compositions by combination with appropriate, pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, and/or intratracheal administration. Moreover, the compound can be administered in a local rather than systemic manner, in a depot or sustained release formulation. In addition, the compounds can be administered in a liposome.

Compounds of Formula (I) can also be formulated with common excipients, diluents or carriers and compressed into tablets, or formulated as elixirs or solutions for convenient oral administration, or administered by the intramuscular or intravenous routes. The compounds can be administered transdermally, and can be formulated as sustained release dosage forms and the like.

EXAMPLES

General Synthetic Methods.

All operations of chemical synthesis involving moisture and/or oxygen sensitive materials were conducted under an atmosphere of dry nitrogen in pre-dried glassware. Unless noted otherwise, materials were obtained from commercially available sources and used without further purification.

Flash chromatography was performed on an Isco Combiflash Companion using RediSep Rf silica gel cartridges by Teledyne Isco. Thin layer chromatography was performed using precoated plates purchased from E. Merck (silica gel 60 $PF_{254}$, 0.25 mm) and spots were visualized with long-wave ultraviolet light followed by an appropriate staining reagent.

Nuclear magnetic resonance ("NMR") spectra were recorded on a Varian Inova-400 resonance spectrometer. $^1$H NMR chemical shifts are given in parts per million ($\delta$) downfield from tetramethylsilane ("TMS") using TMS or the residual solvent signal ($CHCl_3=\delta$ 7.24, DMSO=$\delta$ 2.50) as internal standard. $^1$H NMR information is tabulated in the following format: multiplicity (s, singlet; d, doublet; t, triplet; q, quartet; m, multiplet), coupling constant(s) (J) in Hertz, number of protons. The prefix app is occasionally applied in cases where the true signal multiplicity was unresolved and br indicates the signal in question was broadened.

The compounds were named using ChemBioDraw Ultra Version 12.0.

LCMS analyses were performed using a PE SCIEX API 2000 spectrometer with a Phenomenex Luna 5 micron $C_{18}$ column or an Agilent 1260 Infinity spectrometer with an Agilent Kinetex Column 2.6 micron $C_{18}$ column.

Preparatory HPLC was performed on a Gilson HPLC 215 liquid handler with a Phenomenex column (Gemini 10μ, $C_{18}$, 110A) and a UV/VIS 156 detector.

Compounds of Formula (I) and derivatives thereof can be synthesized via a variety of different synthetic routes using commercially available starting materials and/or starting materials prepared by conventional synthetic methods. When production of starting materials is not particularly described, the compounds are known or may be prepared analogously to methods known in the art or as disclosed in the examples. One of skill in the art will appreciate that synthetic methodologies described herein are only representative of methods for preparation of the compounds described herein, and that other well known methods may be used.

Although many of the synthetic schemes discussed herein do not illustrate the use of protecting groups, skilled artisans will recognize that in some instances certain substituents may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups, their attachment and removal suitable for a particular application can be found, for example, in *Protective Groups in Organic Synthesis*, Greene & Wuts, 2nd Ed., John Wiley & Sons, New York, 1991.

Prodrugs as described herein may be prepared by routine modification of the synthetic methods described herein. Conditions for carrying out such reactions and for deprotecting the product to yield a prodrug as described herein are well-known.

Synthesis of certain compounds, and intermediates used to prepare such compounds, is detailed in the following sections. Compound numbers are listed for convenience.

Preparation of Intermediates

Intermediate 1

2-(2-Chlorophenyl)imidazo[1,2-c]pyridine-3-carboxylic acid (2)

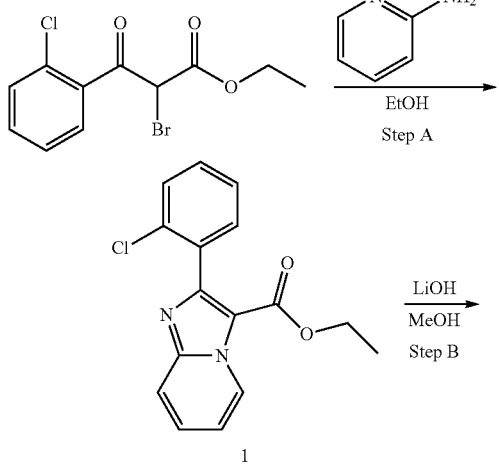

Step A: A solution of ethyl 2-bromo-3-(2-chlorophenyl)-3-oxopropanoate (3.05 g, 10 mmol) and 2-iminopyridine (1.89 g, 20 mmol) in ethanol (20 mL) was heated at 80° C. for 18 hours. The solvent was removed in vacuo and the residue was purified by flash column chromatography on silica gel (30% EtOAc in hexanes) to give ethyl 2-(2-chlorophenyl)imidazo[1,2-c]pyridine-3-carboxylate (1).

Step B: A mixture of ethyl 2-(2-chlorophenyl)imidazo[1,2-c]pyridine-3-carboxylate (1) (600 mg, 2.0 mmol), 10% aq. LiOH (1 mL) and methanol (10 mL) were heated at 70° C. for 2 hours. The volatiles were removed in vacuo, acidified to pH 4 with 1N HCl, and the mixture was extracted with ethyl acetate. The combined organic layers were washed with brine, dried over sodium sulfate, filtered and concentrated in vacuo to provide 2-(2-chlorophenyl)imidazo[1,2-c]pyridine-3-carboxylic acid (2).

Intermediate 2

2-(2,5-Dichlorophenyl)imidazo[1,2-c]pyridine-3-carboxylic acid (4)

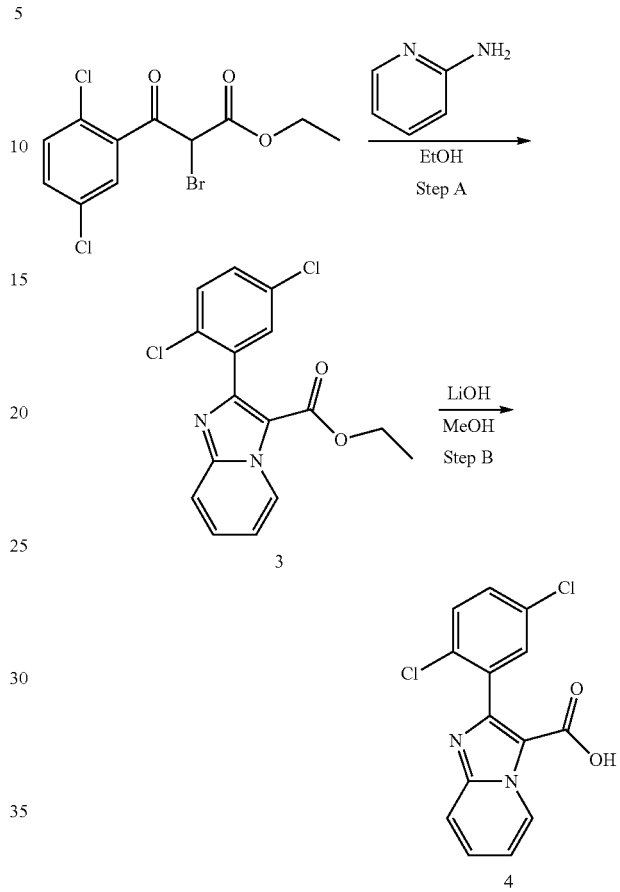

Step A: Ethyl 2-(2,5-dichlorophenyl)imidazo[1,2-c]pyridine-3-carboxylate (3) was prepared in a similar manner as that described for the synthesis of compound 1 using ethyl 2-bromo-3-(2-chlorophenyl)-3-oxopropanoate (6.8 g, 20 mmol) and pyridin-2-amine (7.53 g, 80 mmol) in ethanol (40 mL).

Step B: 2-(2,5-Dichlorophenyl)imidazo[1,2-c]pyridine-3-carboxylic acid (4) was prepared in a similar manner as that described for the synthesis of compound 2 using 2-(2,5-dichlorophenyl)imidazo[1,2-c]pyridine-3-carboxylate (3) (4.53 g, 13.5 mmol), 10% LiOH (6.5 mL), and methanol (68 mL).

Intermediate 3

2-(2,5-Dichlorophenyl)imidazo[1,2-b]pyridazine-3-carboxylic acid (6)

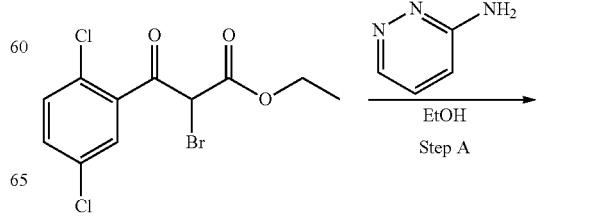

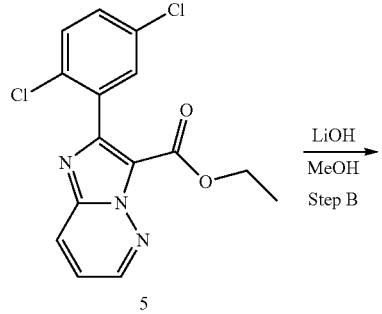

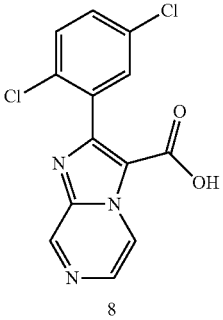

Step A: Ethyl 2-(2,5-dichlorophenyl)imidazo[1,2-a]pyrazine-3-carboxylate (7) was prepared in a similar manner as that described for the synthesis of compound 1 using ethyl 2-bromo-3-(2-chlorophenyl)-3-oxopropanoate (3.06 g, 9.0 mmol) and pyrazin-2-amine (3.42 g, 36.0 mmol) in ethanol (18 mL).

Step B: 2-(2,5-Dichlorophenyl)imidazo[1,2-a]pyrazine-3-carboxylic acid (8) was prepared in a similar manner as that described for the synthesis of compound 2 using ethyl 2-(2,5-dichlorophenyl)imidazo[1,2-a]pyrazine-3-carboxylate (7) (485 mg, 1.44 mmol), 10% LiOH (0.69 mL), and methanol (7 mL).

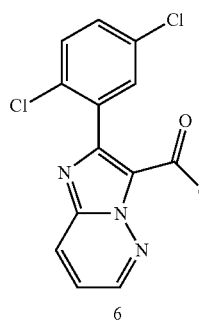

Step A: Ethyl 2-(2,5-dichlorophenyl)imidazo[1,2-b]pyridazine-3-carboxylate (5) was prepared in a similar manner as that described for the synthesis of compound 1 using ethyl 2-bromo-3-(2-chlorophenyl)-3-oxopropanoate (3.40 g, 10 mmol) and pyridazin-3-amine (3.80 g, 40 mmol) in ethanol (20 mL).

Step B: 2-(2,5-Dichlorophenyl)imidazo[1,2-b]pyridazine-3-carboxylic acid (6) was prepared in a similar manner as that described for the synthesis of compound 2 using ethyl 2-(2,5-dichlorophenyl)imidazo[1,2-b]pyridazine-3-carboxylate (5) (806 mg, 2.4 mmol), 10% LiOH (3 mL), and methanol (12 mL).

Intermediate 5

2-(2,5-Dichlorophenyl)imidazo[1,2-a]pyrimidine-3-carboxylic acid (10)

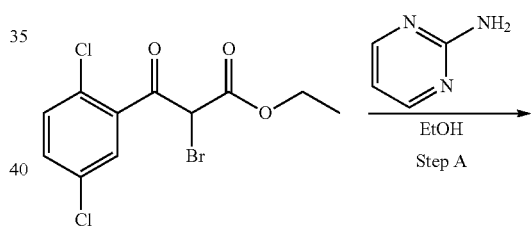

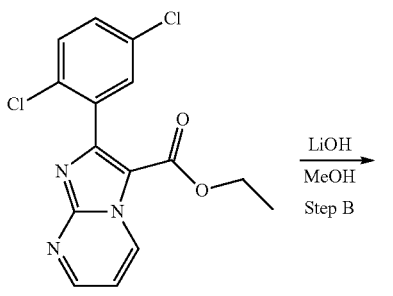

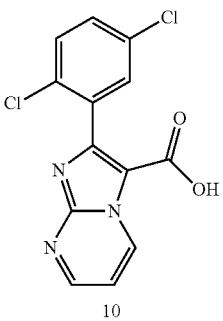

Intermediate 4

2-(2,5-Dichlorophenyl)imidazo[1,2-c]pyrazine-3-carboxylic acid (8)

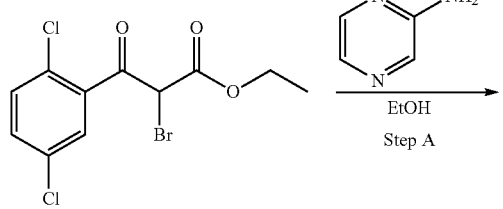

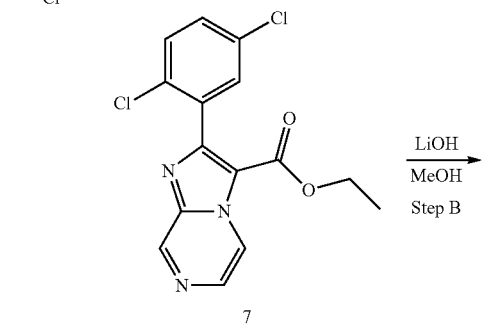

Step A: Ethyl 2-(2,5-dichlorophenyl)imidazo[1,2-a]pyrimidine-3-carboxylate (9) was prepared in a similar manner as that described for the synthesis of compound 1 using ethyl 2-bromo-3-(2-chlorophenyl)-3-oxopropanoate (2.04 g, 6.0 mmol) and pyrimidin-2-amine (2.28 g, 24 mmol) in ethanol (12 mL).

Step B: 2-(2,5-Dichlorophenyl)imidazo[1,2-a]pyrimidine-3-carboxylic acid (10) was prepared in a similar manner as that described for the synthesis of compound 2 using ethyl 2-(2,5-dichlorophenyl)imidazo[1,2-a]pyrimidine-3-carboxylate (9) (800 mg, 2.38 mmol), 10% LiOH (2.9 mL), and methanol (12 mL).

Intermediate 6

2-(2-Chloro-5-fluorophenyl)imidazo[1,2-c]pyrimidine-3-carboxylic acid (12)

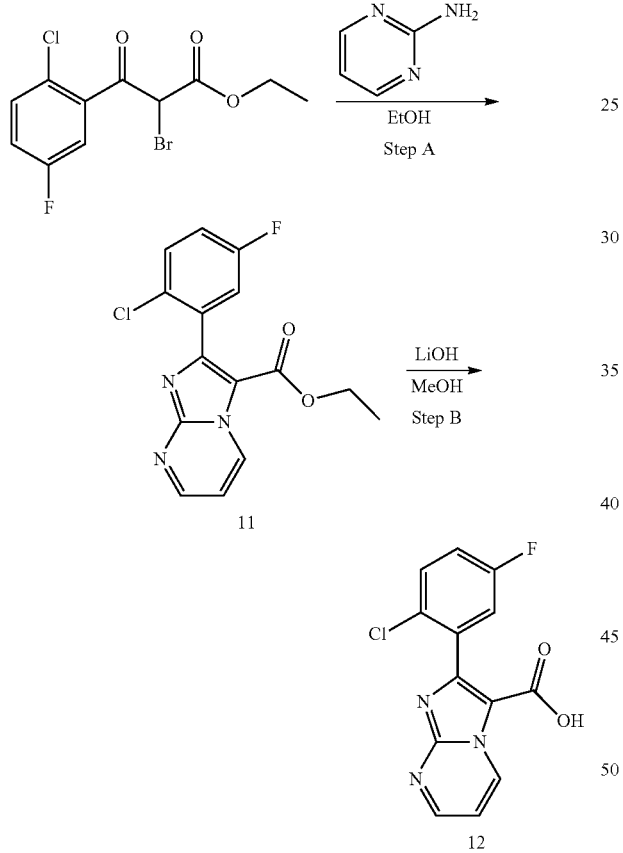

Step A: Ethyl 2-(2-chloro-5-fluorophenyl)imidazo[1,2-c]pyrimidine-3-carboxylate (11) was prepared in a similar manner as that described for the synthesis of compound 1 using ethyl 2-bromo-3-(2-chloro-5-fluorophenyl)-3-oxopropanoate (3.24 g, 10 mmol) and pyrimidin-2-amine (3.80 g, 40 mmol) in ethanol (20 mL).

Step B: 2-(2-Chloro-5-fluorophenyl)imidazo[1,2-c]pyrimidine-3-carboxylic acid (12) was prepared in a similar manner as that described for the synthesis of compound 2 using ethyl 2-(2-chloro-5-fluorophenyl)imidazo[1,2-c]pyrimidine-3-carboxylate (11) (810 mg, 2.53 mmol), 10% LiOH (3 mL), and methanol (13 mL).

Intermediate 7

2-(2,5-Dichlorophenyl)imidazo[1,2-c]pyridine-3-carbohydrazide (16)

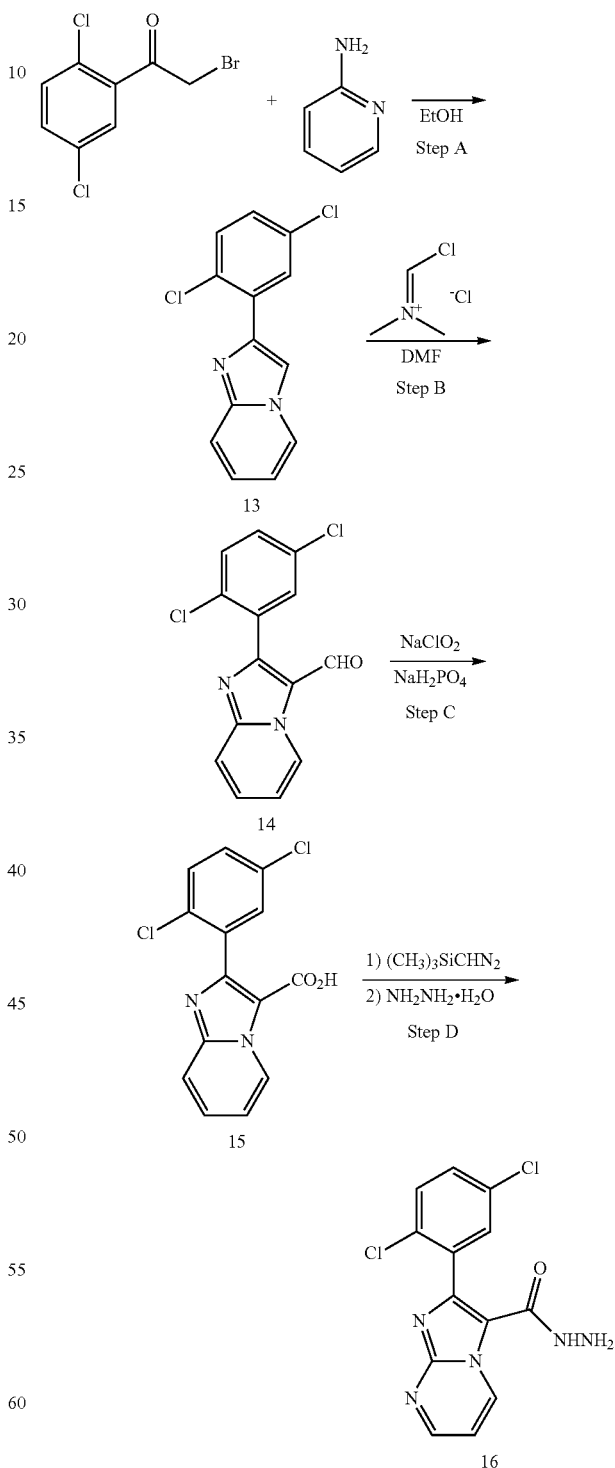

Step A: A solution of 2-bromo-1-(2,5-dichlorophenyl)ethanone (10 g, 37.3 mmol), and 2-aminopyrdine (3.51 g, 37.3 mmol) in ethanol (150 mL) was refluxed overnight. The reaction was concentrated in vacuo and dichloromethane was added. The organic layer was washed with 1N NaOH, dried over sodium sulfate, filtered and concentrated in vacuo. The residue was purified by flash column chromatography on silica gel (0-25% EtOAc in hexanes) to afford 2-(2,5-dichlorophenyl)imidazo[1,2-c]pyridine (13).

Step B: A solution of 2-(2,5-dichlorophenyl)imidazo[1,2-c]pyridine (13) (3.26 g, 12.39 mmol) and (chloromethylene)dimethylammonium chloride (4.76 g, 37.17 mmol) in DMF (46 mL) was heated at 70° C. for 2 hours. The reaction was cooled to room temperature, added to ice and stirred until all ice was melted. The white solid was filtered washing with water and hexane to yield 2-(2,5-dichlorophenyl)imidazo[1,2-c]pyridine-3-carbaldehyde (14).

Step C: To a solution of 2-(2,5-dichlorophenyl)imidazo[1,2-c]pyridine-3-carbaldehyde (14) (1.0 g, 3.43 mmol) in t-butanol (34 mL) and water (17 mL) was added 2-methyl-2-butene (2 M in THF, 11 mL, 23.01 mmol), sodium phosphate monobasic (0.32 g, 2.67 mmol), and sodium chlorite (80%, 3.9 g, 34.3 mmol). The mixture was stirred until it became homogenous at which point the reaction was deemed complete by HPLC. Ethyl acetate (150 mL) and water (100 mL) was added and the solution was stirred vigorously for two hours. The layers were separated and the organic layer was dried over sodium sulfate, filtered and concentrated in vacuo to give 2-(2,5-dichlorophenyl)imidazo[1,2-c]pyridine-3-carboxylic acid (15) as a white solid.

Step D: To a solution of 2-(2,5-dichlorophenyl)imidazo[1,2-c]pyridine-3-carboxylic acid (15) (1.0 g, 3.26 mmol) in methanol (60 mL) and toluene (40 mL) was added trimethylsilyldiazomethane (3 mL) until the yellow color persisted. The reaction was concentrated in vacuo to yield the intermediate methyl ester as a yellow solid. To the solid was added ethanol (30 mL) and hydrazine hydrate (5 mL) and the solution was refluxed overnight. The mixture was cooled to room temperature and the white precipitate was filtered to afford 2-(2,5-dichlorophenyl)imidazo[1,2-c]pyridine-3-carbohydrazide (16).

Intermediate 8

3-(4-(4-Chlorophenyl)-4H-1,2,4-triazol-3-yl)-2-(4-fluorophenyl)pyrazolo[1,5-c]pyridine (19)

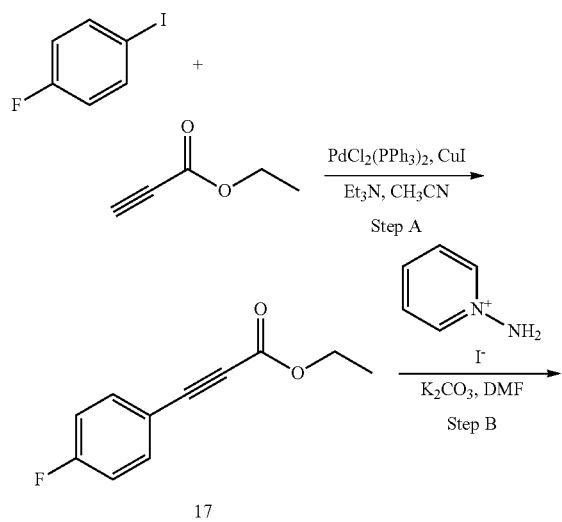

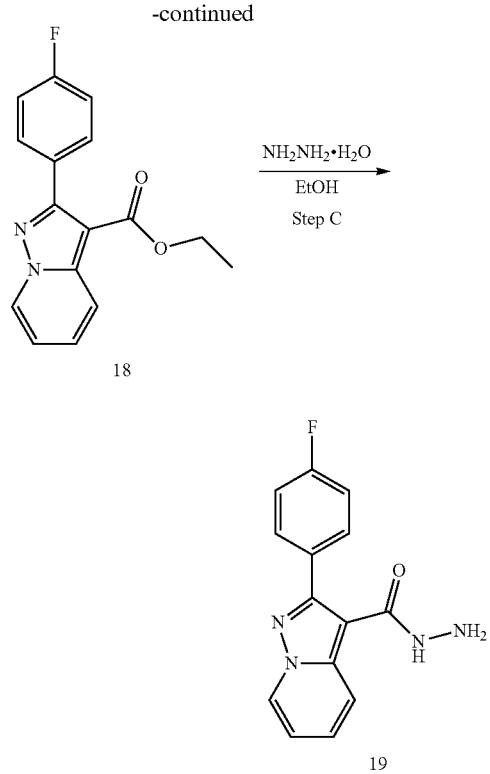

Step A: A mixture of 1-fluoro-4-iodobenzene (0.800 mL, 7.89 mmol), ethyl propiolate (1.00 mL, 8.67 mmol), bis(triphenylphosphine) palladium (II) chloride (0.539 g, 0.767 mmol), copper (I) iodide (0.329 g, 0.173 mmol), and triethylamine (3.30 mL, 23.7 mmol) in 6.0 mL of acetonitrile was purged with $N_2$ and stirred at room temperature for 40 min and then heated at 55° C. for 2 hours. The crude material was evaporated in vacuo and the residue was purified by flash column chromatography on silica gel (0%-30% EtOAc in hexanes) to afford ethyl 3-(4-fluorophenyl)propiolate (17) as a yellow solid (70.8 mg).

Step B: A mixture of ethyl 3-(4-fluorophenyl)propiolate (17) (0.076 g, 0.34 mmol), 1-aminopyridinium iodide (0.089 g, 0.399 mmol), and crushed potassium carbonate (0.120 g, 0.870 mmol) in 2.0 mL of DMF was stirred at room temperature for 18 hours. The crude material was evaporated in vacuo and the residue was purified by flash column chromatography on silica gel (5%-30% EtOAc in hexanes) to yield ethyl 2-(4-fluorophenyl)pyrazolo[1,5-c]pyridine-3-carboxylate (18) as a beige solid (99.1 mg).

Step C: A solution of ethyl 2-(4-fluorophenyl)pyrazolo[1,5-c]pyridine-3-carboxylate (18) (0.099 g, 0.348 mmol) in 2.0 mL of hydrazine hydrate and 2.0 mL of EtOH was heated in a sealed vessel at 80° C. for 20 hrs. The crude material was evaporated in vacuo and the residue was purified by flash column chromatography on silica gel (70%-100% EtOAc in hexanes) to produce 2-(4-fluorophenyl)pyrazolo[1,5-c]pyridine-3-carbohydrazide (19) as an off-white solid (58.0 mg).

Intermediate 9

2-(2-Chlorophenyl)-N-(4-chlorophenyl)imidazo[1,2-c]pyridine-3-carbohydrazonamide (22)

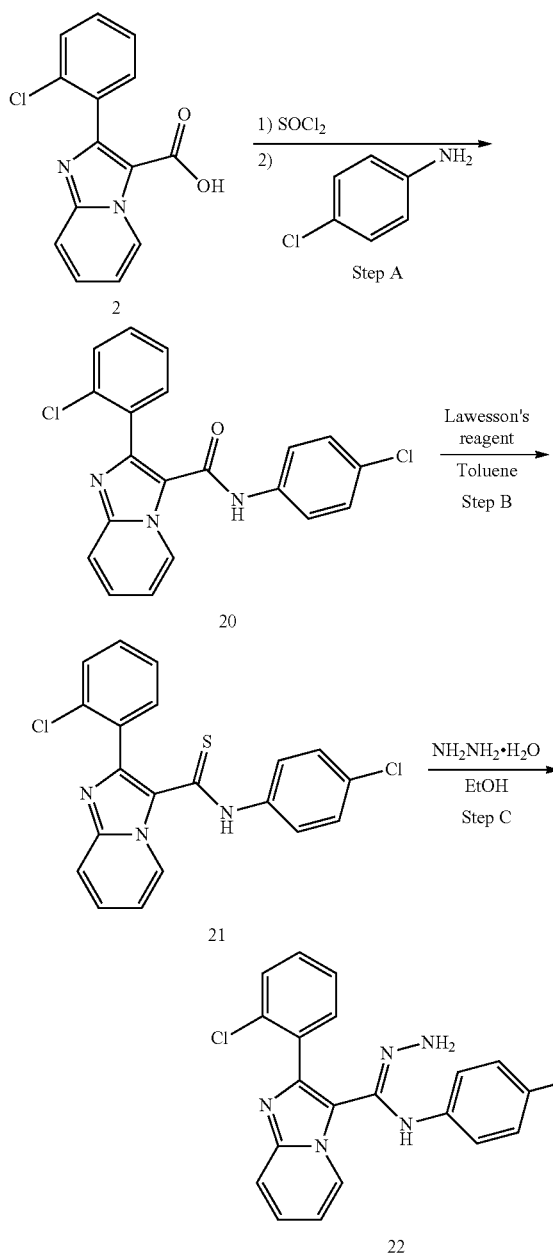

Step A: A solution of 2-(2-chlorophenyl)imidazo[1,2-c]pyridine-3-carboxylic acid (2) (409.0 mg, 1.50 mmol) in thionyl chloride (5.5 mL) was heated at 100° C. for 2 hours. The reaction was concentrated in vacuo and to the residue was added triethyl amine (230 μL, 1.65 mmol), 4-chloroaniline (191.3 mg, 1.50 mmol), and dichloromethane (7.5 mL). After the reaction was stirred at room temperature for 3 hours, the solvent was removed in vacuo and the residue was purified on the reverse phase HPLC to yield 2-(2-chlorophenyl)-N-(4-chlorophenyl)imidazo[1,2-c]pyridine-3-carboxamide (20).

Step B: A mixture of 2-(2-chlorophenyl)-N-(4-chlorophenyl)imidazo[1,2-c]pyridine-3-carboxamide (20) (496.9 mg, 1.30 mmol), Lawesson's Reagent (525.8 mg, 1.30 mmol), and toluene (6.5 mL) was heated in the microwave synthesizer at 150° C. for 4 hours. The reaction was concentrated in vacuo and the crude material was purified by flash column chromatography on silica gel (50%-100% EtOAc in hexanes) to provide 2-(2-chlorophenyl)-N-(4-chlorophenyl)imidazo[1,2-c]pyridine-3-carbothioamide (21).

Step C: To a mixture of 2-(2-chlorophenyl)-N-(4-chlorophenyl)imidazo[1,2-c]pyridine-3-carbothioamide (21) (318.7 mg, 0.80 mmol) in ethanol (4 mL) was added hydrazine hydrate (0.25 mL, 8.0 mmol). The reaction was stirred at 70° C. for one hour after which the solvent was removed. To the residue ethyl acetate and water were added and the layers were separated. The organic layers were washed with brine, dried over sodium sulfate, filtered and concentrated in vacuo to give 2-(2-chlorophenyl)-N-(4-chlorophenyl)imidazo[1,2-a]pyridine-3-carbohydrazonamide (22).

Intermediate 10

2-(2-Chlorophenyl)imidazo[1,2-a]pyridine-3-carboxamide (23)

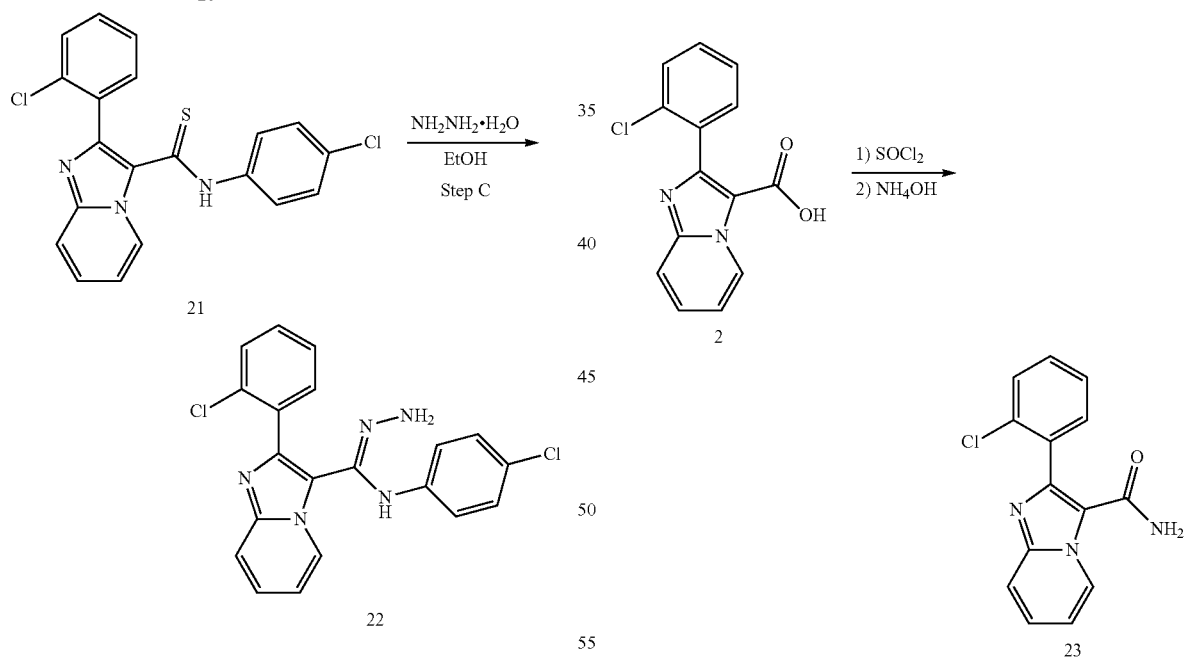

A solution of 2-(2-chlorophenyl)imidazo[1,2-a]pyridine-3-carboxylic acid (2) (136.4 mg, 0.50 mmol) in thionyl chloride (5.5 mL) was heated at 100° C. for 2 hours. The reaction was concentrated in vacuo and to the residue was added THF (5 mL) and ammonium hydroxide (0.33 mL, 5.0 mmol). After the reaction was stirred at room temperature for 30 minutes, the solvent was removed in vacuo to yield 2-(2-chlorophenyl)imidazo[1,2-a]pyridine-3-carboxamide (23).

Intermediate 11

N-(4-Chlorophenyl)-2-(2,5-dichlorophenyl)-N'-(2,2-dimethoxyethyl)imidazo[1,2-a]pyridine-3-carboximidamide (25)

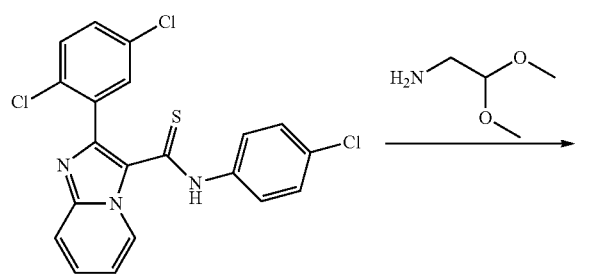

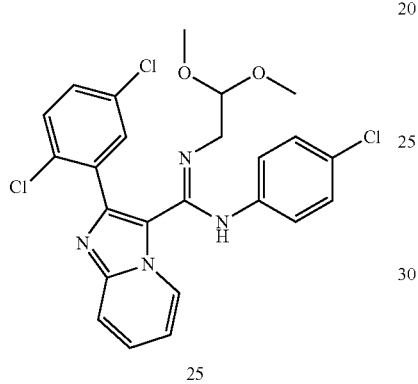

A solution of N-(4-chlorophenyl)-2-(2,5-dichlorophenyl)imidazo[1,2-a]pyridine-3-carbothioamide (24) (108.19 mg, 0.25 mmol) and 2-aminoacetaldehyde dimethyl acetal (2.7 mL) was stirred at 120° C. for 5 hours. The reaction was diluted with ethyl acetate and washed with brine. The organic layer was dried over sodium sulfate, filtered and concentrated in vacuo to provide N-(4-chlorophenyl)-2-(2,5-dichlorophenyl)-N-(2,2-dimethoxyethyl)imidazo[1,2-a]pyridine-3-carboximidamide (25).

Intermediate 12

2-(2,5-Dichlorophenyl)-5,6,7,8-tetrahydroimidazo[1,2-a]pyridine-3-carboxylic acid (27)

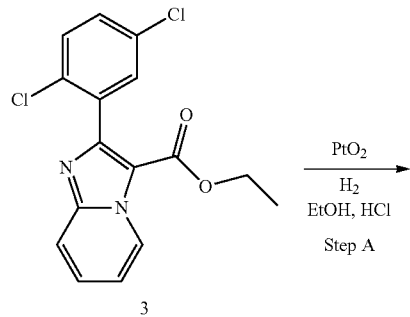

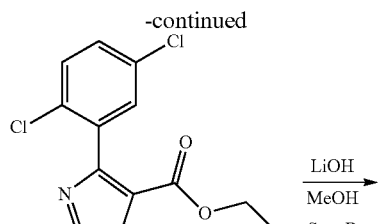

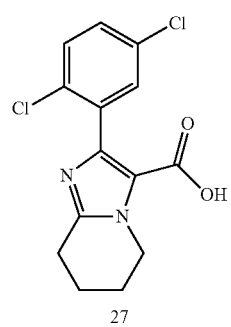

Step A: A pressure vessel was charged with ethyl 2-(2,5-dichlorophenyl)imidazo[1,2-a]pyridine-3-carboxylate (3) (5.03 g, 15 mmol), platinum (IV) oxide (22.8 mg, 0.10 mmol), 2 drops of concentrated HCl, in ethanol (100 mL) and pressurized with hydrogen gas to 4 psi and shaken overnight. The reaction was filtered through celite and concentrated in vacuo to provide ethyl 2-(2,5-dichlorophenyl)-5,6,7,8-tetrahydroimidazo[1,2-a]pyridine-3-carboxylate (26).

Step B: 2-(2,5-dichlorophenyl)-5,6,7,8-tetrahydroimidazo[1,2-a]pyridine-3-carboxylic acid (27) was prepared in a similar manner as that described for the synthesis of compound 2 using ethyl 2-(2,5-dichlorophenyl)-5,6,7,8-tetrahydroimidazo[1,2-a]pyridine-3-carboxylate (26) (4.07 g, 12 mmol), 10% LiOH (10 mL), and methanol (30 mL).

Intermediate 13

6-(2,5-Dichlorophenyl)imidazo[2,1-b]oxazole-5-carboxylic acid (30)

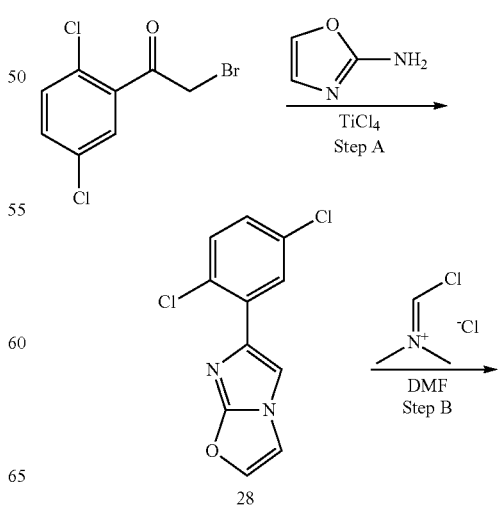

-continued

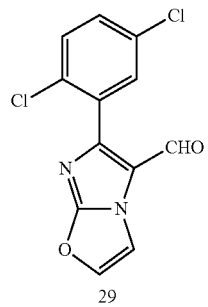 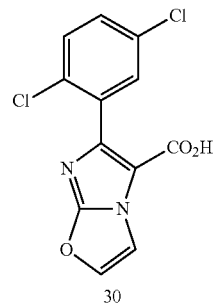

29            30

Step A: A solution of 2-bromo-1-(2,5-dichlorophenyl) ethanone (2.7 g, 10 mmol) and oxazole-2-amine (0.84 g, 10 mmol) in THF (20 mL) and acetonitrile (30 mL) was stirred at room temperature overnight. The suspension was cooled to −10° C. and the solid was collected by vacuum filtration, washed with acetonitrile and dried under vacuum. The solid was suspended in toluene (50 mL) and the suspension was cooled to 0° C. Titanium (IV) chloride (4.7 g, 25 mmol) was added at 0° C. and was then heated to 100° C. for 3 hours. The mixture was cooled to room temperature, toluene was decanted off, and ice was added with stirring to the residue. The mixture was adjusted to pH 9 with the addition of solid $Na_2CO_3$, followed by addition of EtOAc. The mixture was stirred for about 1 hour and then filtered through a pad of Celite. The organic layer was dried over $Na_2SO_4$, filtered and concentrated to give 6-(2,5-dichlorophenyl)imidazo[2,1-b]oxazole (28).

Step B: 6-(2,5-Dichlorophenyl)imidazo[2,1-b]oxazole-5-carbaldehyde (29) was prepared in a similar manner as that described for the synthesis of compound 14 using 6-(2,5-dichlorophenyl)imidazo[2,1-b]oxazole (28) (0.5 g, 2.0 mmol), (chloromethylene)dimethyl ammonium chloride (0.51 g, 4.0 mmol) in DMF (3 mL).

Step C: 6-(2,5-Dichlorophenyl)imidazo[2,1-b]oxazole-5-carboxylic acid (30) was prepared in a similar manner as that described for the synthesis of compound 15 using 6-(2,5-dichlorophenyl)imidazo[2,1-b]oxazole-5-carbaldehyde (29) (0.30 g, 1.07 mmol), 2-methyl-2-butene (2 M in THF, 3.7 mL, 7.4 mmol), sodium phosphate monobasic (0.13 g, 1.07 mmol), and sodium chlorite (80%, 1.2 g, 10.7 mmol) in t-butanol (10 mL) and water (10 mL).

Intermediates 24 and 31-38

Compound 24 was prepared in a similar manner as that described for the synthesis of compound 21. Compounds 31, 32, 33, 34 and 35 were prepared in a similar manner as that described for the synthesis of compound 22. Compounds 36 and 37 were prepared in a similar manner as that described for the synthesis of compound 25. Compound 38 was prepared in a similar manner as that described for the synthesis of compound 23.

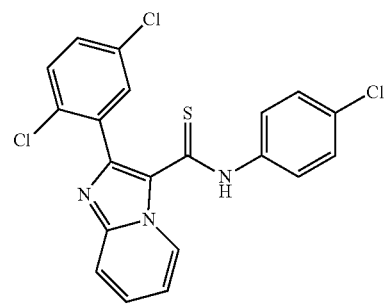

24

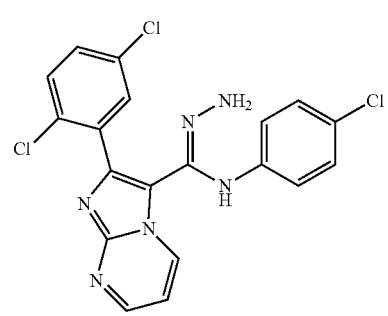

31

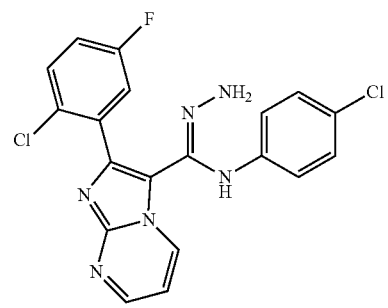

32

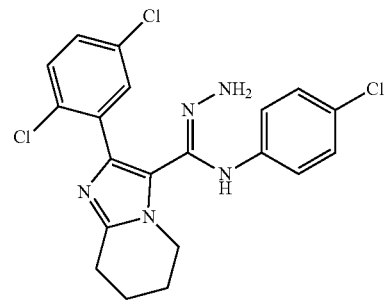

33

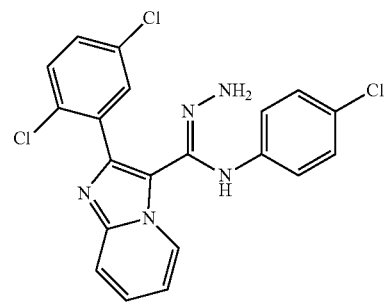

34

-continued

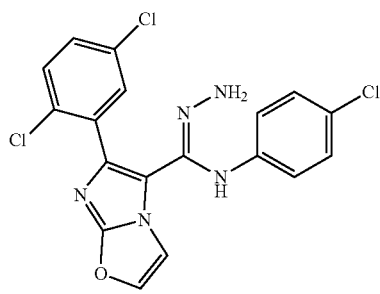

35

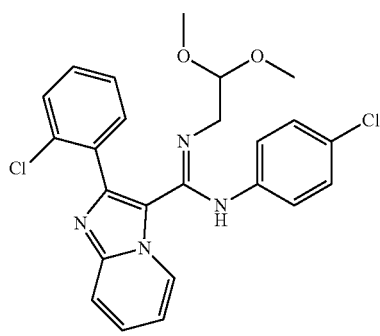

36

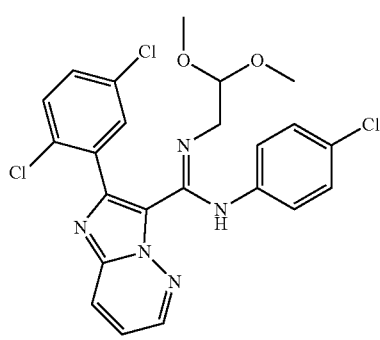

37

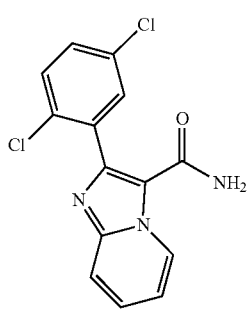

38

Preparation of Examples

Example 1

2-(2-Chlorophenyl)-3-(1-(4-chlorophenyl)-1H-tetrazol-5-yl)imidazo[1,2-a]pyridine (500)

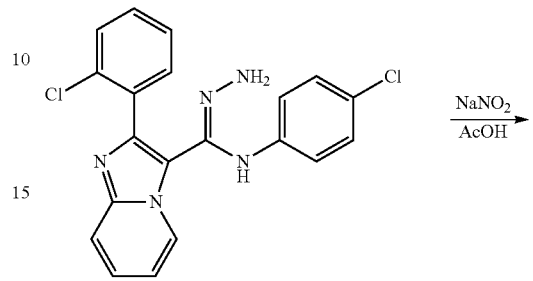

22

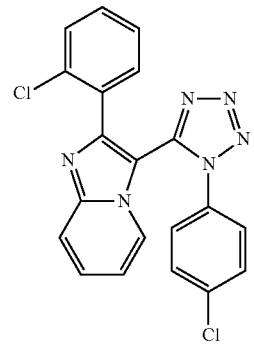

500

To a solution of 2-(2-chlorophenyl)-N-(4-chlorophenyl) imidazo[1,2-a]pyridine-3-carbohydrazonamide (22) (127.6 mg, 0.25 mmol) in acetic acid (2.5 mL) at 0° C. was added a solution of sodium nitrite (17.3 mg, 0.25 mmol) in water (0.25 mL) drop wise. The reaction was stirred at room temperature of 1 hour and was then neutralized with saturated sodium bicarbonate. The solution was extracted with ethyl acetate and the combined organic layers were washed with brine, dried over sodium sulfate, filtered and concentrated in vacuo. The residue was purified by reverse phase HPLC to give 2-(2-chlorophenyl)-3-(1-(4-chlorophenyl)-1H-tetrazol-5-yl)imidazo[1,2-a]pyridine (500). $^1$H NMR (400 MHz, CDCl$_3$) δ 9.00 (d, J=6.9, 1H), 8.03 (d, J=8.6, 1H), 7.67-7.55 (m, 1H), 7.27-6.92 (m, 7H), 6.81 (d, J=8.6, 2H). LC-MS ESI m/z; found 407.0 [M+H]$^+$.

Example 2

2-(2-Chlorophenyl)-3-(4-(4-chlorophenyl)-4H-1,2,4-triazol-3-yl)imidazo[1,2-a]pyridine (501)

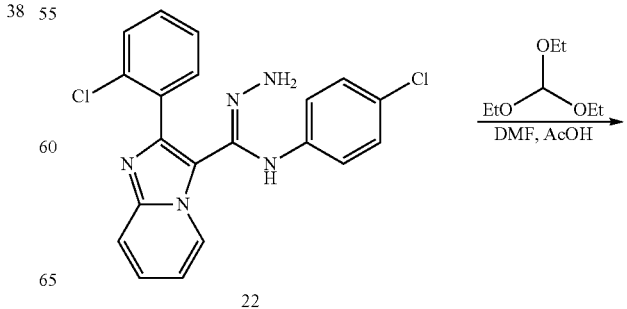

22

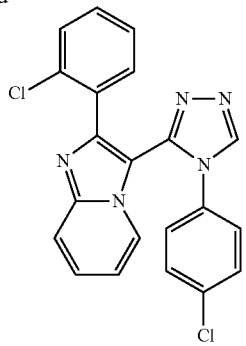

501

To a solution of 1:1 DMF/acetic acid (4.8 mL) was added triethyl orthoformate (0.11 mL, 0.64 mmol), followed by 2-(2-chlorophenyl)-N-(4-chlorophenyl) imidazo[1,2-a]pyridine-3-carbohydrazonamide (22) (230 mg, 0.58 mmol) in DMF (1.0 mL). The reaction was stirred at room temperature for 3 hours and was then concentrated in vacuo. The residue was neutralized with saturated sodium bicarbonate and was extracted with ethyl acetate. The combined organic layers were washed with brine, dried over sodium sulfate, filtered and concentrated in vacuo. The residue was purified by reverse phase HPLC to provide 2-(2-chlorophenyl)-3-(4-(4-chlorophenyl)-4H-1,2,4-triazol-3-yl)imidazo[1,2-a]pyridine (501). $^1$H NMR (400 MHz, CDCl$_3$) δ 9.24 (d, J=6.9, 1H), 8.43 (s, 1H), 8.30 (d, J=9.0, 1H), 7.91-7.82 (m, 1H), 7.44-7.37 (m, 1H), 7.35-7.26 (m, 2H), 7.21-7.15 (m, 1H), 7.12-7.01 (m, 3H), 6.69-6.54 (m, 2H). LC-MS ESI m/z; found 406.1 [M+H]$^+$.

Example 3

3-(4-Cyclohexyl-4H-1,2,4-triazol-3-yl)-2-(2,5-dichlorophenyl)imidazo[1,2-a]pyridine (502)

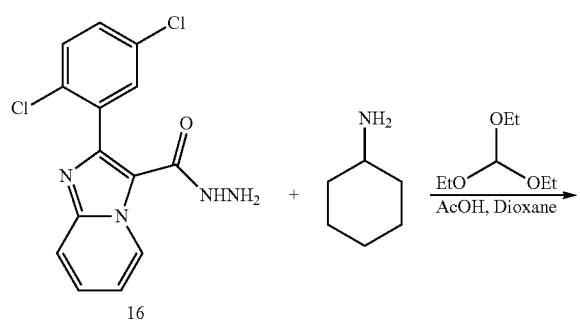

16

502

A solution of 2-(2,5-dichlorophenyl)imidazo[1,2-a]pyridine-3-carbohydrazide (16) (100 mg, 0.31 mmol), cyclohexylamine (153 mg, 1.55 mmol), triethyl orthoformate (0.08 mL, 0.47 mmol), and acetic acid (1 drop) in 1,4-dioxane (3 mL) was heated at 135° C. in a sealed tube overnight. The reaction was concentrated in vacuo and the residue was purified by flash column chromatography on silica gel (0-100% EtOAc in hexanes) to afford 3-(4-cyclohexyl-4H-1,2,4-triazol-3-yl)-2-(2,5-dichlorophenyl)imidazo[1,2-a]pyridine (502). $^1$H NMR (400 MHz, CDCl$_3$) δ 8.64 (d, J=7.1, 1H), 8.29 (s, 1H), 7.77 (d, J=9.0, 1H), 7.46 (s, 1H), 7.42-7.39 (m, 2H), 7.40-7.32 (m, 1H), 6.96 (t, J=6.7, 1H), 3.53 (s, 1H), 1.67-1.59 (m, 2H), 1.31-1.27 (m, 4H), 1.16-0.83 (m, 4H). LC-MS ESI m/z; found 412.1 [M+H]$^+$.

Example 4

2-(2-Chlorophenyl)-3-(1-(4-chlorophenyl)-1H-1,2,4-triazol-5-yl)imidazo[1,2-a]pyridine (503)

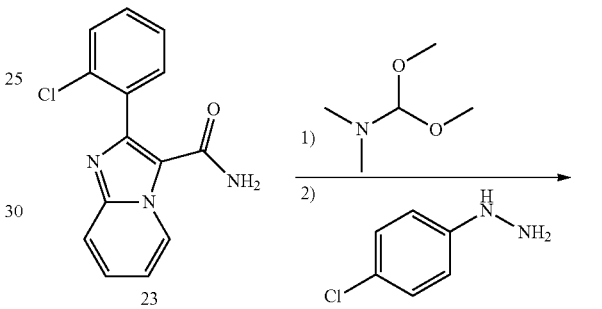

23

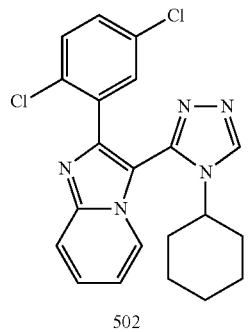

503

A mixture of 2-(2-chlorophenyl)imidazo[1,2-a]pyridine-3-carboxamide (23) (100 mg, 0.37 mmol) in N,N-dimethylformamide dimethyl acetal (3.68 mL) was refluxed for 1 hour. The solvent was removed in vacuo and to the residue was added acetic acid (1.4 mL) and 4-chlorophenylhydrazine (58.9 mg, 0.41 mmol). The reaction was stirred at 95° C. for 2 hours and the solvent was removed in vacuo. The residue was neutralized with saturated sodium bicarbonate and was extracted with ethyl acetate. The combined organic layers were washed with brine, dried over sodium sulfate, filtered and concentrated in vacuo. The residue was purified by flash column chromatography on silica gel (0-50% EtOAc in hexanes) to afford 2-(2-chlorophenyl)-3-(1-(4-chlorophenyl)-1H-1,2,4-triazol-5-yl)imidazo[1,2-a]pyridine (503). $^1$H NMR (400 MHz, CDCl$_3$) δ 9.01 (d, J=7.5, 1H), 8.33 (s, 1H), 8.17 (d, J=9.1, 1H), 7.74-7.60 (m, 1H), 7.26-7.19 (m, 3H), 7.18-7.00 (m, 4H), 6.85-6.75 (m, 2H). LC-MS ESI m/z; found 406.1 [M+H]$^+$.

Example 5

3-(1-(4-Chlorophenyl)-3-methyl-1H-1,2,4-triazol-5-yl)-2-(2,5-dichlorophenyl)imidazo[1,2-a]pyridine (504)

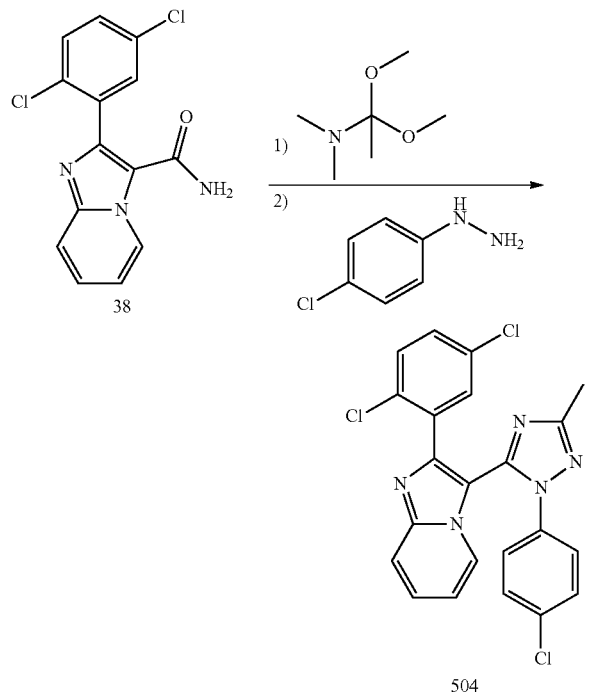

A mixture of 2-(2,5-dichlorophenyl)imidazo[1,2-a]pyridine-3-carboxamide (38) (154 mg, 0.50 mmol) in N,N-dimethylacetamide dimethyl acetal (5 mL) was refluxed for 1 hour. The solvent was removed in vacuo and to the residue was added acetic acid (2.5 mL) and 4-chlorophenylhydrazine (108.3 mg, 0.76 mmol). The reaction was stirred at 95° C. for 2 hours and the solvent was removed in vacuo. The residue was neutralized with saturated sodium bicarbonate and was extracted with ethyl acetate. The combined organic layers were washed with brine, dried over sodium sulfate, filtered and concentrated in vacuo. The residue was purified by reverse phase HPLC to yield 3-(1-(4-chlorophenyl)-3-methyl-1H-1,2,4-triazol-5-yl)-2-(2,5-dichlorophenyl)imidazo[1,2-a]pyridine (504). $^1$H NMR (400 MHz, CDCl$_3$) δ 8.93 (d, J=7.0, 1H), 7.76 (d, J=9.1, 1H), 7.51-7.36 (m, 1H), 7.17-7.03 (m, 5H), 7.02-6.96 (m, 1H), 6.86-6.75 (m, 2H), 2.59 (s, 3H). LC-MS ESI m/z; found 454.0 [M+H]$^+$.

Example 6

3-(4-(4-Chlorophenyl)-5-methyl-4H-1,2,4-triazol-3-yl)-2-(2,5-dichlorophenyl)imidazo[1,2-a]pyridine (505)

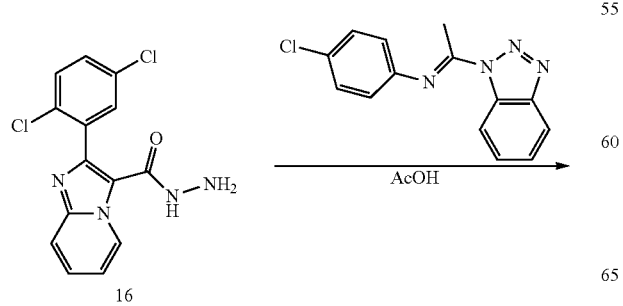

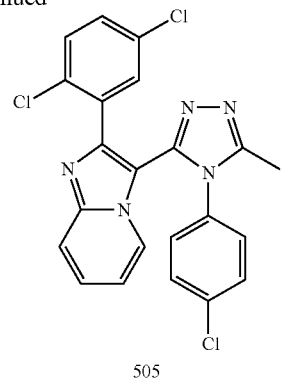

To a solution of 2-(2,5-dichlorophenyl)imidazo[1,2-a]pyridine-3-carbohydrazide (16) (112.4 mg, 0.35 mmol) and N-(1-(1H-benzo[d][1,2,3]triazol-1-yl)ethylidene)-4-chloroaniline (synthesized according to the protocol described in Journal of Organic Chemistry, 2006, 71(9), 3375-3380) (947.5 mg, 3.50 mmol) in DMF (1.75 mL) was added two drops of acetic acid. The reaction was stirred at 120° C. for 24 hours and was then purified directly by reverse phase HPLC to yield 3-(4-(4-chlorophenyl)-5-methyl-4H-1,2,4-triazol-3-yl)-2-(2,5-dichlorophenyl)imidazo[1,2-a]pyridine (505). $^1$H NMR (400 MHz, CDCl$_3$) δ 9.16-9.01 (m, 1H), 7.96-7.73 (m, 1H), 7.56-7.44 (m, 1H), 7.25-7.16 (m, 2H), 7.16-7.06 (m, 3H), 7.00 (s, 1H), 6.58-6.46 (m, 2H), 2.39 (s, 3H). LC-MS ESI m/z; found 454.0 [M+H]$^+$.

Example 7

3-(1-(4-Chlorophenyl)-1H-imidazol-2-yl)-2-(2,5-dichlorophenyl)imidazo[1,2-a]pyridine (506)

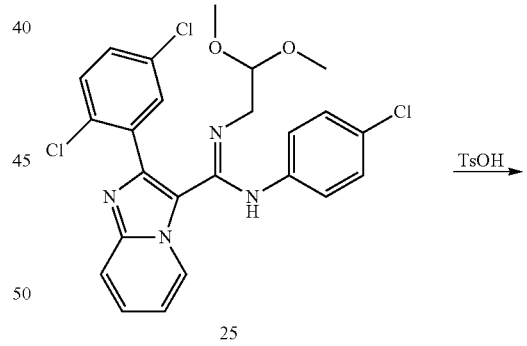

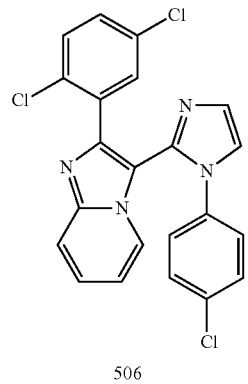

A mixture of N-(4-chlorophenyl)-2-(2,5-dichlorophenyl)-N-(2,2-dimethoxyethyl)imidazo[1,2-a]pyridine-3-carboximidamide (25) (125 mg, 0.25 mmol) in acetic acid was refluxed for 2 hours. The solvent was removed in vacuo and the residue was dissolved in ethyl acetate. The organic layer was washed with water, brine, dried over sodium sulfate, filtered and concentrated in vacuo. The residue was purified by reverse phase HPLC to yield 3-(1-(4-chlorophenyl)-1H-imidazol-2-yl)-2-(2,5-dichlorophenyl)imidazo[1,2-a]pyridine (506). $^1$H NMR (400 MHz, CDCl$_3$) δ 9.00 (d, J=6.9, 1H), 7.91-7.80 (m, 1H), 7.53-7.42 (m, 2H), 7.20-7.03 (m, 6H), 6.98-6.94 (m, 1H), 6.67-6.54 (m, 2H). LC-MS ESI m/z; found 439.0 [M+H]$^+$.

Example 8

3-(1-(4-Chlorophenyl)-1H-imidazol-5-yl)-2-(2,5-dichlorophenyl)imidazo[1,2-a]pyridine (507)

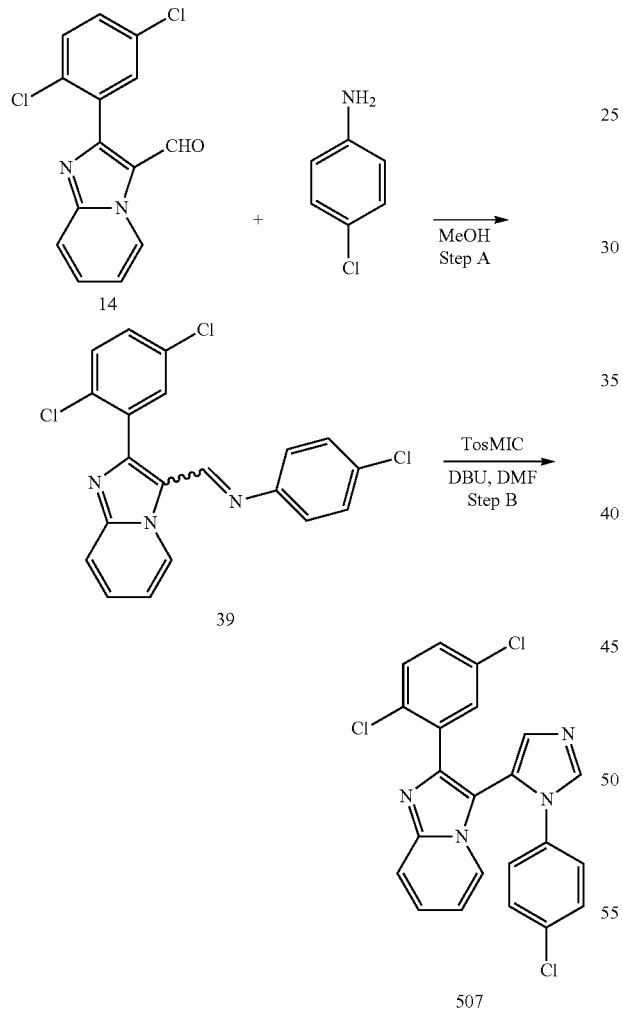

Step A: A solution of 2-(2,5-dichlorophenyl)imidazo[1,2-a]pyridine-3-carbaldehyde (14) (400 mg, 1.37 mmol), 4-chloroaniline (175 mg, 1.37 mmol), and methanol (14 mL) was refluxed overnight. The yellow precipitate that formed was filtered and washed with methanol to provide 4-chloro-N-((2-(2,5-dichlorophenyl)imidazo[1,2-a]pyridin-3-yl)methylene)aniline (39).

Step B: A solution of 4-chloro-N-((2-(2,5-dichlorophenyl)imidazo[1,2-a]pyridin-3-yl)methylene)aniline (39) (200 mg, 0.50 mmol), toluenesulfonylmethyl isocyanide (TosMIC) (97.5 mg, 0.50 mmol), 1,8-diazabicyclo[5.4.0]undec-7-ene (DBU) (0.15 mL, 1.0 mmol) in DMF (5 mL) was heated at 90° C. overnight. The reaction mixture was directly injected into the reverse phase HPLC and purified to yield 3-(1-(4-chlorophenyl)-1H-imidazol-5-yl)-2-(2,5-dichlorophenyl)imidazo[1,2-a]pyridine (507). $^1$H NMR (400 MHz, DMSO-d$_6$) δ 8.35 (d, J=6.9, 1H), 8.11 (s, 1H), 7.67 (d, J=9.1, 1H), 7.56 (s, 1H), 7.41-7.36 (m, 3H), 7.24 (d, J=8.7, 2H), 7.00 (d, J=6.9, 1H), 6.89 (s, 1H), 6.77 (d, J=8.7, 2H). LC-MS ESI m/z; found 439.0 [M+H]$^+$.

Additional representative compounds of the invention, shown below, were prepared by following procedures described in the above examples using appropriate starting materials, as would be apparent to those skilled in the art.

Example 9

2-(2,5-Dichlorophenyl)-3-(4-(pyridin-4-yl)-4H-1,2,4-triazol-3-yl)imidazo[1,2-a]pyridine (508)

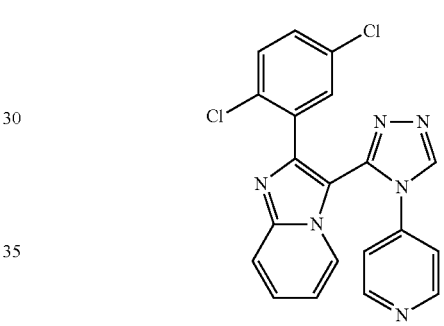

$^1$H NMR (400 MHz, CDCl$_3$) δ 9.05 (d, J=6.9, 1H), 8.45 (d, J=5.8, 2H), 8.37 (s, 1H), 7.77 (d, J=9.3, 1H), 7.43-7.45 (m, 1H), 7.13-7.01 (m, 3H), 6.96 (s, 1H), 6.70 (d, J=5.8, 2H). LC-MS ESI m/z; found 407.1 [M+H]$^+$.

Example 10

2-(2,5-Dichlorophenyl)-3-(4-isopropyl-4H-1,2,4-triazol-3-yl)imidazo[1,2-a]pyridine (509)

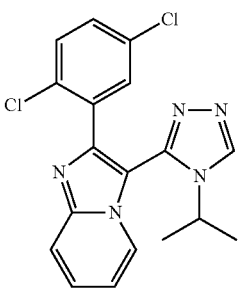 [SMILES: CC(C)n1cnnc1-c1c(-c2cc(Cl)ccc2Cl)nc2ccccn12]

$^1$H NMR (400 MHz, CDCl$_3$) δ 8.58 (d, J=7.0, 1H), 8.33 (s, 1H), 7.76 (d, J=9.0, 1H), 7.53 (s, 1H), 7.41-7.39 (m, 2H), 7.35-7.31 (m, 1H), 6.99-6.95 (m, 1H), 3.94 (septet, 1H), 1.05 (d, J=6.6, 6H). LC-MS ESI m/z; found 372.1 [M+H]$^+$.

Example 11

4-(3-(2-(2,5-Dichlorophenyl)imidazo[1,2-a]pyridin-3-yl)-4H-1,2,4-triazol-4-yl)-N,N-dimethylaniline (510)

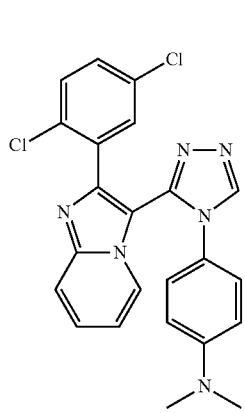 [SMILES: CN(C)c1ccc(-n2cnnc2-c2c(-c3cc(Cl)ccc3Cl)nc3ccccn23)cc1]

¹H NMR (400 MHz, CDCl₃) δ 9.07 (d, J=6.2, 1H), 8.29 (s, 1H), 7.72 (d, J=9.4, 1H), 7.42-7.39 (m, 1H), 7.17-6.93 (m, 4H), 6.50 (d, J=9.0, 2H), 6.29 (d, J=9.0, 2H), 2.94 (s, 6H). LC-MS ESI m/z; found 449.1 [M+H]⁺.

Example 12

4-(4-(3-(2-(2,5-Dichlorophenyl)imidazo[1,2-a]pyridin-3-yl)-4H-1,2,4-triazol-4-yl)phenyl)morpholine (511)

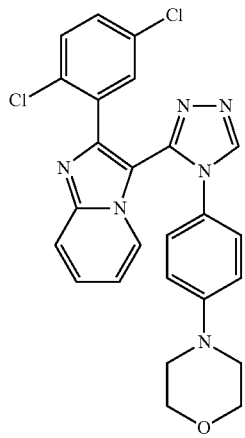 [SMILES: Clc1ccc(Cl)c(-c2nc3ccccn3c2-c2nncn2-c2ccc(N3CCOCC3)cc2)c1]

¹H NMR (400 MHz, CDCl₃) δ 9.05 (d, J=9.2, 1H), 8.29 (s, 1H), 7.73 (d, J=9.2, 1H), 7.44-7.38 (m, 1H), 7.11-6.98 (m, 4H), 6.63-6.44 (m, 4H), 3.85-3.83 (m, 4H), 3.16-3.12 (m, 4H). LC-MS ESI m/z; found 491.1 [M+H]⁺.

Example 13

2-(2,5-Dichlorophenyl)-3-(4-(4-(methylsulfonyl)phenyl)-4H-1,2,4-triazol-3-yl)imidazo[1,2-a]pyridine (512)

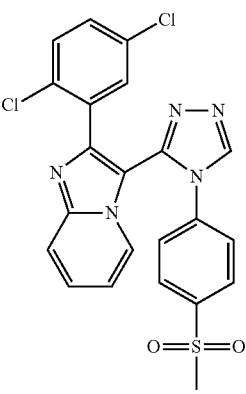 [SMILES: CS(=O)(=O)c1ccc(-n2cnnc2-c2c(-c3cc(Cl)ccc3Cl)nc3ccccn23)cc1]

¹H NMR (400 MHz, CDCl₃) δ 9.10-9.03 (m, 1H), 8.37 (s, 1H), 7.75-7.74 (m, 3H), 7.49-7.44 (m, 1H), 7.14-7.09 (m, 3H), 7.04 (s, 1H), 6.97 (d, J=8.5, 2H), 3.10 (s, 3H). LC-MS ESI m/z; found 484.0 [M+H]⁺.

Example 14

2-(2,5-Dichlorophenyl)-3-(4-(4-(trifluoromethyl)phenyl)-4H-1,2,4-triazol-3-yl)imidazo[1,2-a]pyridine (513)

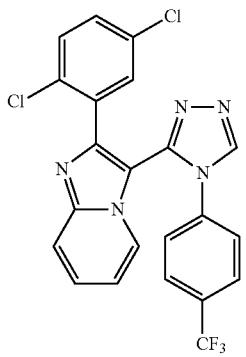 [SMILES: FC(F)(F)c1ccc(-n2cnnc2-c2c(-c3cc(Cl)ccc3Cl)nc3ccccn23)cc1]

¹H NMR (400 MHz, CDCl₃) δ 9.09 (d, J=7.1, 1H), 8.36 (s, 1H), 7.76 (d, J=9.2, 1H), 7.47-7.41 (m, 3H), 7.13-7.06 (m, 3H), 6.95 (s, 1H), 6.88 (d, J=8.1, 2H). LC-MS ESI m/z; found 474.10 [M+H]⁺.

Example 15

5-(3-(2-(2,5-Dichlorophenyl)imidazo[1,2-a]pyridin-3-yl)-4H-1,2,4-triazol-4-yl)-1H-indazole (514)

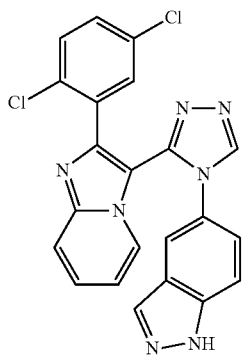 [SMILES: Clc1ccc(Cl)c(-c2nc3ccccn3c2-c2nncn2-c2ccc3[nH]ncc3c2)c1]

$^1$H NMR (400 MHz, CDCl$_3$) δ 9.14 (d, J=6.6, 1H), 8.40 (s, 1H), 7.94 (s, 1H), 7.73 (d, J=9.2, 1H), 7.46-7.44 (m, 1H), 7.27-7.25 (m, 1H), 7.17 (s, 1H), 7.09-7.06 (m, 1H), 7.01-6.99 (m, 1H), 6.91-6.89 (m, 1H), 6.71-6.68 (m, 2H). LC-MS ESI m/z; found 446.10 [M+H]$^+$.

Example 16

4-(3-(2-(2,5-Dichlorophenyl)imidazo[1,2-a]pyridin-3-yl)-4H-1,2,4-triazol-4-yl)benzonitrile (515)

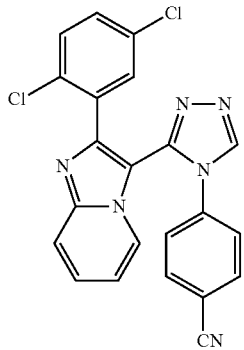 [SMILES: N#Cc1ccc(-n2cnnc2-c2c(-c3cc(Cl)ccc3Cl)nc3ccccn23)cc1]

$^1$H NMR (400 MHz, CDCl$_3$) δ 9.01 (d, J=6.8, 1H), 8.28 (s, 1H), 7.70 (d, J=9.0, 1H), 7.42-7.39 (m, 3H), 7.13-6.97 (m, 3H), 6.83 (s, 1H), 6.79 (d, J=8.3, 2H). LC-MS ESI m/z; found 431.2 [M+H]$^+$.

Example 17

6-(3-(2-(2,5-Dichlorophenyl)imidazo[1,2-a]pyridin-3-yl)-4H-1,2,4-triazol-4-yl)-1H-indazole (516)

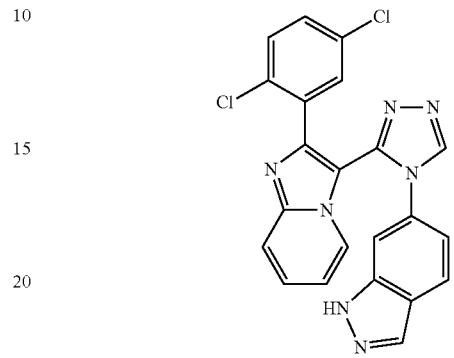

$^1$H NMR (400 MHz, CDCl$_3$) δ 9.13 (d, J=7.2, 1H), 8.41 (s, 1H), 8.10 (s, 1H), 7.74 (d, J=9.0, 1H), 7.53 (d, J=8.5, 1H), 7.46-7.44 (m, 1H), 7.09-7.06 (m, 1H), 6.93-6.89 (m, 3H), 6.73 (s, 1H), 6.51 (d, J=8.5, 1H). LC-MS ESI m/z; found 446.1 [M+H]$^+$.

Example 18

6-(3-(2-(2,5-Dichlorophenyl)imidazo[1,2-a]pyridin-3-yl)-4H-1,2,4-triazol-4-yl)-1-methyl-1H-benzo[d]imidazole (517)

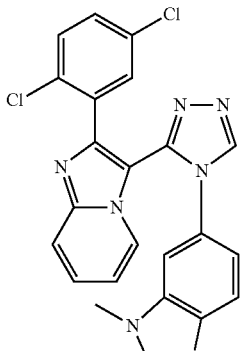

$^1$H NMR (400 MHz, CDCl$_3$) δ 9.15 (d, J=6.9, 1H), 8.40 (s, 1H), 7.93 (s, 1H), 7.73 (d, J=8.8, 1H), 7.56 (d, J=8.8, 1H), 7.47-7.37 (m, 1H), 7.09-7.06 (m, 1H), 6.94 (s, 2H), 6.77-6.75 (m, 2H), 6.60 (d, J=6.4, 1H), 3.71 (s, 3H). LC-MS ESI m/z; found 460.1 [M+H]$^+$.

Example 19

5-(3-(2-(2,5-Dichlorophenyl)imidazo[1,2-a]pyridin-3-yl)-4H-1,2,4-triazol-4-yl)benzo[d]thiazole (518)

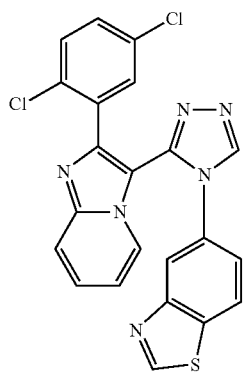 [SMILES: Clc1ccc(Cl)c(-c2nc3ccccn3c2-c2nncn2-c2ccc3scnc3c2)c1]

¹H NMR (400 MHz, CDCl₃) δ 9.15 (d, J=6.6, 1H), 9.09 (s, 1H), 8.43 (s, 1H), 7.75-7.71 (m, 2H), 7.51 (s, 1H), 7.47-7.44 (m, 1H), 7.09-7.06 (m, 1H), 7.02-7.00 (m, 1H), 6.92 (d, J=8.7, 1H), 6.81-6.68 (m, 2H). LC-MS ESI m/z; found 463.0 [M+H]⁺.

Example 20

5-(3-(2-(2,5-Dichlorophenyl)imidazo[1,2-a]pyridin-3-yl)-4H-1,2,4-triazol-4-yl)-1-methyl-1H-indazole (519)

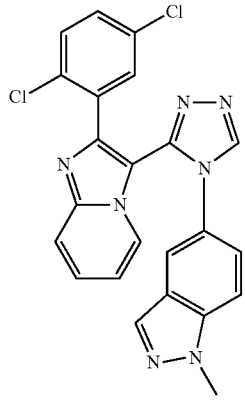 [SMILES: Cn1ncc2cc(-n3cnnc3-c3c(-c4cc(Cl)ccc4Cl)nc4ccccn34)ccc21]

¹H NMR (400 MHz, CDCl₃) δ 9.17 (d, J=6.6, 1H), 8.39 (s, 1H), 7.83 (s, 1H), 7.72 (d, J=9.1, 1H), 7.44 (t, J=7.8, 1H), 7.16-6.97 (m, 4H), 6.87 (d, J=8.6, 1H), 6.67-6.65 (m, 2H), 4.08 (s, 3H). LC-MS ESI m/z; found 460.1 [M+H]⁺.

Example 21

6-(3-(2-(2,5-Dichlorophenyl)imidazo[1,2-a]pyridin-3-yl)-4H-1,2,4-triazol-4-yl)-1-methyl-1H-indazole (520)

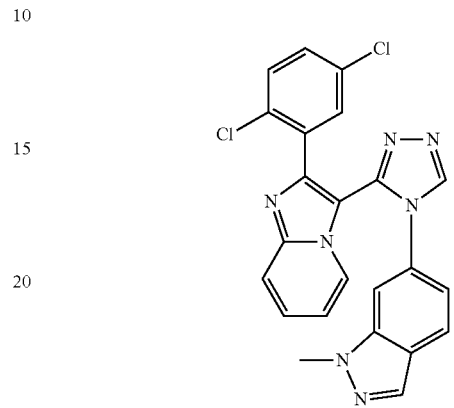

¹H NMR (400 MHz, CDCl₃) δ 9.17 (d, J=7.1, 1H), 8.41 (s, 1H), 7.99 (s, 1H), 7.73 (d, J=8.4, 1H), 7.51 (d, J=8.4, 1H), 7.46-7.43 (m, 1H), 7.10-7.07 (m, 1H), 6.91-6.89 (m, 2H), 6.75 (d, J=7.1, 2H), 6.44 (d, J=8.5, 1H), 3.95 (s, 3H). LC-MS ESI m/z; found 460.1 [M+H]⁺.

Example 22

5-(3-(2-(2,5-Dichlorophenyl)imidazo[1,2-a]pyridin-3-yl)-4H-1,2,4-triazol-4-yl)-1-methyl-1H-benzo[d]imidazole (521)

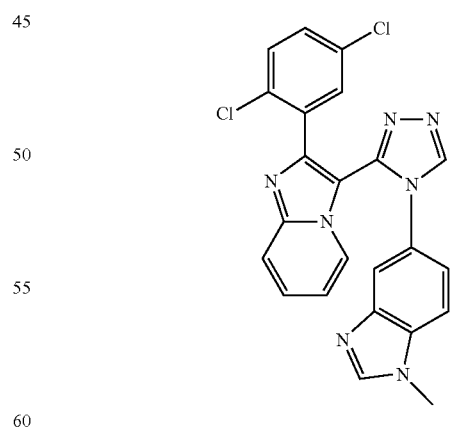

¹H NMR (400 MHz, CDCl₃) δ 9.16 (d, J=7.1, 1H), 8.40 (s, 1H), 7.92 (s, 1H), 7.70 (d, J=8.9, 1H), 7.44-7.42 (m, 1H), 7.16 (s, 1H), 7.11-7.04 (m, 3H), 6.89 (d, J=8.6, 1H), 6.62-6.58 (m, 2H), 3.86 (s, 3H). LC-MS ESI m/z; found 460.1 [M+H]⁺.

Example 23

6-(3-(2-(2-Chlorophenyl)imidazo[1,2-a]pyridin-3-yl)-4H-1,2,4-triazol-4-yl)-1H-indazole (522)

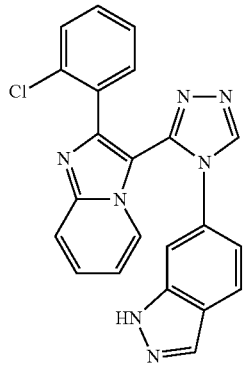 [SMILES: Clc1ccccc1-c1nc2ccccn2c1-c1nncn1-c1ccc2cn[nH]c2c1]

$^1$H NMR (400 MHz, CDCl$_3$) δ 10.80 (br, 1H), 9.06 (d, J=7.0, 1H), 8.36 (s, 1H), 8.04 (s, 1H), 7.75 (d, J=8.6, 1H), 7.52-7.33 (m, 2H), 7.05-7.01 (s, 1H), 6.94-6.89 (m, 2H), 6.82-6.78 (m, 2H), 6.68-6.64 (m, 1H), 6.45 (d, J=8.6, 1H). LC-MS ESI m/z; found 412.1 [M+H]$^+$.

Example 24

3-(4-(1H-Indazol-6-yl)-4H-1,2,4-triazol-3-yl)-2-(2,5-dichlorophenyl)imidazo[1,2-b]pyridazine (523)

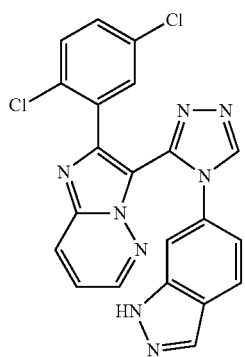 [SMILES: Clc1ccc(Cl)c(-c2nc3cccnn3c2-c2nncn2-c2ccc3cn[nH]c3c2)c1]

$^1$H NMR (400 MHz, DMSO-d$_6$) δ13.10 (br, 1H), 9.16 (s, 1H), 8.43 (s, 1H), 8.27 (d, J=9.1, 1H), 8.07 (s, 1H), 7.65 (d, J=8.4, 1H), 7.43-7.34 (m, 3H), 7.19 (s, 1H), 7.11 (s, 1H), 6.74 (d, J=8.7, 1H). LC-MS ESI m/z; found 447.1 [M+H]$^+$.

Example 25

3-(4-(4-Chlorophenyl)-4H-1,2,4-triazol-3-yl)-2-(4-fluorophenyl)pyrazolo[1,5-a]pyridine (524)

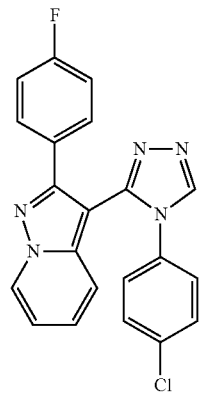 [SMILES: Fc1ccc(-c2nn3ccccc3c2-c2nncn2-c2ccc(Cl)cc2)cc1]

$^1$H NMR (400 MHz, CDCl$_3$) δ 8.50 (d, J=6.9, 1H), 8.32 (s, 1H), 7.85 (d, J=9.1, 1H), 7.34 (t, J=7.6, 1H), 7.19-7.04 (m, 4H), 7.02-6.81 (m, 3H), 6.58 (d, J=8.6, 2H). LC-MS ESI m/z; found 390.1 [M+H]$^+$.

Example 26

4-(4-Chlorophenyl)-3-(2-(2,5-dichlorophenyl)imidazo[1,2-a]pyridin-3-yl)-1H-1,2,4-triazol-5(4H)-one (525)

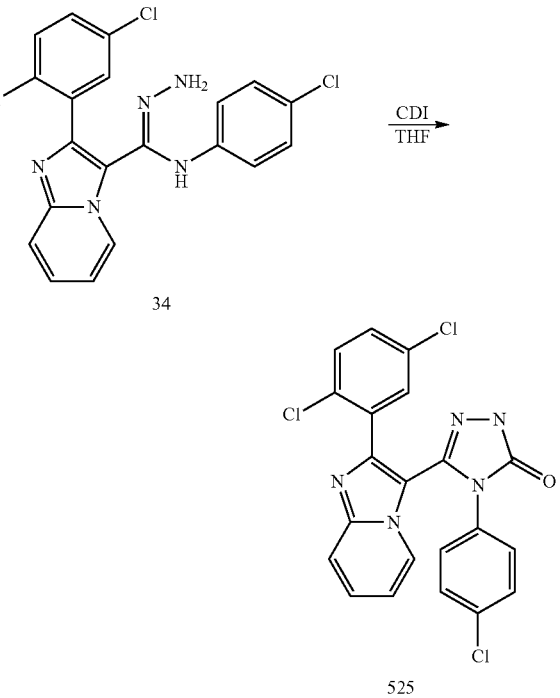

To a mixture of N-(4-chlorophenyl)-2-(2,5-dichlorophenyl)imidazo[1,2-a]pyridine-3-carbohydrazonamide (34) (107.7 mg, 0.25 mmol) in THF (2.5 mL) was added 1,1'-carbonyldiimidazole (CDI) (48.7 mg, 0.30 mmol). After the reaction was stirred at room temperature for 15 hours, ethyl acetate was added and the solution was washed with water and brine. The organic layer was dried over sodium sulfate, filtered, and concentrated in vacuo. The residue was purified by reverse phase HPLC to provide 4-(4-chlorophenyl)-3-(2-(2,5-dichlorophenyl)imidazo[1,2-a]pyridin-3-yl)-1H-1,2,4-triazol-5(4H)-one (525). $^1$H NMR (400 MHz, DMSO-$d_6$) δ 12.59 (s, 1H), 8.83 (d, J=7.0, 1H), 7.73 (d, J=9.0, 1H), 7.57-7.47 (m, 1H), 7.42-7.36 (m, 2H), 7.24-7.11 (m, 3H), 6.87-6.80 (m, 1H), 6.77-6.69 (m, 2H). LC-MS ESI m/z; found 456.0 [M+H]$^+$.

Example 27

4-(4-Chlorophenyl)-3-(2-(2,5-dichlorophenyl)imidazo[1,2-a]pyridin-3-yl)-1H-1,2,4-triazole-5(4H)-thione (526)

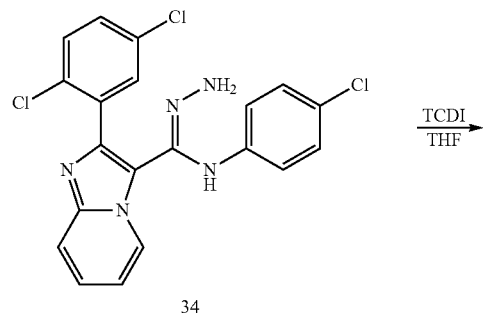

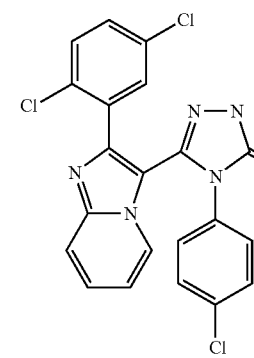

4-(4-Chlorophenyl)-3-(2-(2,5-dichlorophenyl)imidazo[1,2-a]pyridin-3-yl)-1H-1,2,4-triazole-5(4H)-thione (526) was prepared in a similar manner as that described for the synthesis of compound 525 using N-(4-chlorophenyl)-2-(2,5-dichlorophenyl)imidazo[1,2-a]pyridine-3-carbohydrazonamide (34) (107.7 mg, 0.25 mmol), 1,1'-thiocarbonyldiimidazole (53.5 mg, 0.30 mmol) and THF (2.5 mL). $^1$H NMR (400 MHz, CDCl$_3$) δ 11.94 (br, 1H), 8.91-8.69 (m, 1H), 8.12-7.85 (m, 1H), 7.67-7.51 (m, 1H), 7.26-7.06 (m, 5H), 7.03-6.98 (m, 1H), 6.74-6.64 (m, 2H). LC-MS ESI m/z; found 472.0 [M+H]$^+$.

Example 28

3-(4-(4-Chlorophenyl)-5-methoxy-4H-1,2,4-triazol-3-yl)-2-(2,5-dichlorophenyl)imidazo[1,2-a]pyridine (527)

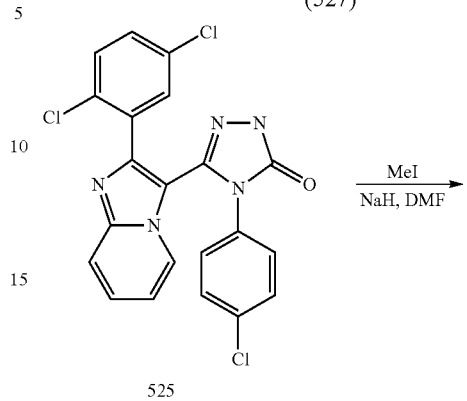

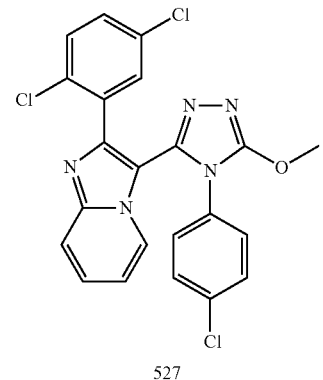

To a solution of 4-(4-chlorophenyl)-3-(2-(2,5-dichlorophenyl)imidazo[1,2-a]pyridin-3-yl)-1H-1,2,4-triazol-5(4H)-one (525) (53.4 mg, 0.12 mmol) in DMF (1.2 mL) was added sodium hydride (60% in mineral oil, 9.3 mg, 0.23 mmol) followed by methyl iodide (14.5 µL, 0.23 mmol). The reaction was stirred at 70° C. for 3 hours, filtered and purified directly by reverse phase HPLC to yield 3-(4-(4-Chlorophenyl)-5-methoxy-4H-1,2,4-triazol-3-yl)-2-(2,5-dichlorophenyl)imidazo[1,2-a]pyridine (527). $^1$H NMR (400 MHz, CDCl$_3$) δ 8.84 (d, J=6.9, 1H), 7.77 (d, J=8.9, 1H), 7.51-7.37 (m, 1H), 7.19 (s, 2H), 7.11-7.03 (m, 3H), 6.98-6.92 (m, 1H), 6.66-6.58 (m, 2H), 3.69 (s, 3H). LC-MS ESI m/z; found 470.0 [M+H]$^+$.

Example 29

3-(4-(4-Chlorophenyl)-5-(methylthio)-4H-1,2,4-triazol-3-yl)-2-(2,5-dichlorophenyl)imidazo[1,2-a]pyridine (528)

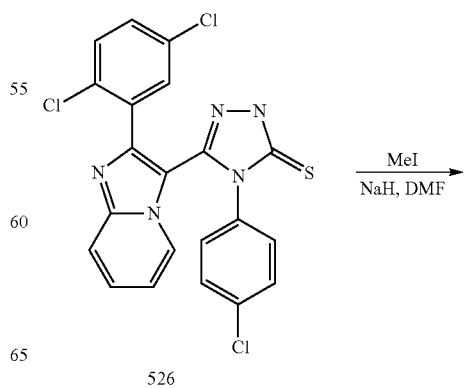

-continued

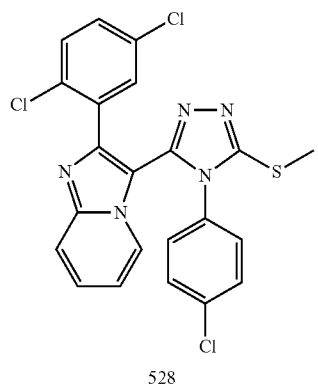

528

3-(4-(4-Chlorophenyl)-5-(methylthio)-4H-1,2,4-triazol-3-yl)-2-(2,5-dichlorophenyl)imidazo[1,2-a]pyridine (528) was prepared in a similar manner as that described for the synthesis of compound 527 using 4-(4-chlorophenyl)-3-(2-(2,5-dichlorophenyl)imidazo[1,2-a]pyridin-3-yl)-1H-1,2,4-triazole-5(4H)-thione (526) (90.0 mg, 0.19 mmol), sodium hydride (60% in mineral oil, 8.4 mg, 0.21 mmol) and methyl iodide (13.1 μL, 0.21 mmol) and DMF (1.9 mL). $^1$H NMR (400 MHz, DMSO-$d_6$) δ 8.88 (d, J=7.0, 1H), 7.72 (d, J=9.0, 1H), 7.55-7.46 (m, 1H), 7.42-7.32 (m, 2H), 7.25-7.13 (m, 3H), 6.84-6.76 (m, 3H), 2.65 (s, 3H). LC-MS ESI m/z; found 486.0 [M+H]$^+$.

Example 30

2-(2,5-Dichlorophenyl)-3-(4-(4-ethylphenyl)-4H-1,2,4-triazol-3-yl)imidazo[1,2-a]pyridine (529)

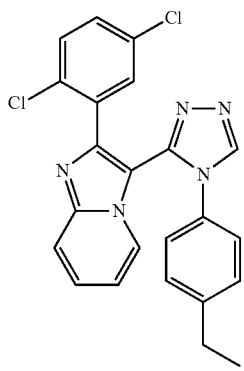 [SMILES: CCc1ccc(-n2cnnc2-c2c(-c3cc(Cl)ccc3Cl)nc3ccccn23)cc1]

$^1$H NMR (400 MHz, CDCl$_3$) δ: 9.02 (d, J=6.8 Hz, 1H), 8.30 (s, 1H), 7.71 (d, J=9.2 Hz, 1H), 7.43-7.39 (m, 1H), 7.08-7.01 (m, 3H), 6.93-6.91 (m, 3H), 6.58 (d, J=8.0 Hz, 2H), 2.65-2.59 (m, 2H), 1.26-1.18 (m, 3H). LC-MS ESI m/z; found 434.1 [M+H]$^+$.

Example 31

2-(2,5-Dichlorophenyl)-3-(4-(4-isopropylphenyl)-4H-1,2,4-triazol-3-yl)imidazo[1,2-a]pyridine (530)

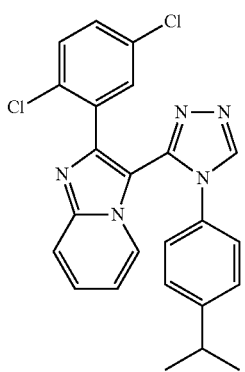 [SMILES: CC(C)c1ccc(-n2cnnc2-c2c(-c3cc(Cl)ccc3Cl)nc3ccccn23)cc1]

$^1$H NMR (400 MHz, CDCl$_3$) δ: 9.00 (d, J=7.2 Hz, 1H), 8.30 (s, 1H), 7.70 (d, J=8.8 Hz, 1H), 7.40-7.37 (m, 1H), 7.06-6.93 (m, 6H), 6.59 (d, J=8.4 Hz, 2H), 2.86-2.83 (m, 1H), 1.18 (d, J=7.2 Hz, 6H). LC-MS ESI m/z; found 448.1 [M+H]$^+$.

Example 32

3-(4-([1,1'-Biphenyl]-4-yl)-4H-1,2,4-triazol-3-yl)-2-(2,5-dichlorophenyl)imidazo[1,2-a]pyridine (531)

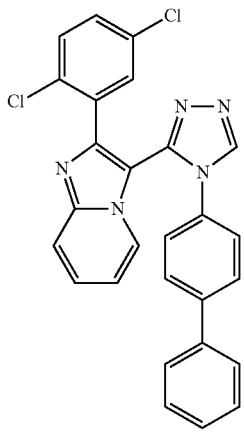 [SMILES: Clc1ccc(Cl)c(-c2nc3ccccn3c2-c2nncn2-c2ccc(-c3ccccc3)cc2)c1]

$^1$H NMR (400 MHz, CDCl$_3$) δ: 9.09 (d, J=6.8 Hz, 1H), 8.37 (s, 1H), 7.74 (d, J=8.8 Hz, 1H), 7.52-7.31 (m, 8H), 7.07-6.96 (m, 4H), 6.78 (d, J=8.0 Hz, 2H). LC-MS ESI m/z; found 482.1 [M+H]$^+$.

Example 33

Ethyl 4-(3-(2,5-dichlorophenyl)imidazo[1,2-a]pyridine-3-yl)-4H-1,2,4-triazol-4-yl)benzoate (532)

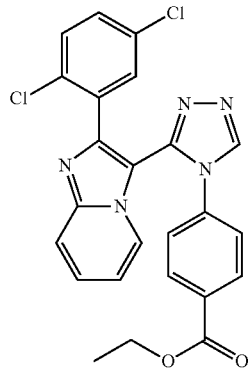 [SMILES: CCOC(=O)c1ccc(-n2cnnc2-c2c(-c3cc(Cl)ccc3Cl)nc3ccccn23)cc1]

¹H NMR (400 MHz, CDCl₃) δ: 9.08 (d, J=6.8 Hz, 1H), 8.36 (s, 1H), 7.81 (d, J=8.8 Hz, 2H), 7.73 (d, J=8.8 Hz, 1H), 7.46-7.42 (m, 1H), 7.09-7.05 (m, 3H), 6.85 (s, 1H), 6.77 (d, J=8.0 Hz, 2H), 4.42-4.37 (m, 2H), 1.42-1.38 (m, 3H). LC-MS ESI m/z; found 478.1 [M+H]⁺.

Example 34

2-(2,5-Dichlorophenyl)-3-(4-(4-fluorophenyl)-4H-1,2,4-triazol-3-yl)imidazo[1,2-a]pyridine (533)

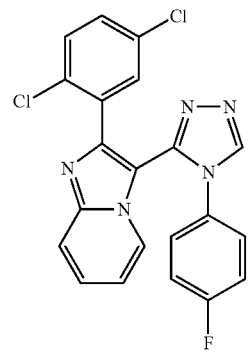 [SMILES: Fc1ccc(-n2cnnc2-c2c(-c3cc(Cl)ccc3Cl)nc3ccccn23)cc1]

¹H NMR (400 MHz, CDCl₃) δ: 9.05 (d, J=7.2 Hz, 1H), 8.31 (s, 1H), 7.72 (d, J=9.2 Hz, 1H), 7.44-7.40 (m, 1H), 7.14 (m, 2H), 7.06-7.03 (m, 1H), 6.94 (s, 1H), 6.85-6.81 (m, 2H), 6.70-6.67 (m, 2H). LC-MS ESI m/z; found 424.1 [M+H]⁺.

Example 35

2-(2,5-Dichlorophenyl)-3-(4-(2-fluorophenyl)-4H-1,2,4-triazol-3-yl)imidazo[1,2-a]pyridine (534)

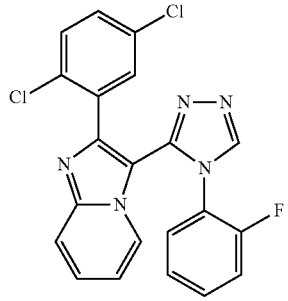 [SMILES: Fc1ccccc1-n1cnnc1-c1c(-c2cc(Cl)ccc2Cl)nc2ccccn12]

¹H NMR (400 MHz, CDCl₃) δ: 9.03 (d, J=7.2 Hz, 1H), 8.34 (s, 1H), 7.72 (d, J=8.8 Hz, 1H), 7.45-7.41 (m, 1H), 7.31-7.26 (m, 1H), 7.18-7.03 (m, 3H), 6.92-6.86 (m, 3H), 6.69-6.67 (m, 1H). LC-MS ESI m/z; found 424.1 [M+H]⁺.

Example 36

2-(2,5-Dichlorophenyl)-3-(4-(3-fluorophenyl)-4H-1,2,4-triazol-3-yl)imidazo[1,2-a]pyridine (535)

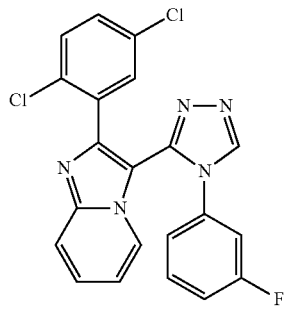 [SMILES: Fc1cccc(-n2cnnc2-c2c(-c3cc(Cl)ccc3Cl)nc3ccccn23)c1]

¹H NMR (400 MHz, CDCl₃) δ: 9.07 (d, J=6.8 Hz, 1H), 8.33 (s, 1H), 7.74 (d, J=9.2 Hz, 1H), 7.46-7.42 (m, 1H), 7.14-7.00 (m, 5H), 6.93 (s, 1H), 6.50 (d, J=8.00 Hz 1H), 6.43 (d, J=8.8 Hz, 1H). LC-MS ESI m/z; found 424.1 [M+H]⁺.

Example 37

2-(2,5-Dichlorophenyl)-3-(4-(1-methyl-1H-indol-5-yl)-4H-1,2,4-triazol-3-yl)imidazo[1,2-a]pyridine (536)

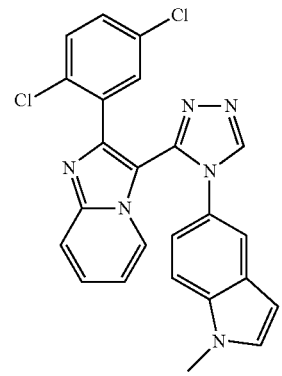 [SMILES: Cn1ccc2cc(-n3cnnc3-c3c(-c4cc(Cl)ccc4Cl)nc4ccccn34)ccc21]

¹H NMR (400 MHz, CDCl₃) δ: 9.15 (d, J=6.8 Hz, 1H), 8.37 (s, 1H), 7.69 (d, J=8.8 Hz, 1H), 7.42-7.34 (m, 1H), 7.09 (s, 1H), 7.05-7.03 (m, 3H), 7.02-6.95 (m, 3H) 6.80 (d, J=8.4 Hz, 1H), 6.64 (s, 1H), 6.45 (d, J=8.4 Hz, 1H), 6.28 (s, 1H), 3.77 (s, 3H). LC-MS ESI m/z; found 459.1 [M+H]⁺.

Example 38

2-(2,5-Dichlorophenyl)-3-(4-(4-(3-(trifluoromethyl)-1H-pyrazol-1-yl)phenyl)-4H-1,2,4-triazol-3-yl)imidazo[1,2-a]pyridine (537)

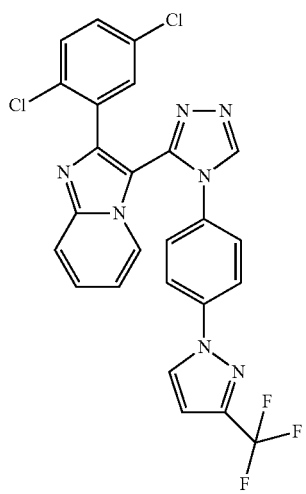 [SMILES: FC(F)(F)c1ccn(-c2ccc(-n3cnnc3-c3c(-c4cc(Cl)ccc4Cl)nc4ccccn34)cc2)n1]

¹H NMR (400 MHz, CDCl₃) δ: 9.10 (s, 1H), 8.75 (d, J=6.4 Hz, 1H), 7.93 (s, 1H), 7.75 (d, J=9.2 Hz, 1H), 7.53-7.49 (m, 1H), 7.37-7.33 (m, 4H), 7.16-7.12 (m, 4H), 6.97 (s, 1H). LC-MS ESI m/z; found 540.1 [M+H]⁺.

Example 39

4-(3-(2-(2,5-Dichlorophenyl)imidazo[1,2-a]pyridine-3-yl)-4H-1,2,4-triazol-4-yl)-3,5-dimethylisoxazole (538)

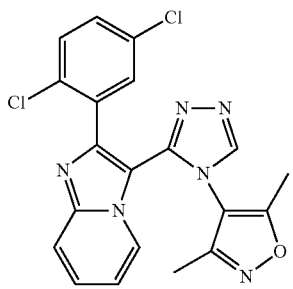 [SMILES: Cc1noc(C)c1-n1cnnc1-c1c(-c2cc(Cl)ccc2Cl)nc2ccccn12]

¹H NMR (400 MHz, CDCl₃) δ: 9.04 (s, 1H), 8.86 (d, J=6.4 Hz, 1H), 7.80 (d, J=9.2 Hz, 1H), 7.58-7.54 (m, 1H), 7.49-7.42 (m, 2H), 7.23-7.20 (m, 2H), 1.68 (s, 3H), 1.53 (s, 3H). LC-MS ESI m/z; found 425.1 [M+H]⁺.

Example 40

N-(4-(3-(2-(2,5-Dichlorophenyl)imidazo[1,2-a]pyridin-3-yl)-4H-1,2,4-triazol-4-yl)phenyl)-N-methylacetamide (539)

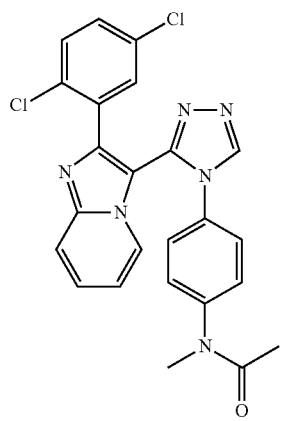 [SMILES: CC(=O)N(C)c1ccc(-n2cnnc2-c2c(-c3cc(Cl)ccc3Cl)nc3ccccn23)cc1]

¹H NMR (400 MHz, CDCl₃) δ: 8.94 (d, J=6.0 Hz, 1H), 8.30 (s, 1H), 7.69 (d, J=9.2 Hz, 1H), 7.38 (m, 1H), 7.19 (s, 1H), 7.08-6.92 (m, 5H), 6.72 (d, J=7.2 Hz, 2H), 3.21 (s, 3H), 1.98 (s, 3H). LC-MS ESI m/z; found 477.1 [M+H]⁺.

Example 41

2-(2,5-Dichlorophenyl)-3-(4-(6-methylpyridin-3-yl)-4H-1,2,4-triazol-3-yl)imidazo[1,2-a]pyridine (540)

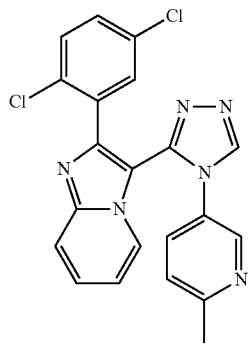 [SMILES: Cc1ccc(-n2cnnc2-c2c(-c3cc(Cl)ccc3Cl)nc3ccccn23)cn1]

¹H NMR (400 MHz, CDCl₃) δ: 9.07 (d, J=7.2 Hz, 1H), 8.33 (s, 1H), 7.86 (s, 1H), 7.73 (d, J=9.2 Hz, 1H), 7.46-7.42 (m, 1H), 7.18-7.14 (m, 2H), 7.07-7.04 (m, 1H), 6.93 (s, 1H), 6.92 (s, 2H), 2.56 (s, 3H). LC-MS ESI m/z; found 421.1 [M+H]⁺.

Example 42

6-(3-(2-(2,5-Dichlorophenyl)imidazo[1,2-a]pyridin-3-yl)-4H-1,2,4-triazol-4-yl)quinoline (541)

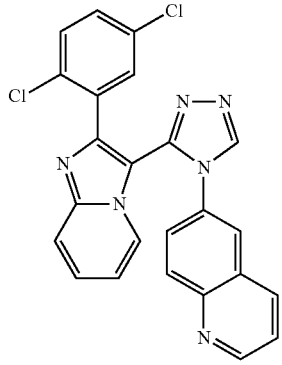 [SMILES: Clc1ccc(Cl)c(-c2nc3ccccn3c2-c2nncn2-c2ccc3ncccc3c2)c1]

$^1$H NMR (400 MHz, CDCl$_3$) δ: 9.17 (d, J=7.2 Hz, 1H), 8.98 (s, 1H), 8.45 (s, 1H), 7.93-7.89 (m, 2H), 7.74 (d, J=8.8 Hz, 1H), 7.47-7.44 (m, 2H), 7.25 (m, 1H), 7.11-7.07 (m, 1H), 7.02 (d, J=8.8 Hz, 1H), 6.94 (d, J=8.4 Hz, 1H), 6.81 (d, J=8.4 Hz, 1H) 6.71 (s, 1H). LC-MS ESI m/z; found 457.1 [M+H]$^+$.

Example 43

N-(2-Chloro-4-(3-(2-(2,5-dichlorophenyl)imidazo[1,2-a]pyridin-3-yl)-4H-1,2,4-triazol-4-yl)phenyl)acetamide (542)

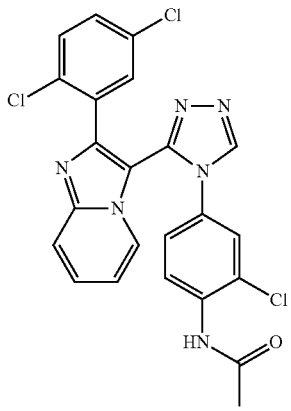 [SMILES: CC(=O)Nc1ccc(-n2cnnc2-c2c(-c3cc(Cl)ccc3Cl)nc3ccccn23)cc1Cl]

$^1$H NMR (400 MHz, CDCl$_3$) δ: 9.10 (d, J=6.4 Hz, 1H), 8.29 (s, 1H), 8.23 (d, J=8.8 Hz, 1H), 7.71 (d, J=9.2 Hz, 1H), 7.61 (s, 1H), 7.44-7.41 (m, 1H), 7.15-7.11 (m, 2H), 7.07-7.03 (m, 1H), 6.99 (s, 1H), 6.73 (s, 1H), 6.60 (d, J=9.2 Hz, 1H), 2.24 (s, 3H). LC-MS ESI m/z; found 497 [M+H]$^+$.

Example 44

3-(4-(4-Chlorobenzyl)-4H-1,2,4-triazol-3-yl)-2-(2,5-dichlorophenyl)imidazo[1,2-a]pyridine (543)

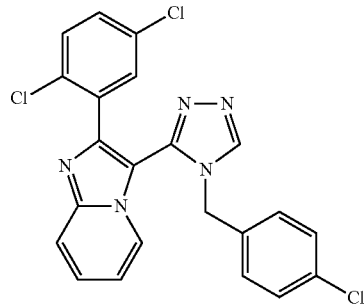 [SMILES: Clc1ccc(Cn2cnnc2-c2c(-c3cc(Cl)ccc3Cl)nc3ccccn23)cc1]

$^1$H NMR (400 MHz, CDCl$_3$) δ: 8.43 (d, J=7.2 Hz, 1H), 8.19 (s, 1H), 7.70 (d, J=8.8 Hz, 1H), 7.49 (s, 1H), 7.38-7.34 (m, 1H), 7.26-7.18 (m, 2H), 7.11 (d, J=8.4 Hz, 2H), 6.91-6.88 (m, 1H), 6.63 (d, J=8.4 Hz, 2H), 4.62 (s, 2H). LC-MS ESI m/z; found 454 [M+H]$^+$.

Example 45

4-(3-(2-(2,5-Dichlorophenyl)imidazo[1,2-a]pyridin-3-yl)-4H-1,2,4-triazol-4-yl)-1H-indazole (544)

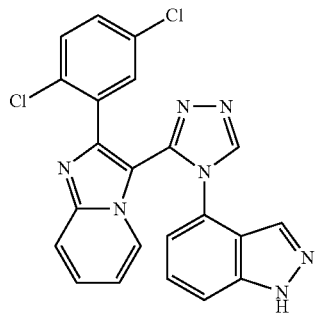 [SMILES: Clc1ccc(Cl)c(-c2nc3ccccn3c2-c2nncn2-c2cccc3[nH]ncc23)c1]

$^1$H NMR (400 MHz, CDCl$_3$) δ: 10.66 (br, 1H), 9.19 (d, J=7.2 Hz, 1H), 8.53 (s, 1H), 7.72 (d, J=9.2 Hz, 1H), 7.57 (s, 1H), 7.44 (d, J=8.0 Hz, 2H), 7.16-7.08 (m, 2H), 6.79 (d, J=8.8 Hz, 1H), 6.98 (d, J=8.8 Hz, 1H), 6.62 (s, 1H), 6.47 (d, J=7.6 Hz, 1H). LC-MS ESI m/z; found 446.1 [M+H]$^+$.

Example 46

4-(3-(2-(2,5-Dichlorophenyl)imidazo[1,2-a]pyridin-3-yl)-4H-1,2,4-triazol-4-yl)-1-methyl-1H-indazole (545)

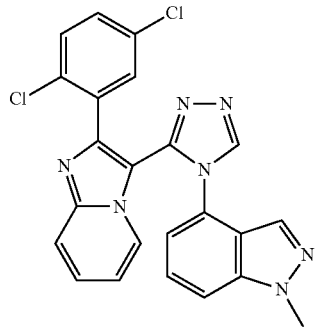 [SMILES: Cn1ncc2c(-n3cnnc3-c3c(-c4cc(Cl)ccc4Cl)nc4ccccn34)cccc21]

¹H NMR (400 MHz, CDCl₃) δ: 9.18 (d, J=6.4 Hz, 1H), 8.51 (s, 1H), 7.70 (d, J=8.8 Hz, 1H), 7.65-7.61 (m, 2H), 7.36 (d, J=8.8 Hz, 1H), 7.16-7.13 (m, 1H), 7.10-7.07 (m, 1H), 6.81 (d, J=8.4 Hz, 1H), 6.65 (d, J=8.4 Hz, 1H), 6.56 (s, 1H), 6.42 (d, J=6.8 Hz, 1H), 4.08 (m, 3H). LC-MS ESI m/z; found 460.1 [M+H]⁺.

Example 47

2-(2,5-Dichlorophenyl)-3-(4-(4-(4-methylpiperazin-1-yl)phenyl)-4H-1,2,4-triazol-3-yl)imidazo[1,2-a]pyridine (546)

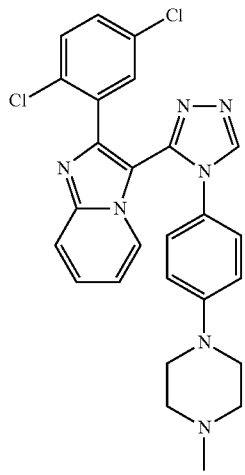 [SMILES: CN1CCN(c2ccc(-n3cnnc3-c3c(-c4cc(Cl)ccc4Cl)nc4ccccn34)cc2)CC1]

¹H NMR (400 MHz, CDCl₃) δ: 9.03 (d, J=6.8 Hz, 1H), 8.28 (s, 1H), 7.71 (d, J=9.2 Hz, 1H), 7.42-7.38 (m, 1H), 7.13-6.98 (m, 4H), 6.53 (m, 4H), 3.19 (m, 4H), 2.55 (m, 4H), 2.35 (s, 3H). LC-MS ESI m/z; found 504.1 [M+H]⁺.

Example 48

4-(3-(2,5-Dichlorophenyl)imidazo[1,2-a]pyridine-3-yl)-4H-1,2,4-triazol-4-yl)-N,N-dimethylbenzamide (547)

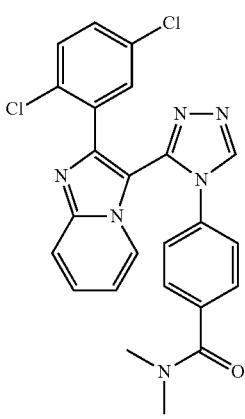 [SMILES: CN(C)C(=O)c1ccc(-n2cnnc2-c2c(-c3cc(Cl)ccc3Cl)nc3ccccn23)cc1]

¹H NMR (400 MHz, CDCl₃) δ: 8.96 (d, J=6.8 Hz, 1H), 8.33 (s, 1H), 7.73 (d, J=8.8 Hz, 1H), 7.43-7.39 (m, 1H), 7.26-7.22 (m, 2H), 7.14-7.02 (m, 4H), 6.77 (d, J=8 Hz, 2H), 6.78-6.76 (m, 2H). LC-MS ESI m/z; found 477.1 [M+H]⁺.

Example 49

4-(3-(2-(2,5-Dichlorophenyl)imidazo[1,2-a]pyridine-3-yl)-4H-1,2,4-triazol-4-yl)benzoic acid (548)

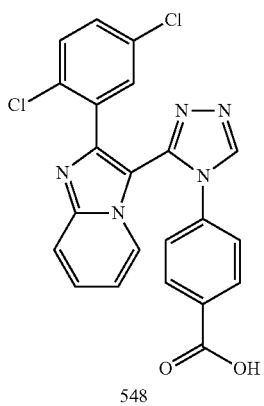

To a solution of ethyl 4-(3-(2-(2,5-dichlorophenyl)imidazo[1,2-a]pyridine-3-yl)-4H-1,2,4-triazol-4-yl)benzoate (532) (30 mg, 0.0627 mmol) in MeOH (3 mL) and THF (3 mL) was added 1N LiOH (3 mL) and the was stirred at room temperature over night. All volatiles were concentrated in vacuo, water was added and the mixture was acidified to pH 3 with 1N HCl. The reaction mixture was extracted with ethyl acetate, and the organic layer was dried over sodium sulfate, filtered, and concentrated in vacuo to yield 4-(3-(2-(2,5-dichlorophenyl)imidazo[1,2-a]pyridine-3-yl)-4H-1,2,4-triazol-4-yl)benzoic acid (548). ¹H NMR (400 MHz, CDCl₃) δ: 9.01 (s, 1H), 8.87 (d, J=6.8 Hz, 1H), 7.75 (d, J=9.6 Hz, 1H), 7.67 (d, J=8.4 Hz, 2H), 7.54-7.50 (m, 1H), 7.31-7.26 (m, 2H), 7.20-7.16 (m, 1H), 6.96 (d, J=8.4 Hz, 2H), 6.71 (s, 1H). LC-MS ESI m/z; found 450.1 [M+H]⁺.

Example 50

2-(2-Chloro-5-fluorophenyl)-3-(1-(4-chlorophenyl)-1H-tetrazol-5-yl)imidazo[1,2-a]pyrimidine (549)

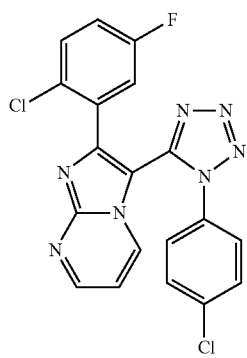 [SMILES: Fc1ccc(Cl)c(-c2nc3ncccn3c2-c2nnnn2-c2ccc(Cl)cc2)c1]

$^1$H NMR (400 MHz, CDCl$_3$) δ 8.76-8.66 (m, 1H), 8.10 (d, J=7.2, 1H), 7.59-7.41 (m, 5H), 7.41-7.32 (m, 1H), 7.29-7.21 (m, 1H), 7.06-6.99 (m, 1H). LC-MS ESI m/z; found 426.0 [M+H]$^+$.

Example 51

2-(2-Chloro-5-fluorophenyl)-3-(1-(4-chlorophenyl)-1H-tetrazol-5-yl)-5,6,7,8-tetrahydroimidazo[1,2-a]pyrimidine (550)

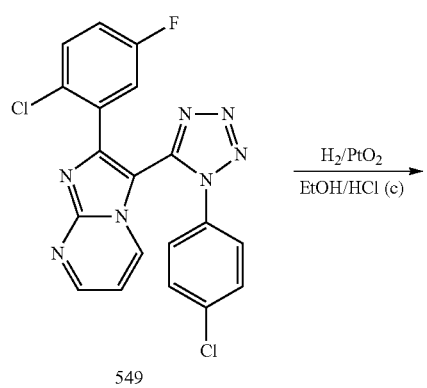

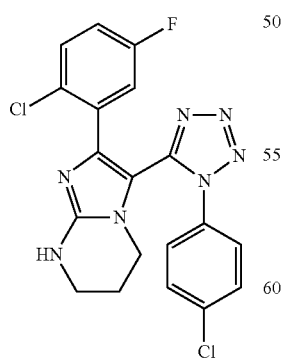

A pressure vessel was charged with 2-(2-chloro-5-fluorophenyl)-3-(1-(4-chlorophenyl)-1H-tetrazol-5-yl)imidazo[1,2-a]pyrimidine (549) (100 mg, 0.23 mmol), platinum (IV) oxide (0.5 mg, 0.0023 mmol), 1 drops of concentrated HCl, in ethanol (3 mL) and pressurized with hydrogen gas to 4 psi and was shaken overnight. The reaction was filtered through celite and concentrated in vacuo to provide 2-(2-chloro-5-fluorophenyl)-3-(1-(4-chlorophenyl)-1H-tetrazol-5-yl)-5,6,7,8-tetrahydroimidazo[1,2-a]pyrimidine (550). $^1$H NMR (400 MHz, CDCl$_3$) δ 7.40-7.20 (m, 5H), 7.05-6.95 (m, 1H), 6.94-6.85 (m, 1H), 5.69 (br, 1H), 3.85-3.75 (m, 1H), 3.65-3.55 (m, 1H), 3.50-3.40 (m, 2H), 2.15-2.00 (m, 2H). LC-MS ESI m/z; found 430.0 [M+H]$^+$.

Example 52

5-(1-(4-Chlorophenyl)-1H-tetrazol-5-yl)-6-(2,5-dichlorophenyl)imidazo[2,1-b]oxazole (551)

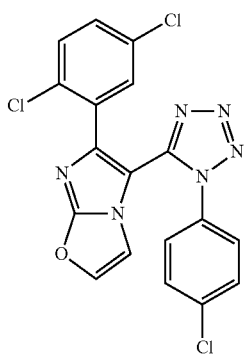 [SMILES: Clc1ccc(-n2nnnc2-c2c(-c3cc(Cl)ccc3Cl)nc3occn23)cc1]

$^1$H NMR (400 MHz, CDCl$_3$) δ 7.95 (d, J=1.6, 1H), 7.62 (d, J=1.6, 1H), 7.21-7.05 (m, 6H), 6.99 (d, J=8.5, 1H). LC-MS ESI m/z; found 431.0 [M+H]$^+$.

Example 53

3-(1-(4-Chlorophenyl)-1H-tetrazol-5-yl)-2-(2,5-dichlorophenyl)imidazo[1,2-a]pyridine (552)

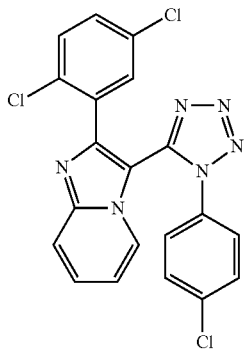 [SMILES: Clc1ccc(-n2nnnc2-c2c(-c3cc(Cl)ccc3Cl)nc3ccccn23)cc1]

$^1$H NMR (400 MHz, CDCl$_3$) δ 9.05 (d, J=6.9, 1H), 7.99 (d, J=8.9, 1H), 7.70-7.57 (m, 1H), 7.27-7.12 (m, 5H), 7.04 (s, 1H), 6.95-6.87 (m, 2H). LC-MS m/z; found 441.0 [M+H]$^+$.

Example 54

3-(4-(4-Chlorophenyl)-4H-1,2,4-triazol-3-yl)-2-(2,5-dichlorophenyl)imidazo[1,2-a]pyridine (553)

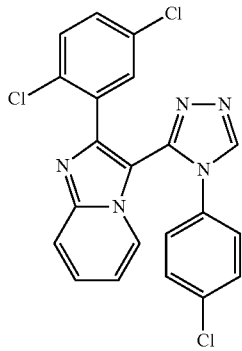 [SMILES: Clc1ccc(-n2cnnc2-c2c(-c3cc(Cl)ccc3Cl)nc3ccccn23)cc1]

$^1$H NMR (400 MHz, CDCl$_3$) δ 9.26 (d, J=6.8, 1H), 8.47 (s, 1H), 8.37 (d, J=9.3, 1H), 7.96-7.81 (m, 1H), 7.51-7.40 (m, 1H), 7.34-7.28 (m, 1H), 7.25-7.14 (m, 3H), 7.11-7.06 (m, 1H), 6.73-6.64 (m, 2H). LC-MS ESI m/z; found 440.0 [M+H]$^+$.

Example 55

3-(1-(4-Chlorophenyl)-1H-1,2,4-triazol-5-yl)-2-(2,5-dichlorophenyl)imidazo[1,2-a]pyridine (554)

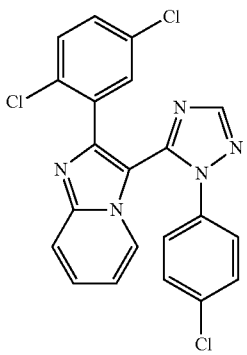 [SMILES: Clc1ccc(-n2ncnc2-c2c(-c3cc(Cl)ccc3Cl)nc3ccccn23)cc1]

$^1$H NMR (400 MHz, CDCl$_3$) δ 9.02 (d, J=7.0, 1H), 8.34 (s, 1H), 8.18 (d, J=9.2, 1H), 7.80-7.67 (m, 1H), 7.36-7.28 (m, 1H), 7.26-7.21 (m, 1H), 7.20-7.10 (m, 3H), 7.04-6.97 (m, 1H), 6.89-6.79 (m, 2H). LC-MS ESI m/z; found 440.0 [M+H]$^+$.

Example 56

3-(1-(4-Chlorophenyl)-1H-tetrazol-5-yl)-2-(2,5-dichlorophenyl)imidazo[1,2-b]pyridazine (555)

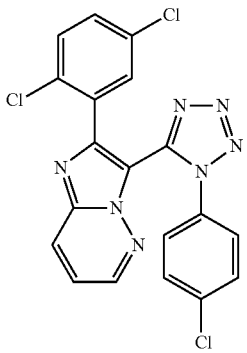

$^1$H NMR (400 MHz, CDCl$_3$) δ 8.27 (dd, J=4.5, 1.5, 1H), 8.05 (dd, J=9.3, 1.5, 1H), 7.35 (d, J=2.4, 1H), 7.25-7.16 (m, 5H), 7.14-7.07 (m, 2H). LC-MS ESI m/z; found 442.0 [M+H]$^+$.

Example 57

3-(1-(4-Chlorophenyl)-1H-tetrazol-5-yl)-2-(2,5-dichlorophenyl)imidazo[1,2-a]pyrazine (556)

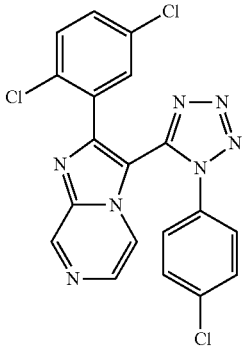 [SMILES: Clc1ccc(-n2nnnc2-c2c(-c3cc(Cl)ccc3Cl)nc3cnccn23)cc1]

$^1$H NMR (400 MHz, DMSO-d$_6$) δ 9.35 (s, 1H), 8.83 (d, J=4.7, 1H), 8.26 (d, J=4.7, 1H), 7.43-7.37 (m, 1H), 7.33-7.28 (m, 3H), 7.24-7.18 (m, 2H), 7.04-6.99 (m, 1H). LC-MS ESI m/z; found 442.0 [M+H]$^+$.

Example 58

2-(2-Chlorophenyl)-3-(1-(4-chlorophenyl)-1H-imidazol-2-yl)imidazo[1,2-a]pyridine (557)

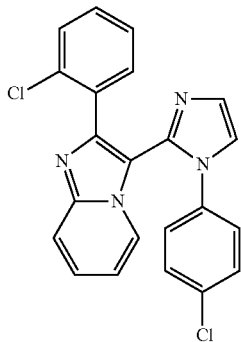 [SMILES: Clc1ccc(-n2ccnc2-c2c(-c3ccccc3Cl)nc3ccccn23)cc1]

$^1$H NMR (400 MHz, CDCl$_3$) δ 8.92 (d, J=7.1, 1H), 7.70 (d, J=9.1, 1H), 7.45 (s, 1H), 7.37-7.30 (m, 1H), 7.21-7.00 (m, 4H), 7.00-6.84 (m, 4H), 6.63-6.52 (m, 2H). LC-MS ESI m/z; found 405.1 [M+H]$^+$.

Example 59

3-(1-(4-Chlorophenyl)-1H-tetrazol-5-yl)-2-(2,5-dichlorophenyl)imidazo[1,2-a]pyrimidine (558)

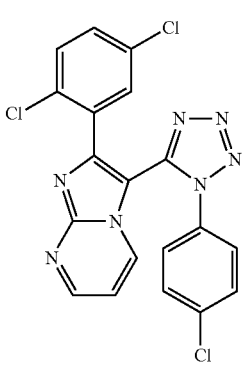 [SMILES: Clc1ccc(-n2nnnc2-c2c(-c3cc(Cl)ccc3Cl)nc3ncccn23)cc1]

¹H NMR (400 MHz, CDCl₃) δ 8.76-8.64 (m, 1H), 8.13-8.03 (m, 1H), 7.58 (s, 1H), 7.53-7.43 (m, 6H), 7.08-6.93 (m, 1H). LC-MS ESI m/z; found 442.0 [M+H]⁺.

Example 60

3-(1-(4-Chlorophenyl)-1H-tetrazol-5-yl)-2-(2,5-dichlorophenyl)-5,6,7,8-tetrahydroimidazo[1,2-a]pyridine (559)

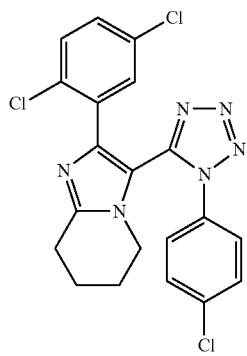 [SMILES: Clc1ccc(-n2nnnc2-c2c(-c3cc(Cl)ccc3Cl)nc3n2CCCC3)cc1]

¹H NMR (400 MHz, CDCl₃) δ 7.20-7.12 (m, 2H), 7.11-6.98 (m, 2H), 6.96-6.85 (m, 3H), 4.34-4.21 (m, 2H), 3.10-2.93 (m, 2H), 2.19-2.01 (m, 4H). LC-MS ESI m/z; found 445.0 [M+H]⁺.

Example 61

3-(1-(4-Chlorophenyl)-1H-imidazol-2-yl)-2-(2,5-dichlorophenyl)-5,6,7,8-tetrahydroimidazo[1,2-a]pyridine (560)

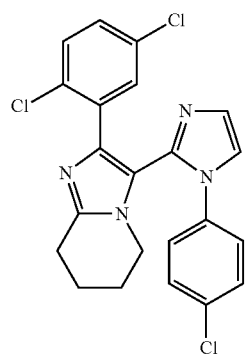 [SMILES: Clc1ccc(-n2ccnc2-c2c(-c3cc(Cl)ccc3Cl)nc3n2CCCC3)cc1]

¹H NMR (400 MHz, CDCl₃) δ 7.19 (s, 1H), 7.06-6.91 (m, 5H), 6.72 (s, 1H), 6.60-6.49 (m, 2H), 4.23-4.09 (m, 2H), 2.97-2.84 (m, 2H), 2.07-1.89 (m, 4H). LC-MS ESI m/z; found 443.1 [M+H]⁺.

Example 62

3-(1-(4-Chlorophenyl)-1H-imidazol-2-yl)-2-(2,5-dichlorophenyl)imidazo[1,2-b]pyridazine (561)

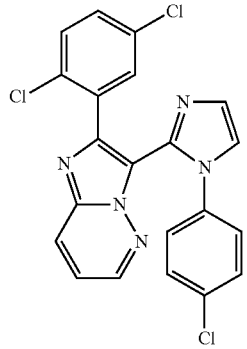 [SMILES: Clc1ccc(-n2ccnc2-c2c(-c3cc(Cl)ccc3Cl)nc3cccnn23)cc1]

¹H NMR (400 MHz, CDCl₃) δ 8.47-8.36 (m, 1H), 8.02 (d, J=9.0, 1H), 7.47 (s, 1H), 7.23-7.14 (m, 4H), 7.13-7.03 (m, 3H), 6.78-6.69 (m, 2H). LC-MS ESI m/z; found 440.0 [M+H]⁺.

Example 63

2-(2,5-Dichlorophenyl)-3-(1-(4-(trifluoromethyl)phenyl)-1H-tetrazol-5-yl)imidazo[1,2-a]pyridine (562)

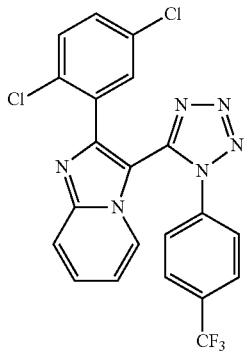 [SMILES: FC(F)(F)c1ccc(-n2nnnc2-c2c(-c3cc(Cl)ccc3Cl)nc3ccccn23)cc1]

¹H NMR (400 MHz, CDCl₃) δ 9.04 (d, J=6.9, 1H), 7.81 (d, J=8.9, 1H), 7.58-7.41 (m, 3H), 7.21-6.97 (m, 6H). LC-MS ESI m/z; found 475.0 [M+H]⁺.

Example 64

2-(2,5-Dichlorophenyl)-3-(1-(4-(trifluoromethyl)phenyl)-1H-tetrazol-5-yl)imidazo[1,2-b]pyridazine (563)

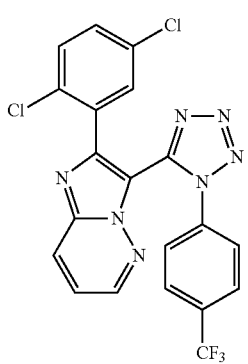 [SMILES: FC(F)(F)c1ccc(-n2nnnc2-c2c(-c3cc(Cl)ccc3Cl)nc3cccnn23)cc1]

¹H NMR (400 MHz, CDCl₃) δ 8.35-8.23 (m, 1H), 8.17-8.05 (m, 1H), 7.64-7.51 (m, 2H), 7.50-7.34 (m, 3H), 7.30-7.23 (m, 3H). LC-MS ESI m/z; found 476.0[M+H]⁺.

Example 65

2-(2,5-Dichlorophenyl)-3-(1-(4-(trifluoromethyl)phenyl)-1H-imidazol-2-yl)imidazo[1,2-a]pyridine (564)

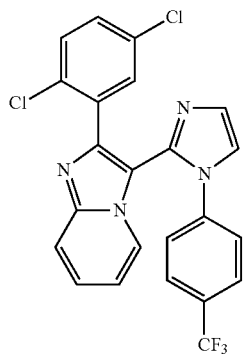 [SMILES: FC(F)(F)c1ccc(-n2ccnc2-c2c(-c3cc(Cl)ccc3Cl)nc3ccccn23)cc1]

¹H NMR (400 MHz, CDCl₃) δ 8.97 (d, J=7.3, 1H), 7.71 (d, J=8.7, 1H), 7.49 (s, 1H), 7.42-7.31 (m, 3H), 7.17 (s, 1H), 7.11-7.06 (m, 2H), 7.03-6.95 (m, 1H), 6.90-6.86 (m, 1H), 6.84-6.76 (m, 2H). LC-MS ESI m/z; found 473.1 [M+H]⁺.

Example 66

2-(2,5-Dichlorophenyl)-3-(1-(4-(trifluoromethyl)phenyl)-1H-imidazol-2-yl)imidazo[1,2-b]pyridazine (565)

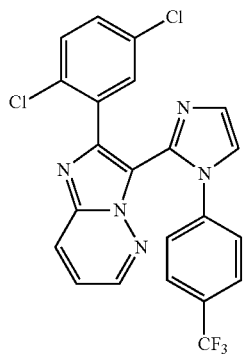 [SMILES: FC(F)(F)c1ccc(-n2ccnc2-c2c(-c3cc(Cl)ccc3Cl)nc3cccnn23)cc1]

¹H NMR (400 MHz, DMSO-d₆) δ 8.50-8.39 (m, 1H), 8.29-8.19 (m, 1H), 7.77 (s, 1H), 7.60-7.51 (m, 2H), 7.44-7.31 (m, 4H), 7.16-7.03 (m, 3H). LC-MS ESI m/z; found 474.0 [M+H]⁺.

Example 67

4-(5-(2-(2,5-Dichlorophenyl)imidazo[1,2-a]pyridin-3-yl)-1H-tetrazol-1-yl)benzonitrile (566)

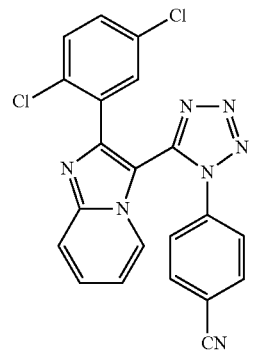 [SMILES: N#Cc1ccc(-n2nnnc2-c2c(-c3cc(Cl)ccc3Cl)nc3ccccn23)cc1]

¹H NMR (400 MHz, CDCl₃) δ 9.01 (d, J=6.4, 1H), 7.82 (d, J=9.3, 1H), 7.58-7.48 (m, 3H), 7.21-7.07 (m, 5H), 7.01-6.96 (m, 1H). LC-MS ESI m/z; found 432.0 [M+H]⁺.

Example 68

4-(2-(2-(2,5-Dichlorophenyl)imidazo[1,2-a]pyridin-3-yl)-1H-imidazol-1-yl)benzonitrile (567)

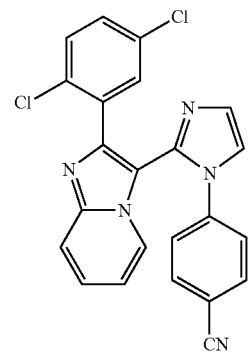 [SMILES: N#Cc1ccc(-n2ccnc2-c2c(-c3cc(Cl)ccc3Cl)nc3ccccn23)cc1]

¹H NMR (400 MHz, CDCl₃) δ 8.96 (d, J=6.9, 1H), 7.71 (d, J=9.0, 1H), 7.49 (s, 1H), 7.43-7.34 (m, 3H), 7.17-7.09 (m, 3H), 7.05-6.97 (m, 1H), 6.87-6.74 (m, 3H). LC-MS ESI m/z; found 430.1 [M+H]⁺.

Example 69

6-(3-(2-(3-Chlorophenyl)imidazo[1,2-a]pyridin-3-yl)-4H-1,2,4-triazol-4-yl)-1H-indazole (568)

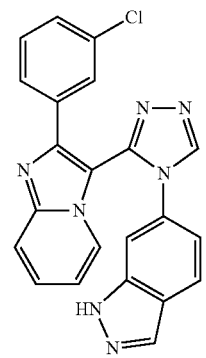 [SMILES: Clc1cccc(-c2nc3ccccn3c2-c2nncn2-c2ccc3cn[nH]c3c2)c1]

¹H NMR (400 MHz, CDCl₃) δ 10.34-9.94 (m, 1H), 8.81 (d, J=6.7, 1H), 8.49 (s, 1H), 8.04 (s, 1H), 7.71 (d, J=8.9, 1H), 7.48 (d, J=8.5, 1H), 7.40 (d, J=8.3, 1H), 7.09-6.90 (m, 4H), 6.78 (s, 1H), 6.42 (d, J=8.8, 1H). LC-MS ESI m/z; found 412.1 [M+H]⁺.

Example 70

3-(4-(4-chloro-3-(trifluoromethyl)phenyl)-4H-1,2,4-triazol-3-yl)-2-(2,5-dichlorophenyl)imidazo[1,2-a]pyridine (569)

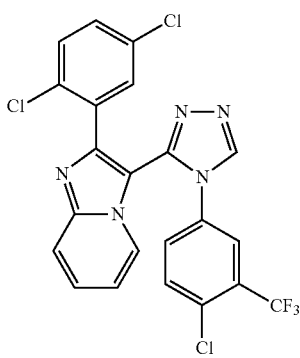 [SMILES: FC(F)(F)c1cc(-n2cnnc2-c2c(-c3cc(Cl)ccc3Cl)nc3ccccn23)ccc1Cl]

¹H NMR (400 MHz, CDCl₃) δ 9.12 (d, J=7.2, 1H), 8.34 (s, 1H), 7.75 (d, J=8.8, 1H), 7.48-7.44 (m, 1H), 7.32 (d, J=8.8, 1H), 7.17-7.07 (m, 4H), 7.01 (s, 1H), 6.85 (d, J=8.8, 1H). LC-MS ESI m/z; found 508.0 [M+H]⁺.

Example 71

2-(2,5-dichlorophenyl)-3-(4-(1-methyl-1H-indol-6-yl)-4H-1,2,4-triazol-3-yl)imidazo[1,2-a]pyridine (570)

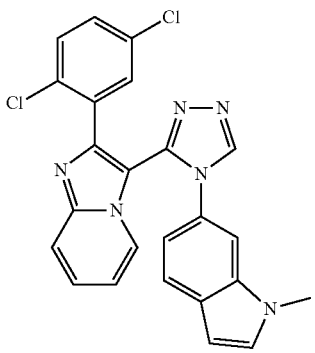 [SMILES: Cn1ccc2ccc(-n3cnnc3-c3c(-c4cc(Cl)ccc4Cl)nc4ccccn34)cc21]

¹H NMR (400 MHz, CDCl₃) δ 9.14 (d, J=6.4, 1H), 8.39 (s, 1H), 7.71 (d, J=8.8, 1H), 7.43-7.39 (m, 1H), 7.33 (d, J=8.0, 1H), 7.10 (s, 1H), 7.06-7.04 (m, 1H), 6.91-6.87 (m, 2H), 6.74 (s, 1H), 6.63 (s, 1H), 6.46 (s, 1H), 6.37 (d, J=8.4, 1H), 3.64 (s, 3H). LC-MS ESI m/z; found 459.1 [M+H]⁺.

Example 72

6-chloro-3-(3-(2-(2,5-dichlorophenyl)imidazo[1,2-a]pyridin-3-yl)-4H-1,2,4-triazol-4-yl)-1-methyl-1H-indazole (571)

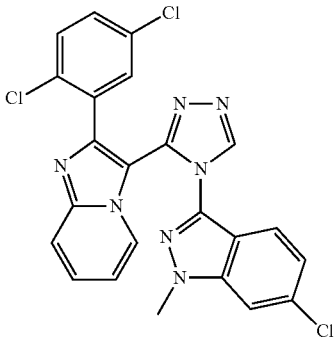 [SMILES: Cn1nc(-n2cnnc2-c2c(-c3cc(Cl)ccc3Cl)nc3ccccn23)c2ccc(Cl)cc21]

¹H NMR (400 MHz, CDCl₃) δ 9.27 (d, J=7.2, 1H), 8.48 (s, 1H), 7.72 (d, J=9.2, 1H), 7.46-7.44 (m, 1H), 7.34 (s, 1H), 7.10-7.03 (m, 2H), 6.93 (d, J=8.8, 1H), 6.77-6.7 (m, 3H), 3.86 (s, 3H). LC-MS ESI m/z; found 494.1 [M+H]⁺.

Example 73

2-(2,5-dichlorophenyl)-3-(4-(5-methylpyridin-2-yl)-4H-1,2,4-triazol-3-yl)imidazo[1,2-a]pyridine (572)

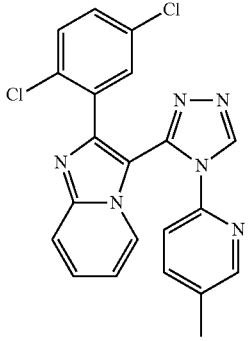 [SMILES: Cc1ccc(-n2cnnc2-c2c(-c3cc(Cl)ccc3Cl)nc3ccccn23)nc1]

¹H NMR (400 MHz, CDCl₃) δ 9.05 (d, J=6.8, 1H), 8.51 (s, 1H), 8.01 (s, 1H), 7.73 (d, J=8.8, 1H), 7.44-7.40 (m, 1H), 7.32 (d, J=8.8, 1H), 7.14-7.08 (m, 2H), 7.06-7.02 (m, 2H), 6.63 (d, J=7.6, 1H), 2.34 (s, 3H). LC-MS ESI m/z; found 421.1 [M+H]⁺.

Example 74

2-(2,5-dichlorophenyl)-3-(4-(pyrimidin-5-yl)-4H-1,2,4-triazol-3-yl)imidazo[1,2-a]pyridine (573)

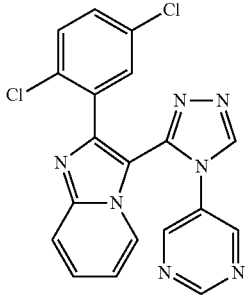 [SMILES: Clc1ccc(Cl)c(-c2nc3ccccn3c2-c2nncn2-c2cncnc2)c1]

¹H NMR (400 MHz, CDCl₃) δ 9.12-9.09 (m, 2H), 8.37 (s, 1H), 8.18 (m, 2H), 7.76 (d, J=9.6, 1H), 7.50-7.46 (m, 1H), 7.21 (s, 2H), 7.12-7.09 (m, 1H), 6.99 (s, 1H). LC-MS ESI m/z; found 408.0 [M+H]⁺.

Example 75

2-(2,5-dichlorophenyl)-3-(4-(4-(pyrrolidin-1-yl)phenyl)-4H-1,2,4-triazol-3-yl)imidazo[1,2-a]pyridine (574)

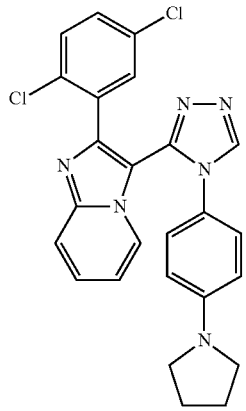 [SMILES: Clc1ccc(Cl)c(-c2nc3ccccn3c2-c2nncn2-c2ccc(N3CCCC3)cc2)c1]

¹H NMR (400 MHz, DMSO-d₆) δ 8.85-8.83 (m, 2H), 7.72 (d, J=9.0, 1H), 7.50-7.46 (m, 1H), 7.30-7.25 (m, 2H), 7.16-7.13 (m, 1H), 6.84 (s, 1H), 6.56 (d, J=8.7, 2H), 6.14 (d, J=8.5, 2H), 3.15 (m, 4H), 1.95 (m, 4H). LC-MS ESI m/z; found 475.1 [M+H]⁺.

Example 76

4-(2-(2-(2,5-dichlorophenyl)imidazo[1,2-b]pyridazin-3-yl)-1H-imidazol-1-yl)benzonitrile (575)

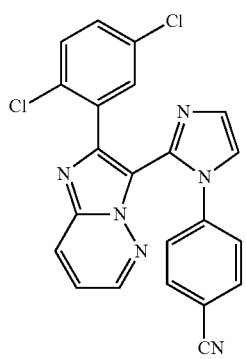 [SMILES: N#Cc1ccc(-n2ccnc2-c2c(-c3cc(Cl)ccc3Cl)nc3cccnn23)cc1]

¹H NMR (400 MHz, CDCl₃) δ 8.42-8.34 (m, 1H), 8.06 (d, J=9.1, 1H), 7.54 (s, 1H), 7.46 (d, J=8.3, 2H), 7.30-7.27 (m, 1H), 7.24-7.16 (m, 3H), 7.12 (s, 1H), 7.01 (d, J=8.3, 2H). LC-MS ESI m/z; found 431.0 [M+H]⁺.

Example 77

3-(5-(4-chlorophenyl)-4H-1,2,4-triazol-3-yl)-2-(2,5-dichlorophenyl)imidazo[1,2-a]pyridine (576)

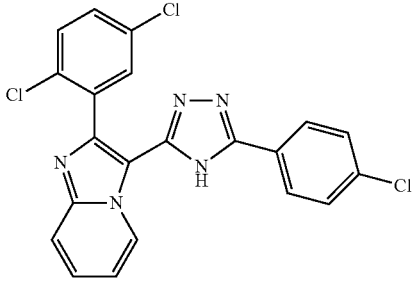 [SMILES: Clc1ccc(-c2nnc(-c3c(-c4cc(Cl)ccc4Cl)nc4ccccn34)[nH]2)cc1]

¹H NMR (400 MHz, CDCl₃) δ 9.70 (d, J=5.6, 1H), 8.05 (br, 1H), 7.76 (d, J=9.2, 1H), 7.64 (s, 1H), 7.46-7.26 (m, 7H), 7.15-7.13 (m, 1H). LC-MS ESI m/z; found 440.0 [M+H]⁺.

Example 78

2-(2,5-dichlorophenyl)-3-(4-(1-methylindolin-5-yl)-4H-1,2,4-triazol-3-yl)imidazo[1,2-a]pyridine (577)

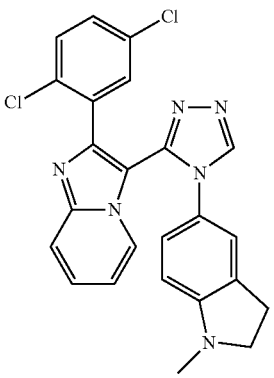

¹H NMR (400 MHz, CDCl₃) δ 9.06 (d, J=6.8, 1H), 8.30 (s, 1H), 7.69 (d, J=8.8, 1H), 7.40-7.37 (m, 1H), 7.08-6.99 (m, 6H), 6.69 (d, J=7.2, 1H), 3.37 (t, J=8.2, 2H), 2.92 (t, J=8.2, 2H), 2.55 (s, 3H). LC-MS ESI m/z; found 461.1 [M+H]⁺.

Example 79

5-(3-(2-(2,5-dichlorophenyl)imidazo[1,2-a]pyridin-3-yl)-4H-1,2,4-triazol-4-yl)-N,N-dimethylpyridin-2-amine (578)

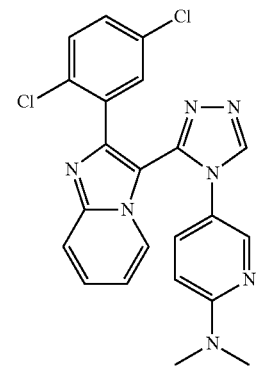 [SMILES: CN(C)c1ccc(-n2cnnc2-c2c(-c3cc(Cl)ccc3Cl)nc3ccccn23)cn1]

¹H NMR (400 MHz, CDCl₃) δ 9.06 (d, J=6.4, 1H), 8.27 (s, 1H), 7.69 (d, J=8.8, 1H), 7.46 (s, 1H), 7.41-7.37 (m, 1H), 7.16-7.01 (m, 4H), 6.70 (d, J=9.2, 1H), 6.08 (d, J=9.2, 1H), 3.4 (s, 6H). LC-MS ESI m/z; found 450.1 [M+H]⁺.

Example 80

5-(3-(2-(2,5-dichlorophenyl)imidazo[1,2-a]pyridin-3-yl)-4H-1,2,4-triazol-4-yl)picolinonitrile (579)

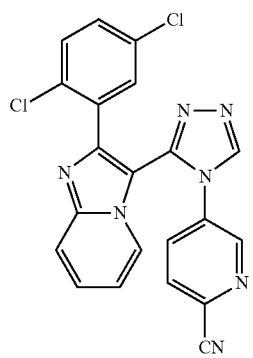 [SMILES: N#Cc1ccc(-n2cnnc2-c2c(-c3cc(Cl)ccc3Cl)nc3ccccn23)cn1]

¹H NMR (400 MHz, CDCl₃) δ 9.09 (d, J=6.8, 1H), 8.38 (s, 1H), 8.13 (s, 1H), 7.77 (d, J=8.8, 1H), 7.50-7.47 (m, 2H), 7.24-7.17 (m, 3H), 7.13-7.10 (m, 1H), 6.97 (s, 1H). LC-MS ESI m/z; found 432.0 [M+H]⁺.

Example 81

3-(4-(benzofuran-5-yl)-4H-1,2,4-triazol-3-yl)-2-(2,5-dichlorophenyl)imidazo[1,2-a]pyridine (580)

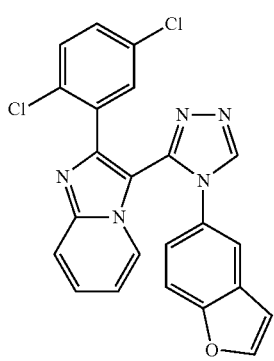 [SMILES: Clc1ccc(Cl)c(-c2nc3ccccn3c2-c2nncn2-c2ccc3occc3c2)c1]

¹H NMR (400 MHz, CDCl₃) δ 9.12 (d, J=6.8, 1H), 8.37 (s, 1H), 7.73-7.70 (m, 2H), 7.44-7.40 (m, 1H), 7.24 (s, 1H), 7.07-6.96 (m, 4H), 6.74 (s, 1H), 6.61-6.59 (m, 2H). LC-MS ESI m/z; found 446.1 [M+H]⁺.

Example 82

2-(2,5-dichlorophenyl)-3-(4-(2,3-dihydrobenzofuran-5-yl)-4H-1,2,4-triazol-3-yl)imidazo[1,2-a]pyridine (581)

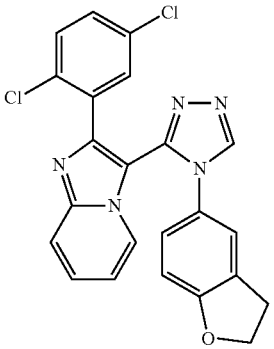 [SMILES: Clc1ccc(Cl)c(-c2nc3ccccn3c2-c2nncn2-c2ccc3c(c2)CCO3)c1]

¹H NMR (400 MHz, CDCl₃) δ 9.08 (d, J=7.2, 1H), 8.28 (s, 1H), 7.72 (d, J=9.2, 1H), 7.43-7.39 (m, 1H), 7.14 (m, 2H), 7.05-7.00 (m, 2H), 6.49-6.41 (m, 2H), 6.41-6.39 (m, 1H), 4.61 (t, J=8.8, 2H), 3.02 (t, J=8.8, 2H). LC-MS ESI m/z; found 448.1 [M+H]⁺.

Example 83

4-(3-(2-(4-chlorophenyl)pyrazolo[1,5-a]pyridin-3-yl)-4H-1,2,4-triazol-4-yl)benzonitrile (582)

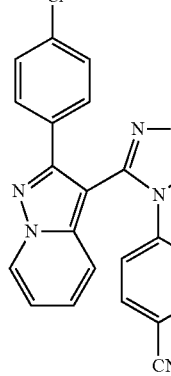

¹H NMR (400 MHz, CDCl₃) δ 8.53 (d, J=7.2, 1H), 8.36 (s, 1H), 7.90 (d, J=8.6, 1H), 7.40 (m, 3H), 7.17 (d, J=7.7, 2H), 7.10-6.97 (m, 3H), 6.79 (d, J=8.0, 2H). LC-MS ESI m/z; found 397.1 [M+H]⁺.

Example 84

3-(3-(4-chlorophenyl)-4H-1,2,4-triazol-4-yl)-2-(2,5-dichlorophenyl)imidazo[1,2-a]pyridine (583)

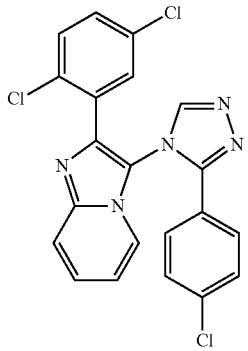 [SMILES: Clc1ccc(-c2nncn2-c2c(-c3cc(Cl)ccc3Cl)nc3ccccn23)cc1]

¹H NMR (400 MHz, CDCl₃) δ 8.34 (s, 1H), 7.79 (d, J=9.2, 1H), 7.64 (d, J=6.8, 1H), 7.43 (m, 1H), 7.31-7.15 (m, 7H), 6.99 (m, 1H).

Example 85

4-(3-(2-(4-chlorophenyl)pyrazolo[1,5-b]pyridazin-3-yl)-4H-1,2,4-triazol-4-yl)benzonitrile (584)

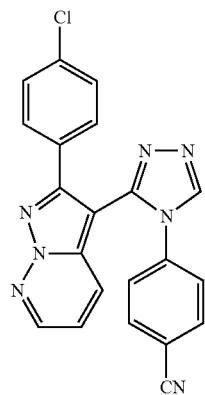 [SMILES: N#Cc1ccc(-n2cnnc2-c2c(-c3ccc(Cl)cc3)nn3ncccc23)cc1]

¹H NMR (400 MHz, CDCl₃) δ 8.47 (m, 1H), 8.36 (s, 1H), 8.32 (d, J=9.3, 1H), 7.41 (d, J=8.4, 2H), 7.24 (m, 1H), 7.22-7.12 (m, 2H), 7.08 (d, J=8.3, 2H), 6.79 (d, J=8.5, 2H). LC-MS ESI m/z; found 398.1 [M+H]⁺.

Example 86

3-(4-(7-chloro-2-methylbenzofuran-5-yl)-4H-1,2,4-triazol-3-yl)-2-(2,5-dichlorophenyl)imidazo[1,2-a]pyridine (585)

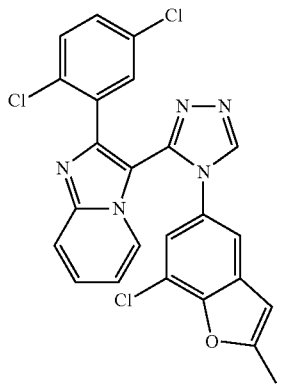 [SMILES: Cc1cc2cc(-n3cnnc3-c3c(-c4cc(Cl)ccc4Cl)nc4ccccn34)cc(Cl)c2o1]

¹H NMR (400 MHz, CDCl₃) δ 9.17 (d, J=7.2, 1H), 8.34 (s, 1H), 7.72 (d, J=9.2, 1H), 7.45-7.41 (m, 1H), 7.08-7.04 (m, 3H), 6.79 (s, 1H), 6.71 (s, 1H), 6.57 (s, 1H), 6.25 (s, 1H), 2.51 (s, 3H). LC-MS ESI m/z; found 494.0 [M+H]⁺.

Example 87

2-(4-chlorophenyl)-3-(4-(4-chlorophenyl)-4H-1,2,4-triazol-3-yl)pyrazolo[1,5-b]pyridazine (586)

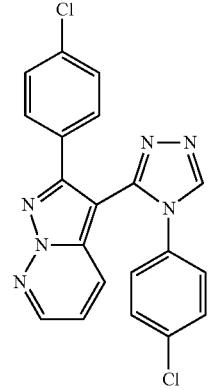

¹H NMR (400 MHz, CDCl₃) δ 8.44 (m, 1H), 8.32 (s, 1H), 8.27 (m, 1H), 7.24-7.18 (m, 3H), 7.12 (d, J=8.1, 2H), 7.06 (d, J=8.1, 2H), 6.59 (d, J=8.3, 2H). LC-MS ESI m/z; found 407.1 [M+H]⁺.

Example 88

2-(2-chlorophenyl)-3-(4-(4-chlorophenyl)-4H-1,2,4-triazol-3-yl)imidazo[1,2-b]pyridazine (587)

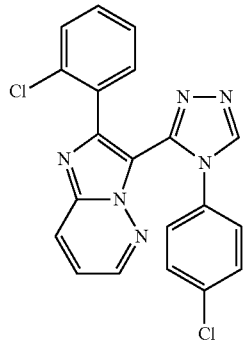 [SMILES: Clc1ccc(-n2cnnc2-c2c(-c3ccccc3Cl)nc3cccnn23)cc1]

¹H NMR (400 MHz, CDCl₃) δ 8.41 (s, 1H), 8.32 (s, 1H), 8.05 (d, J=9.1, 1H), 7.40-7.27 (m, 3H), 7.25-7.11 (m, 4H), 6.88 (d, J=8.1, 2H). LC-MS ESI m/z; found 407.0 [M+H]⁺.

Example 89

3-(4-(4-chlorophenyl)-4H-1,2,4-triazol-3-yl)-2-(2-fluoro-5-methylphenyl)imidazo[1,2-a]pyridine (588)

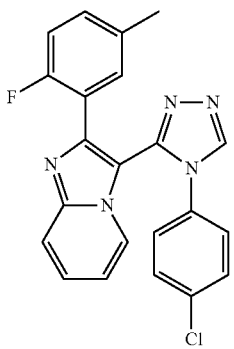 [SMILES: Cc1ccc(F)c(-c2nc3ccccn3c2-c2nncn2-c2ccc(Cl)cc2)c1]

¹H NMR (400 MHz, CDCl₃) δ 8.93 (s, 1H), 8.35 (s, 1H), 7.73 (d, J=9.1, 1H), 7.40 (s, 1H), 7.10-6.91 (m, 5H), 6.76 (d, J=9.7, 1H), 6.63 (s, 2H), 2.24 (s, 3H). LC-MS ESI m/z; found 404.1 [M+H]⁺.

Example 90

4-(3-(2-(2-chlorophenyl)imidazo[1,2-b]pyridazin-3-yl)-4H-1,2,4-triazol-4-yl)benzonitrile (589)

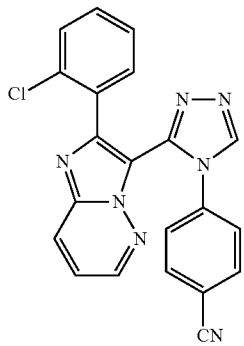 [SMILES: N#Cc1ccc(-n2cnnc2-c2c(-c3ccccc3Cl)nc3cccnn23)cc1]

¹H NMR (400 MHz, CDCl₃) δ 8.42 (s, 1H), 8.21 (s, 1H), 8.01 (d, J=9.2, 1H), 7.46 (d, J=8.5, 2H), 7.33 (s, 1H), 7.21 (m, 3H), 7.14 (s, 1H), 7.06 (d, J=9.2, 2H). LC-MS ESI m/z; found 398.1 [M+H]⁺.

Example 91

3-(4-(4-chlorophenyl)-4H-1,2,4-triazol-3-yl)-2-(2,5-dimethylphenyl)imidazo[1,2-a]pyridine (590)

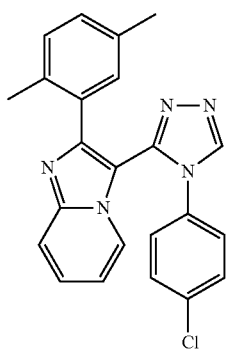 [SMILES: Cc1ccc(C)c(-c2nc3ccccn3c2-c2nncn2-c2ccc(Cl)cc2)c1]

¹H NMR (400 MHz, CDCl₃) δ 8.94 (d, J=7.0, 1H), 8.25 (s, 1H), 7.71 (d, J=9.1, 1H), 7.39 (m, 1H), 7.03 (m, 3H), 6.91 (m, 2H), 6.56 (s, 1H), 6.45 (d, J=8.7, 2H), 2.17 (s, 3H), 1.83 (s, 3H).

Example 92

2-(2,5-dichlorophenyl)-3-(4-(2-methylbenzofuran-5-yl)-4H-1,2,4-triazol-3-yl)imidazo[1,2-a]pyridine (591)

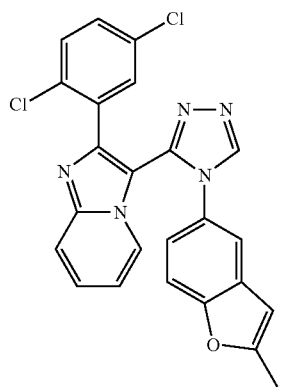 [SMILES: Cc1cc2cc(-n3cnnc3-c3c(-c4cc(Cl)ccc4Cl)nc4ccccn34)ccc2o1]

¹H NMR (400 MHz, CDCl₃) δ 9.09 (d, J=7.2, 1H), 8.34 (s, 1H), 7.68 (d, J=9.2, 1H), 7.41-7.37 (m, 1H), 7.09 (d, J=8.8, 1H), 7.04-7.00 (m, 2H), 6.94 (dd, J=8.8, 2.4, 1H), 6.77 (d, J=1.8, 1H), 6.72 (d, J=2.4, 1H), 6.47 (dd, J=8.4, 1.8, 1H), 6.16 (s, 1H), 2.44 (s, 3H). LC-MS ESI m/z; found 460.1 [M+H]⁺.

Example 93

3-(4-(4-chlorophenyl)-4H-1,2,4-triazol-3-yl)-2-(2,5-dichlorophenyl)-4,5,6,7-tetrahydro-2H-indazole (592)

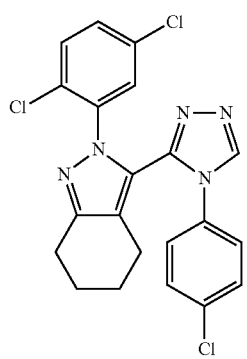 [SMILES: Clc1ccc(-n2cnnc2-c2c3c(nn2-c2cc(Cl)ccc2Cl)CCCC3)cc1]

¹H NMR (400 MHz, CDCl₃) δ 8.40 (s, 1H), 7.34 (d, J=8.5, 2H), 7.20 (m, 2H), 6.99 (s, 1H), 6.89 (d, J=8.5, 2H), 2.76 (m, 2H), 2.37 (m, 2H), 1.85 (m, 2H), 1.72 (m, 2H).

Example 94

4-(3-(2-(2,5-dichlorophenyl)-4,5,6,7-tetrahydro-2H-indazol-3-yl)-4H-1,2,4-triazol-4-yl)benzonitrile (593)

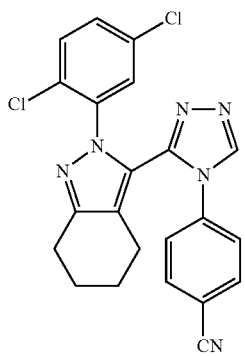 [SMILES: N#Cc1ccc(-n2cnnc2-c2c3c(nn2-c2cc(Cl)ccc2Cl)CCCC3)cc1]

$^1$H NMR (400 MHz, CDCl$_3$) δ 8.31 (s, 1H), 7.69 (d, J=8.4, 2H), 7.21 (s, 2H), 7.10 (d, J=8.4, 2H), 7.00 (s, 1H), 2.78 (m, 2H), 2.36 (m, 2H), 1.86 (m, 2H), 1.74 (m, 2H). LC-MS ESI m/z; found 435.1 [M+H]$^+$.

Example 95

4-(3-(2-(2,5-dichlorophenyl)pyrazolo[1,5-b]pyridazin-3-yl)-4H-1,2,4-triazol-4-yl)benzonitrile (594)

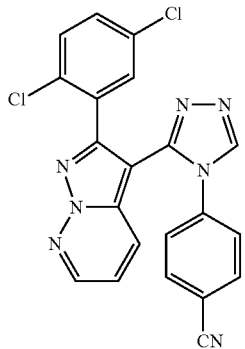 [SMILES: N#Cc1ccc(-n2cnnc2-c2c(-c3cc(Cl)ccc3Cl)nn3ncccc23)cc1]

$^1$H NMR (400 MHz, CDCl$_3$) δ 8.59-8.46 (m, 2H), 8.32 (s, 1H), 7.47 (d, J=8.6, 2H), 7.39-7.24 (m, 1H), 7.22-7.09 (m, 2H), 6.96-6.83 (m, 3H). LC-MS ESI m/z; found 432.0 [M+H]$^+$.

Example 96

Stimulation of cAMP

Compounds of Formula (I) were evaluated in an assay demonstrating agonism of GPR131. This assay was developed using a stable cell line expressing human GPR131.

To measure cAMP activity in response to GPR131 agonists, GPR131 cells suspended in DMEM/F12 medium with 1 mM IBMX were seeded in 384 well plates at 5000 cells per well. After incubating with test compounds at 37° C. for 30 minutes cAMP was measured using a fluorescene resonance energy transfer cAMP kit from Cis Bio (Bedford, Mass.) according to the manufacturer's instructions. Briefly, cells were lysed, and cAMP levels determined by competitive immunoassay using D2 labeled cAMP, and europium cryptate tagged anti cAMP antibody. Decreases in the FRET signal (fluorescence ratio (665 nm/620 m) correspond to increases in intracellular cAMP levels.

Activities of test compounds in Table 1 below are expressed as percent activity at 1.1 μM compound compared to the maximal stimulatory activity of lithocholic acid (LCA) (determined at 3.3 μM LCA).

TABLE 1

| Compound | Percent Activity @ 1.1 μM (of 3.3 uM LCA) (%) |
|---|---|
| 507 | 100 |
| 510 | 100 |
| 513 | 100 |
| 515 | 100 |
| 533 | 100 |
| 536 | 100 |
| 552 | 100 |
| 555 | 100 |
| 560 | 100 |
| 561 | 100 |
| 564 | 100 |
| 565 | 100 |
| 519 | 99.9 |
| 553 | 99.9 |
| 554 | 99.9 |
| 567 | 99.9 |
| 516 | 99.8 |
| 557 | 99.7 |
| 566 | 99.7 |
| 529 | 99.6 |
| 535 | 99.6 |
| 563 | 99.5 |
| 501 | 99.4 |
| 506 | 99.4 |
| 505 | 99.1 |
| 524 | 99.1 |
| 526 | 98.9 |
| 530 | 98.9 |
| 518 | 98.4 |
| 562 | 97.9 |
| 500 | 97.4 |
| 503 | 97.4 |
| 504 | 97.4 |
| 527 | 97.1 |
| 534 | 96.8 |
| 540 | 96 |
| 568 | 96 |
| 520 | 95.7 |
| 551 | 95.7 |
| 523 | 95.2 |
| 559 | 94.6 |
| 541 | 93.9 |
| 514 | 93.3 |
| 522 | 91.4 |
| 545 | 90.9 |
| 531 | 88.8 |
| 556 | 88.4 |
| 528 | 86.8 |
| 525 | 83.3 |
| 521 | 81.6 |

Example 97

Oral Glucose Tolerance and Incretin Measurements

Male mice (8-10 week old C57BL/6N, Harlan Laboratories, Inc.) are maintained on 18% Protein Rodent diet (Teklad Global Diets, Harlan Laboratories, Inc). Overnight fasted mice are randomized into groups (n=8-10) to receive the test compounds at a dose of 100 mg/kg or the vehicle (1% CMC, 2% TWEEN 80). Compounds are delivered orally via gavage. Blood glucose levels are measured by glucometer before administration of compounds and at 30 minutes post compound. The mice are then dosed orally with 3 g/kg glucose. Blood glucose measurements are taken 20, 40, 60, 90 and 120 minutes after glucose administration. Glucose levels are plotted against time and the incremental area under the curve (AUC) of the glucose excursion are determined from T=0 to T=120 min.

The effect of test compounds on the secretion of Glucagon-like peptide-1 (GLP-1) in C57/6N mice are determined at the end of the oral glucose tolerance test. Animals are anesthetized with pentobarbital and blood collected by heart puncture in potassium EDTA-coated microtainer tubes containing 10 μL/mLDPP-IV inhibitor and 500 KIU/mLAprotinin. Total GLP-1 are measured using Mouse/Rat Total Glucagon-like peptide-1 assay kit (Meso Scale Discovery) and MSD SECTOR 2400 Imager according to the manufacturer's instructions.

Example 98

Active GLP-1 Assessment of Test Compound and Sitagliptin in Normal C57BL/6 Mice

Male mice (8-10 week old C57BL/6N, Harlan Laboratories, Inc.) are maintained on 18% Protein Rodent diet as above. Overnight fasted mice are randomized into groups (n=9-10) to receive the test compounds at a dose of 100 mg/kg or sitagliptin at a dose of 1 mg/kg or combination of test compound and sitagliptin or the vehicle (1% CMC, 2% TWEEN 80). Sitagliptin is dosed 30 minutes prior to test compound.

Animals are anesthetized with pentobarbital (80 mg/mL in 10% ethanol) 30 minutes after test compound administration. Blood is collected by heart puncture in potassium EDTA-coated microtainer tubes) containing 10 μL/mLDPP-IV inhibitor and 500 KIU/mLAprotinin Bioactive GLP-1 is measured using an ELISA assay kit Statistically significant differences between compound treatment and vehicle is determined by One-way ANOVA with Bonferroni's post test. Differences with a p-value ≤0.05 are considered significant (***=P<0.001)

Example 99

Oral Glucose Tolerance Test (OGTT) of Test Compound and Sitagliptin in DIO Mice

Diet induced obese (DIO) male mice (C57BL/6J, 13-14 week old) are maintained on a 60 kcal % fat diet. Overnight fasted mice are randomized into groups (n=9-10) to receive the test compounds at a dose of 100 mg/kg or sitagliptin at a dose of 1 mg/kg or combination of the test compound and sitagliptin formulated together as one solution (test compound+sitagliptin) or vehicle (1% CMC, 2% TWEEN 80). Compounds are delivered orally via gavage. Blood glucose levels are measured by glucometer before administration of compounds and at 30 minutes post compound. The mice are then dosed orally with 2 g/kg glucose. Blood glucose measurements are taken at 20, 40, 60, 90 and 120 minutes after glucose administration. Glucose levels are plotted against time and the incremental area under the curve (AUC) of the glucose excursion is determined from T0 to T120. Statistically significant differences in AUC between compound treatment and vehicle are determined by one-way ANOVA with Bonferroni's post test. Differences with a p-value ≤0.05 are considered significant (*=P<0.05, ***=P<0.001)

Example 100

Oral Glucose Tolerance Test (OGTT) of Test Compound and Total Glucagon Like Peptide-2 (GLP-2) and Total Peptide YY (PYY) Measurements Diet induced obese (DIO) male mice (C57BL/6J, 18 week old) are maintained on a 60 kcal % fat diet. Mice are fasted for 9 hours and are randomized into groups (n=9-10) to receive vehicle (1% CMC, 2% TWEEN 80) or test compound at a dose of 100 mg/kg. Compounds are delivered orally via gavage, and 30 minutes later mice are dosed orally with 2 g/kg glucose.

The effect of GPR131 agonists on the secretion of total Glucagon-like peptide-2 (GLP-2) and total Peptide YY (PYY) is determined at the end of the oral glucose tolerance test (2 hours post glucose dosing). Animals are anesthetized with pentobarbital and blood collected by heart puncture in potassium EDTA-coated microtainer tubes containing 10 μL/mLDPP-IV inhibitor and 500 KIU/mLAprotinin. Total GLP-2 is measured using Total Glucagon-like peptide-2 assay kit and Total PYY is measured using Total Peptide YY assay kit.

Example 101

Gastric Emptying

To evaluate the effects of compounds of Formula (I) on gastric emptying, 8-10 week old male C57BL/6J mice (Harlan) are fasted for 16-18 hours, then treated orally or by intraperitoneal injection with either test compounds of Formula (I) (1-100 mg/kg) or vehicle (1% CMC, 2% TWEEN 80) 30 minutes prior to initiation of the gastric emptying study. Phenol red (0.05% PR in deionized water) is administered either in an aqueous or glucose solution (0.05% in 20% glucose). Immediately after PR administration (0 min), control group animals are sacrificed by cervical dislocation and the average amount of phenol red recovered is measured as 100% phenol red retention. The remainder of the animals from each group are sacrificed at various time-points following phenol red administration. The stomachs are isolated after clamping at both the pyloric and the cardiac ends. Clamped stomachs are transferred to a 50 mL conical tube containing 5 mL deionized water. Clamps are removed and each stomach is cut into fine pieces with scissors and stomach content is extracted by centrifugation at 3000 rpm for 10 minutes and supernatant is filtered to remove particulates. 1 mL of 1N NaOH is added to each 2 mL of filtered supernatant for color development. The concentration of phenol read is determine by measuring the absorbance of the extracted material at a wavelength of 558 nm and then converted to concentration by using the extinction coefficient of phenol red in aqueous solution.

The gastric emptying is calculated by the formula: % Gastric emptying=((A−B)/A)×100, where A is the average amount (absorbance) of phenol red recovered immediately after ingestion (the 100% retained group) and B is the amount (absorbance) of phenol red remaining in the stomach at a given time after ingestion.

Example 102

Improvement of Diabetes Parameters in Animal Models of Diabetes

Female ZDF rats (Charles River laboratories) are obtained at 6 weeks of age and acclimatized for 1 week before being placed on a high fat diet (RD 13004, Research Diets). Compounds of Formula (I) are administered to the rats by daily gavage at concentrations ranging from 0.3-300 mg/kg in 1% CMC, 2% TWEEN 80. Body weight and food intake is monitored daily. After 14 days of dosing, blood samples are taken from overnight fasted animals to measure glucose and insulin. Glucose is measured using a glucometer (Ascensia Elite XL, Bayer) and insulin is measured using rat insulin ELISA kit (ALPCO). Insulin and glucose levels are compared to those of vehicle treated animals to determine efficacy.

Ob/ob mice (Jackson) are obtained at 6 weeks of age and acclimatized for 1-2 week. Compounds of Formula (I) are administered by daily gavage at concentrations ranging from 0.3-300 mg/kg in 1% CMC, 2% TWEEN 80. Body weight and food intake is monitored daily. After 14 days of dosing, blood samples are taken from overnight fasted animals to measure glucose and insulin. Glucose is measured using a glucometer (Ascensia Elite XL, Bayer), insulin is measured using mouse insulin ELISA kit (ALPCO). Insulin and glucose levels are compared to those of vehicle treated animals to determine efficacy.

While the foregoing description describes specific embodiments, those with ordinary skill in the art will appreciate that various modifications and alternatives can be developed. Accordingly, the particular embodiments described above are meant to be illustrative only, and not to limit the scope of the invention, which is to be given the full breadth of the appended claims, and any and all equivalents thereof.

What is claimed is:

1. A compound of formula (I)

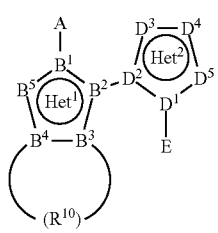

or a derivative thereof, wherein

A is an optionally substituted aryl or heteroaryl;

$D^1$ and $D^2$ are each independently C or N; and $D^3$, $D^4$, and $D^5$ are each independently $CR^2$, N, $NR^8$, or O, wherein $D^1$, $D^2$, $D^3$, $D^4$, and $D^5$ together form $Het^2$, which is an optionally substituted 5-membered heteroaryl;

E is alkyl, aryl, arylalkyl, cycloalkyl, heteroalkyl, heteroaryl, or heterocycloalkyl, each of which may be optionally substituted,

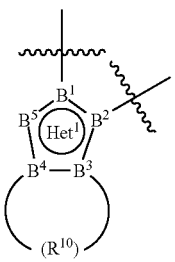

is selected from the group consisting of

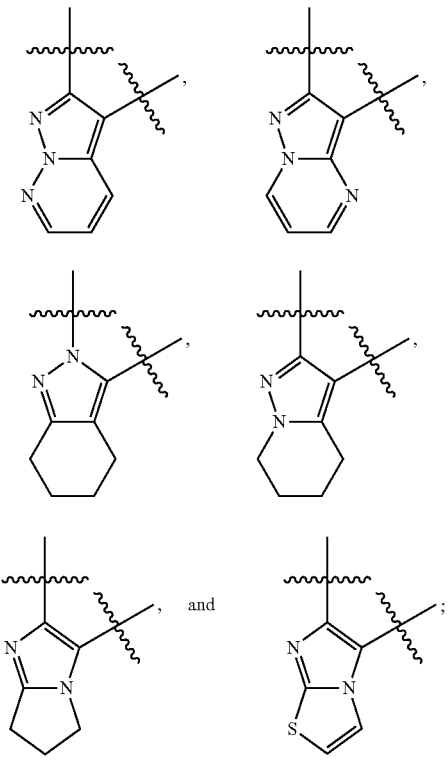

and $R^2$ is independently H, alkoxy, optionally substituted $C_{1-6}$alkyl, amido, amino, cyano, halo, hydroxyl, sulfonyl, or sulfonamido; and $R^8$ is H or optionally substituted $C_{1-6}$alkyl.

2. The compound of claim 1, wherein A is an optionally substituted phenyl or heteroaryl.

3. The compound of claim 2, wherein A is phenyl optionally substituted with one or more substituents selected from the group consisting of alkoxy, amido, amino, an optionally substituted $C_{1-6}$alkyl, carboxylate, cyano, halo, and hydroxyl.

4. The compound of claim 1, wherein $Het^2$ is selected from the group consisting of imidazole, triazole and tetrazole.

5. The compound of claim 1, wherein $D^2$ is carbon.

6. The compound of claim 1, wherein E is an optionally substituted aryl or heteroaryl.

7. A compound represented by Formula (Ib2)

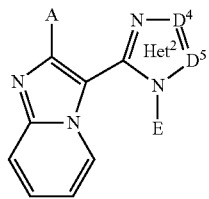

(Ib2)

or a derivative thereof, wherein
A is an optionally substituted aryl or heteroaryl;
$D^4$ and $D^5$ are each independently $CR^2$, or N, wherein $D^4$ and $D^5$ together with the two nitrogen attached thereto $Het^2$, which is an optionally substituted 5-membered heteroaryl;
E is aryl, cycloalkyl, heteroalkyl, heteroaryl, or heterocycloalkyl, each of which may be optionally substituted, or E is an unsubstituted alkyl; and
$R^2$ is independently H, alkoxy, optionally substituted $C_{1-6}$ alkyl, amido, amino, cyano, halo, hydroxyl, sulfonyl, or sulfonamido.

8. A compound represented by Formula (Ib3)

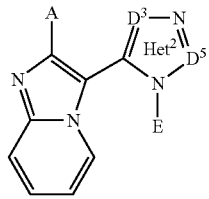

(Ib3)

or a derivative thereof, wherein
A is an optionally substituted aryl or heteroaryl;
$D^3$ and $D^5$ are each independently $CR^2$ or N, wherein $D^3$ and $D^5$ together with the two nitrogen attached thereto $Het^2$, which is an optionally substituted 5-membered heteroaryl;
E is aryl, cycloalkyl, heteroalkyl, heteroaryl, or heterocycloalkyl, each of which may be optionally substituted, or E is an unsubstituted alkyl; and
$R^2$ is independently H, alkoxy, optionally substituted $C_{1-6}$ alkyl, amido, amino, cyano, halo, hydroxyl, sulfonyl, or sulfonamido.

9. A compound selected from the group consisting of:
2-(2-Chlorophenyl)-3-(1-(4-chlorophenyl)-1H-tetrazol-5-yl)imidazo[1,2-a]pyridine;
2-(2-Chlorophenyl)-3-(4-(4-chlorophenyl)-4H-1,2,4-triazol-3-yl)imidazo[1,2-a]pyridine;
3-(4-Cyclohexyl-4H-1,2,4-triazol-3-yl)-2-(2,5-dichlorophenyl)imidazo[1,2-a]pyridine;
2-(2-Chlorophenyl)-3-(1-(4-chlorophenyl)-1H-1,2,4-triazol-5-yl)imidazo[1,2-a]pyridine;
3-(1-(4-Chlorophenyl)-3-methyl-1H-1,2,4-triazol-5-yl)-2-(2,5-dichlorophenyl)imidazo[1,2-a]pyridine;
3-(4-(4-Chlorophenyl)-5-methyl-4H-1,2,4-triazol-3-yl)-2-(2,5-dichlorophenyl)imidazo[1,2-a]pyridine;
3-(1-(4-Chlorophenyl)-1H-imidazol-2-yl)-2-(2,5-dichlorophenyl)imidazo[1,2-a]pyridine;
3-(1-(4-Chlorophenyl)-1H-imidazol-5-yl)-2-(2,5-dichlorophenyl)imidazo[1,2-a]pyridine;
2-(2,5-Dichlorophenyl)-3-(4-(pyridin-4-yl)-4H-1,2,4-triazol-3-yl)imidazo[1,2-a]pyridine;
2-(2,5-Dichlorophenyl)-3-(4-isopropyl-4H-1,2,4-triazol-3-yl)imidazo[1,2-a]pyridine;
4-(3-(2-(2,5-Dichlorophenyl)imidazo[1,2-a]pyridin-3-yl)-4H-1,2,4-triazol-4-yl)-N,N-dimethylaniline;
4-(4-(3-(2-(2,5-Dichlorophenyl)imidazo[1,2-a]pyridin-3-yl)-4H-1,2,4-triazol-4-yl)phenyl)morpholine;
2-(2,5-Dichlorophenyl)-3-(4-(4-(methylsulfonyl)phenyl)-4H-1,2,4-triazol-3-yl)imidazo[1,2-a]pyridine;
2-(2,5-Dichlorophenyl)-3-(4-(4-(trifluoromethyl)phenyl)-4H-1,2,4-triazol-3-yl)imidazo[1,2-a]pyridine;
5-(3-(2-(2,5-Dichlorophenyl)imidazo[1,2-a]pyridin-3-yl)-4H-1,2,4-triazol-4-yl)-1H-indazole;
4-(3-(2-(2,5-Dichlorophenyl)imidazo[1,2-a]pyridin-3-yl)-4H-1,2,4-triazol-4-yl)benzonitrile;
6-(3-(2-(2,5-Dichlorophenyl)imidazo[1,2-a]pyridin-3-yl)-4H-1,2,4-triazol-4-yl)-1H-indazole;
6-(3-(2-(2,5-Dichlorophenyl)imidazo[1,2-a]pyridin-3-yl)-4H-1,2,4-triazol-4-yl)-1-methyl-1H-benzo[d]imidazole;
5-(3-(2-(2,5-Dichlorophenyl)imidazo[1,2-a]pyridin-3-yl)-4H-1,2,4-triazol-4-yl)benzo[d]thiazole;
5-(3-(2-(2,5-Dichlorophenyl)imidazo[1,2-a]pyridin-3-yl)-4H-1,2,4-triazol-4-yl)-1-methyl-1H-indazole;
6-(3-(2-(2,5-Dichlorophenyl)imidazo[1,2-a]pyridin-3-yl)-4H-1,2,4-triazol-4-yl)-1-methyl-1H-indazole;
5-(3-(2-(2,5-Dichlorophenyl)imidazo[1,2-a]pyridin-3-yl)-4H-1,2,4-triazol-4-yl)-1-methyl-1H-benzo[d]imidazole;
6-(3-(2-(2-Chlorophenyl)imidazo[1,2-a]pyridin-3-yl)-4H-1,2,4-triazol-4-yl)-1H-indazole;
3-(4-(1H-Indazol-6-yl)-4H-1,2,4-triazol-3-yl)-2-(2,5-dichlorophenyl)imidazo[1,2-b]pyridazine;
3-(4-(4-Chlorophenyl)-4H-1,2,4-triazol-3-yl)-2-(4-fluorophenyl)pyrazolo[1,5-a]pyridine;
4-(4-Chlorophenyl)-3-(2-(2,5-dichlorophenyl)imidazo[1,2-a]pyridin-3-yl)-1H-1,2,4-triazol-5 (4H)-one;
4-(4-Chlorophenyl)-3-(2-(2,5-dichlorophenyl)imidazo[1,2-a]pyridin-3-yl)-1H-1,2,4-triazole-5 (4H)-thione;
3-(4-(4-Chlorophenyl)-5-methoxy-4H-1,2,4-triazol-3-yl)-2-(2,5-dichlorophenyl)imidazo[1,2-a]pyridine;
3-(4-(4-Chlorophenyl)-5-(methylthio)-4H-1,2,4-triazol-3-yl)-2-(2,5-dichlorophenyl)imidazo[1,2-a]pyridine;
2-(2,5-Dichlorophenyl)-3-(4-(4-ethylphenyl)-4H-1,2,4-triazol-3-yl)imidazo[1,2-a]pyridine;
2-(2,5-Dichlorophenyl)-3-(4-(4-isopropylphenyl)-4H-1,2,4-triazol-3-yl)imidazo[1,2-a]pyridine;
3-(4-([1,1'-Biphenyl]-4-yl)-4H-1,2,4-triazol-3-yl)-2-(2,5-dichlorophenyl)imidazo[1,2-a]pyridine;
Ethyl 4-(3-(2,5-dichlorophenyl)imidazo[1,2-a]pyridine-3-yl)-4H-1,2,4-triazol-4-yl)benzoate;
2-(2,5-Dichlorophenyl)-3-(4-(4-fluorophenyl)-4H-1,2,4-triazol-3-yl)imidazo[1,2-a]pyridine;
2-(2,5-Dichlorophenyl)-3-(4-(2-fluorophenyl)-4H-1,2,4-triazol-3-yl)imidazo[1,2-a]pyridine;
2-(2,5-Dichlorophenyl)-3-(4-(3-fluorophenyl)-4H-1,2,4-triazol-3-yl)imidazo[1,2-a]pyridine;
2-(2,5-Dichlorophenyl)-3-(4-(1-methyl-1H-indol-5-yl)-4H-1,2,4-triazol-3-yl)imidazo[1,2-a]pyridine;
2-(2,5-Dichlorophenyl)-3-(4-(4-(3-(trifluoromethyl)-1H-pyrazol-1-yl)phenyl)-4H-1,2,4-triazol-3-yl)imidazo[1,2-a]pyridine;
4-(3-(2-(2,5-Dichlorophenyl)imidazo[1,2-a]pyridine-3-yl)-4H-1,2,4-triazol-4-yl)-3,5-dimethylisoxazole;

N-(4-(3-(2-(2,5-Dichlorophenyl)imidazo[1,2-a]pyridin-3-yl)-4H-1,2,4-triazol-4-yl)phenyl)-N-methylacetamide;
2-(2,5-Dichlorophenyl)-3-(4-(6-methylpyridin-3-yl)-4H-1,2,4-triazol-3-yl)imidazo[1,2-a]pyridine;
6-(3-(2-(2,5-Dichlorophenyl)imidazo[1,2-a]pyridin-3-yl)-4H-1,2,4-triazol-4-yl)quinoline;
N-(2-Chloro-4-(3-(2-(2,5-dichlorophenyl)imidazo[1,2-a]pyridin-3-yl)-4H-1,2,4-triazol-4-yl)phenyl)acetamide;
3-(4-(4-Chlorobenzyl)-4H-1,2,4-triazol-3-yl)-2-(2,5-dichlorophenyl)imidazo[1,2-a]pyridine;
4-(3-(2-(2,5-Dichlorophenyl)imidazo[1,2-a]pyridin-3-yl)-4H-1,2,4-triazol-4-yl)-1H-indazole;
4-(3-(2-(2,5-Dichlorophenyl)imidazo[1,2-a]pyridin-3-yl)-4H-1,2,4-triazol-4-yl)-1-methyl-1H-indazole;
2-(2,5-Dichlorophenyl)-3-(4-(4-(4-methylpiperazin-1-yl)phenyl)-4H-1,2,4-triazol-3-yl)imidazo[1,2-a]pyridine;
4-(3-(2,5-Dichlorophenyl)imidazo[1,2-a]pyridine-3-yl)-4H-1,2,4-triazol-4-yl)-N,N-dimethylbenzamide;
4-(3-(2-(2,5-Dichlorophenyl)imidazo[1,2-a]pyridine-3-yl)-4H-1,2,4-triazol-4-yl)benzoic acid;
2-(2-Chloro-5-fluorophenyl)-3-(1-(4-chlorophenyl)-1H-tetrazol-5-yl)imidazo[1,2-a]pyrimidine;
2-(2-Chloro-5-fluorophenyl)-3-(1-(4-chlorophenyl)-1H-tetrazol-5-yl)-5,6,7,8-tetrahydroimidazo[1,2-a]pyrimidine;
5-(1-(4-Chlorophenyl)-1H-tetrazol-5-yl)-6-(2,5-dichlorophenyl)imidazo[2,1-b]oxazole;
3-(1-(4-Chlorophenyl)-1H-tetrazol-5-yl)-2-(2,5-dichlorophenyl)imidazo[1,2-a]pyridine;
3-(4-(4-Chlorophenyl)-4H-1,2,4-triazol-3-yl)-2-(2,5-dichlorophenyl)imidazo[1,2-a]pyridine;
3-(1-(4-Chlorophenyl)-1H-1,2,4-triazol-5-yl)-2-(2,5-dichlorophenyl)imidazo[1,2-a]pyridine;
3-(1-(4-Chlorophenyl)-1H-tetrazol-5-yl)-2-(2,5-dichlorophenyl)imidazo[1,2-b]pyridazine;
3-(1-(4-Chlorophenyl)-1H-tetrazol-5-yl)-2-(2,5-dichlorophenyl)imidazo[1,2-a]pyrazine;
2-(2-Chlorophenyl)-3-(1-(4-chlorophenyl)-1H-imidazol-2-yl)imidazo[1,2-a]pyridine;
3-(1-(4-Chlorophenyl)-1H-tetrazol-5-yl)-2-(2,5-dichlorophenyl)imidazo[1,2-a]pyrimidine;
3-(1-(4-Chlorophenyl)-1H-tetrazol-5-yl)-2-(2,5-dichlorophenyl)-5,6,7,8-tetrahydroimidazo[1,2-a]pyridine;
3-(1-(4-Chlorophenyl)-1H-imidazol-2-yl)-2-(2,5-dichlorophenyl)-5,6,7,8-tetrahydroimidazo[1,2-a]pyridine;
3-(1-(4-Chlorophenyl)-1H-imidazol-2-yl)-2-(2,5-dichlorophenyl)imidazo[1,2-b]pyridazine;
2-(2,5-Dichlorophenyl)-3-(1-(4-(trifluoromethyl)phenyl)-1H-tetrazol-5-yl)imidazo[1,2-a]pyridine;
2-(2,5-Dichlorophenyl)-3-(1-(4-(trifluoromethyl)phenyl)-1H-tetrazol-5-yl)imidazo[1,2-b]pyridazine;
2-(2,5-Dichlorophenyl)-3-(1-(4-(trifluoromethyl)phenyl)-1H-imidazol-2-yl)imidazo[1,2-a]pyridine;
2-(2,5-Dichlorophenyl)-3-(1-(4-(trifluoromethyl)phenyl)-1H-imidazol-2-yl)imidazo[1,2-b]pyridazine;
4-(5-(2-(2,5-Dichlorophenyl)imidazo[1,2-a]pyridin-3-yl)-1H-tetrazol-1-yl)benzonitrile;
4-(2-(2-(2,5-Dichlorophenyl)imidazo[1,2-a]pyridin-3-yl)-1H-imidazol-1-yl)benzonitrile;
6-(3-(2-(3-Chlorophenyl)imidazo[1,2-a]pyridin-3-yl)-4H-1,2,4-triazol-4-yl)-1H-indazole;
3-(4-(4-chloro-3-(trifluoromethyl)phenyl)-4H-1,2,4-triazol-3-yl)-2-(2,5-dichlorophenyl)imidazo[1,2-a]pyridine;
2-(2,5-dichlorophenyl)-3-(4-(1-methyl-1H-indol-6-yl)-4H-1,2,4-triazol-3-yl)imidazo[1,2-a]pyridine;
6-chloro-3-(3-(2-(2,5-dichlorophenyl)imidazo[1,2-a]pyridin-3-yl)-4H-1,2,4-triazol-4-yl)-1-methyl-1H-indazole;
2-(2,5-dichlorophenyl)-3-(4-(5-methylpyridin-2-yl)-4H-1,2,4-triazol-3-yl)imidazo[1,2-a]pyridine;
2-(2,5-dichlorophenyl)-3-(4-(pyrimidin-5-yl)-4H-1,2,4-triazol-3-yl)imidazo[1,2-a]pyridine;
2-(2,5-dichlorophenyl)-3-(4-(4-(pyrrolidin-1-yl)phenyl)-4H-1,2,4-triazol-3-yl)imidazo[1,2-a]pyridine;
4-(2-(2-(2,5-dichlorophenyl)imidazo[1,2-b]pyridazin-3-yl)-1H-imidazol-1-yl)benzonitrile;
3-(5-(4-chlorophenyl)-4H-1,2,4-triazol-3-yl)-2-(2,5-dichlorophenyl)imidazo[1,2-a]pyridine;
2-(2,5-dichlorophenyl)-3-(4-(1-methylindolin-5-yl)-4H-1,2,4-triazol-3-yl)imidazo[1,2-a]pyridine;
5-(3-(2-(2,5-dichlorophenyl)imidazo[1,2-a]pyridin-3-yl)-4H-1,2,4-triazol-4-yl)-N,N-dimethylpyridin-2-amine;
5-(3-(2-(2,5-dichlorophenyl)imidazo[1,2-a]pyridin-3-yl)-4H-1,2,4-triazol-4-yl)picolinonitrile;
3-(4-(benzofuran-5-yl)-4H-1,2,4-triazol-3-yl)-2-(2,5-dichlorophenyl)imidazo[1,2-a]pyridine;
2-(2,5-dichlorophenyl)-3-(4-(2,3-dihydrobenzofuran-5-yl)-4H-1,2,4-triazol-3-yl)imidazo[1,2-a]pyridine;
4-(3-(2-(4-chlorophenyl)pyrazolo[1,5-a]pyridin-3-yl)-4H-1,2,4-triazol-4-yl)benzonitrile;
3-(3-(4-chlorophenyl)-4H-1,2,4-triazol-4-yl)-2-(2,5-dichlorophenyl)imidazo[1,2-a]pyridine;
4-(3-(2-(4-chlorophenyl)pyrazolo[1,5-b]pyridazin-3-yl)-4H-1,2,4-triazol-4-yl)benzonitrile;
3-(4-(7-chloro-2-methylbenzofuran-5-yl)-4H-1,2,4-triazol-3-yl)-2-(2,5-dichlorophenyl)imidazo[1,2-a]pyridine;
2-(4-chlorophenyl)-3-(4-(4-chlorophenyl)-4H-1,2,4-triazol-3-yl)pyrazolo[1,5-b]pyridazine;
2-(2-chlorophenyl)-3-(4-(4-chlorophenyl)-4H-1,2,4-triazol-3-yl)imidazo[1,2-b]pyridazine;
3-(4-(4-chlorophenyl)-4H-1,2,4-triazol-3-yl)-2-(2-fluoro-5-methylphenyl)imidazo[1,2-a]pyridine;
4-(3-(2-(2-chlorophenyl)imidazo[1,2-b]pyridazin-3-yl)-4H-1,2,4-triazol-4-yl)benzonitrile;
3-(4-(4-chlorophenyl)-4H-1,2,4-triazol-3-yl)-2-(2,5-dimethylphenyl)imidazo[1,2-a]pyridine;
2-(2,5-dichlorophenyl)-3-(4-(2-methylbenzofuran-5-yl)-4H-1,2,4-triazol-3-yl)imidazo[1,2-a]pyridine;
3-(4-(4-chlorophenyl)-4H-1,2,4-triazol-3-yl)-2-(2,5-dichlorophenyl)-4,5,6,7-tetrahydro-2H-indazole;
4-(3-(2-(2,5-dichlorophenyl)-4,5,6,7-tetrahydro-2H-indazol-3-yl)-4H-1,2,4-triazol-4-yl)benzonitrile; and
4-(3-(2-(2,5-dichlorophenyl)pyrazolo[1,5-b]pyridazin-3-yl)-4H-1,2,4-triazol-4-yl)benzonitrile,
or a salt, racemate, or a tautomer thereof.

10. A pharmaceutical composition comprising a compound of claim 1 and a pharmaceutically acceptable carrier.

11. The compound of claim 1, wherein the derivative is a pharmaceutically acceptable salt or a tautomer.

12. A pharmaceutical composition comprising a compound of claim 9 and a pharmaceutically acceptable carrier.

13. The compound of claim 1, wherein

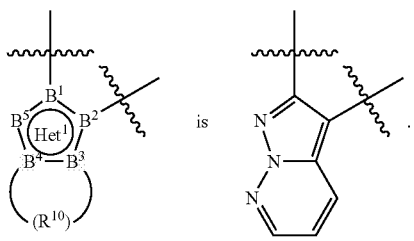 is 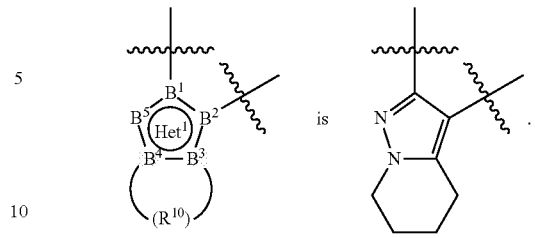

14. The compound of claim 1, wherein

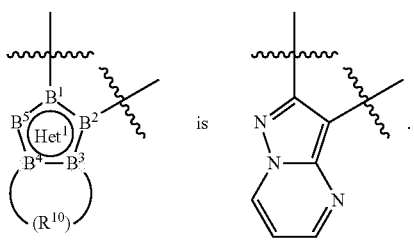 is 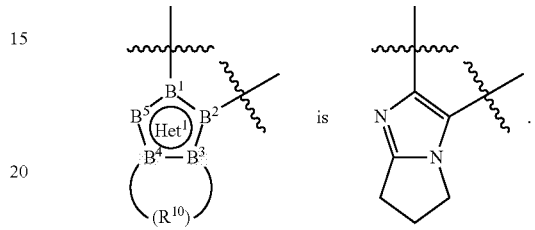

15. The compound of claim 1, wherein

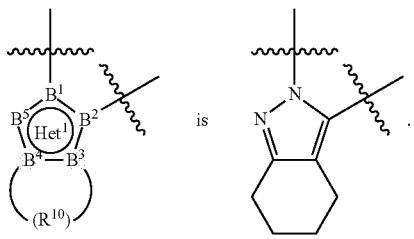 is 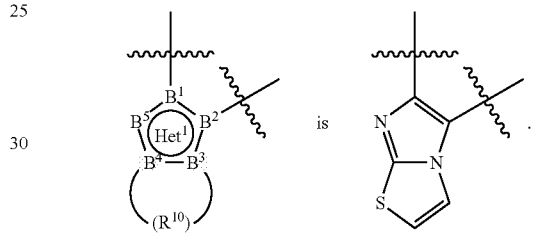

16. The compound of claim 1, wherein

17. The compound of claim 1, wherein

18. The compound of claim 1, wherein

19. A pharmaceutical composition comprising a compound of claim 7 and a pharmaceutically acceptable carrier.

20. A pharmaceutical composition comprising a compound of claim 8 and a pharmaceutically acceptable carrier.

* * * * *